(12) United States Patent
Xiong et al.

(10) Patent No.: US 11,014,943 B2
(45) Date of Patent: May 25, 2021

(54) AZETIDINE DERIVATIVE

(71) Applicant: CHIA TAI TIANQING PHARMACEUTICAL GROUP CO., LTD., Lianyungang (CN)

(72) Inventors: Jian Xiong, Jiangsu (CN); Cheng Xie, Jiangsu (CN); Kevin X Chen, Jiangsu (CN); Xiongbin Xu, Jiangsu (CN); Xuejin Zhang, Jiangsu (CN); Zhen Gong, Jiangsu (CN); Jian Li, Jiangsu (CN); Shuhui Chen, Jiangsu (CN); Aiming Zhang, Lianyungang (CN); Zhulian Jiang, Lianyungang (CN); Xiquan Zhang, Lianyungang (CN); Xin Tian, Lianyungang (CN)

(73) Assignee: CHIA TAI TIANQING PHARMACEUTICAL GROUP GO., LTD., Lianyungang (CN)

( * ) Notice: Subject to any disclaimer, the term of this patent is extended or adjusted under 35 U.S.C. 154(b) by 82 days.

(21) Appl. No.: 16/489,282

(22) PCT Filed: Feb. 28, 2018

(86) PCT No.: PCT/CN2018/077583
§ 371 (c)(1),
(2) Date: Aug. 27, 2019

(87) PCT Pub. No.: WO2018/157820
PCT Pub. Date: Sep. 7, 2018

(65) Prior Publication Data
US 2020/0115392 A1 Apr. 16, 2020

(30) Foreign Application Priority Data

Feb. 28, 2017 (CN) .......................... 201710112350.0
Sep. 8, 2017 (CN) .......................... 201710805883.7

(51) Int. Cl.
*C07F 5/02* (2006.01)
*A61P 35/00* (2006.01)

(52) U.S. Cl.
CPC .............. *C07F 5/025* (2013.01); *A61P 35/00* (2018.01); *C07F 5/02* (2013.01)

(58) Field of Classification Search
CPC ............. C07F 5/02; C07F 5/025; A61P 35/00
See application file for complete search history.

(56) References Cited

FOREIGN PATENT DOCUMENTS

| CN | 105732683 A | 7/2016 |
| CN | 110790780 A | 2/2020 |
| WO | 2006/086600 A1 | 8/2006 |

OTHER PUBLICATIONS

Dou, Q.P. et al; Overview of Proteasome Inhibitor-Based Anti-Cancer Therapies: Perspective on Bortezomib and Second Generation Proteasome Inhibitors Versus Future Generation Inhibitors of Ubiquitin-Proteasome System; Current Cancer Drug Targets; 14(6), Dec. 31, 2014, pp. 517-536.

Ruggeri, B., et al; The Development and Pharmacology of Proteasome Inhibitors for the Management and Treatment of Cancer; Advances in Pharmacology (San Diego, CA, US); vol. 57, Dec. 31, 2009; pp. 91-135.

State Intellectual Property Office of the P.R. China; International Search Report of International Application No. PCT/CN2018/077583, dated Jun. 1, 2018.

Dorsey, et al; Discovery of a Potent, Selective, and Orally Active Proteasome Inhibitor for the Treatment of Cancer; J. Med. Chem. (2008); 51; 1068-1072.

European Patent Office; Communication—Supplementary European Search Report; EP Appl. No. 18760796.5; dated Nov. 11, 2020; (6 pgs.).

*Primary Examiner* — Laura L Stockton

(74) *Attorney, Agent, or Firm* — Kilpatrick, Townsend & Stockton LLP

(57) ABSTRACT

Disclosed in the present application are a compound represented by formula (I), or a pharmaceutically acceptable salt, a tautomer thereof, a stereoisomer thereof, or a geometrical isomer thereof, and uses thereof in the preparation of drugs for treating or preventing multiple myeloma.

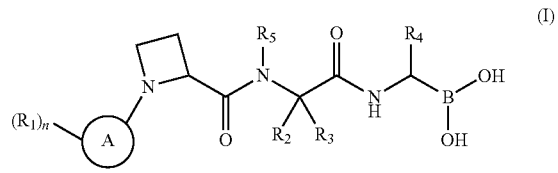

20 Claims, No Drawings

AZETIDINE DERIVATIVE

CROSS REFERENCE TO RELATED APPLICATIONS

The present application is a national phase application under 35 U.S.C. 371 claiming priority to PCT/CN2018/077583, filed Feb. 28, 2018, which application claims the benefits and properties of the Chinese invention patent application Nos. 201710112350.0 and 201710805883.7 filed with the China National Intellectual Property Administration on Feb. 28, 2017 and Sep. 8, 2017, respectively, which are incorporated herein by reference in their entireties.

TECHNICAL FIELD

The present application relates to a class of compounds or a pharmaceutically acceptable salt thereof for treating multiple myeloma, and to the use thereof in the preparation of a medicament for treating a disease associated with multiple myeloma.

BACKGROUND

Multiple myeloma (MM) is a malignant proliferative disease of plasma cells which is characterized by the abnormal proliferation of clonal plasma cells in the bone marrow, the destruction of hematopoietic function, the stimulation to bone to lead to the occurrence of osteolytic bone lesions, and the presence of monoclonal immunoglobulin or its fragment (M protein) that is detectable in serum and/or urine. Its clinical manifestations are bone pain, anemia, hypercalcemia, renal impairment, infection, bleeding and so on. Bortezomib is a reversible proteasome inhibitor that achieves the goal of treating multiple myeloma by promoting the apoptosis of myeloma cells. However, in the long-term treatment process, some patients with multiple myeloma have developed resistance to bortezomib. Therefore, there is still a need for a new and safe drug for the treatment of multiple myeloma.

SUMMARY OF THE INVENTION

In an aspect, the present application provides a compound of Formula (I), a pharmaceutically acceptable salt, a tautomer, a stereoisomer or a geometric isomer thereof,

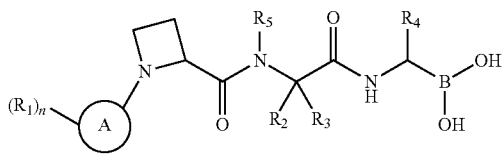

wherein, ring A is selected from the group consisting of $C_{3-6}$ cycloalkyl, phenyl and 5 to 10-membered heteroaryl;

n is selected from 0, 1, 2 or 3;

$R_1$ is each independently selected from the group consisting of halo, OH, $NH_2$, CN, $C_{1-3}$ alkyl, $C_{1-3}$ heteroalkyl and phenyl, wherein the $C_{1-3}$ alkyl, $C_{1-3}$ heteroalkyl or phenyl is each optionally substituted with 1, 2 or 3 Rs;

$R_2$ and $R_3$ are each independently selected from the group consisting of H, halo, OH, $NH_2$, CN, $C_{1-6}$ alkyl, $C_{1-6}$ heteroalkyl, $C_{3-6}$ cycloalkyl, $C_{3-6}$ cycloalkyl-$(CH_2)_{1-3}$— and phenyl-$(CH_2)_{1-3}$—, wherein the $C_{1-6}$ alkyl, $C_{1-6}$ heteroalkyl, $C_{3-6}$ cycloalkyl, $C_{3-6}$ cycloalkyl-$(CH_2)_{1-3}$— or phenyl-$(CH_2)_{1-3}$— is each optionally substituted with 1, 2 or 3 Rs; or $R_2$ and $R_3$ together with the carbon atom to which they are attached form a 3 to 6-membered ring;

$R_4$ is selected from the group consisting of $C_{1-6}$ alkyl and $C_{3-6}$ cycloalkyl-$(CH_2)_{1-3}$—, wherein the $C_{1-6}$ alkyl or $C_{3-6}$ cycloalkyl-$(CH_2)_{1-3}$— is each optionally substituted with 1, 2 or 3 Rs;

$R_5$ is selected from the group consisting of H and $C_{1-3}$ alkyl optionally substituted with 1, 2 or 3 Rs;

each R is independently selected from the group consisting of F, Cl, Br, I, OH, Me, $NH_2$, $NH(CH_3)$ and $N(CH_3)_2$;

wherein the prefix "hetero" in the $C_{1-3}$ heteroalkyl, $C_{1-6}$ heteroalkyl and 5 to 10-membered heteroaryl is each independently selected from the group consisting of —O—, —S—, —NH— and N; and in any one of the above cases, the number of heteroatom or group containing a heteroatom is independently selected from 1, 2 or 3.

In another aspect, the present application provides a pharmaceutical composition comprising the compound of Formula (I), a pharmaceutically acceptable salt, a tautomer, a stereoisomer or a geometric isomer thereof, and a pharmaceutically acceptable carrier, excipient or adjuvant.

In a further aspect, the present application provides a method for the prophylaxis or treatment of multiple myeloma, comprising administering to a subject in need thereof the compound of Formula (I), a pharmaceutically acceptable salt, a tautomer, a stereoisomer or a geometric isomer thereof, or a pharmaceutical composition thereof.

In still another aspect, the present application provides use of the compound of Formula (I), a pharmaceutically acceptable salt, a tautomer, a stereoisomer or a geometric isomer thereof, or a pharmaceutical composition thereof in the preparation of a medicament for the prophylaxis or treatment of multiple myeloma.

In yet another aspect, the present application provides the compound of Formula (I), a pharmaceutically acceptable salt, a tautomer, a stereoisomer or a geometric isomer thereof, or a pharmaceutical composition thereof for use in the prophylaxis or treatment of multiple myeloma.

In another aspect, the present application provides use of the compound of Formula (I), a pharmaceutically acceptable salt, a tautomer, a stereoisomer or a geometric isomer thereof, or a pharmaceutical composition thereof in the prophylaxis or treatment of multiple myeloma.

DETAILED DESCRIPTION OF THE INVENTION

The present application provides a compound of Formula (I), a pharmaceutically acceptable salt, a tautomer, a stereoisomer or a geometric isomer thereof,

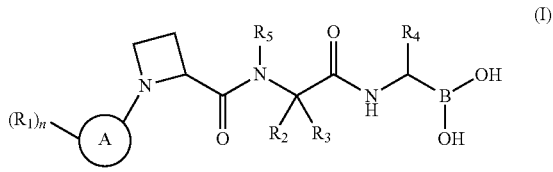

wherein, ring A is selected from the group consisting of $C_{3-6}$ cycloalkyl, phenyl and 5 to 10-membered heteroaryl;

n is selected from 0, 1, 2 or 3;

$R_1$ is each independently selected from the group consisting of halo, OH, $NH_2$, CN, $C_{1-3}$ alkyl, $C_{1-3}$ heteroalkyl and phenyl, wherein the $C_{1-3}$ alkyl, $C_{1-3}$ heteroalkyl or phenyl is each optionally substituted with 1, 2 or 3 Rs;

$R_2$ and $R_3$ are each independently selected from the group consisting of H, halo, OH, $NH_2$, CN, $C_{1-6}$ alkyl, $C_{1-6}$ heteroalkyl, $C_{3-6}$ cycloalkyl, $C_{3-6}$ cycloalkyl-$(CH_2)_{1-3}$— and phenyl-$(CH_2)_{1-3}$—, wherein the $C_{1-6}$ alkyl, $C_{1-6}$ heteroalkyl, $C_{3-6}$ cycloalkyl, $C_{3-6}$ cycloalkyl-$(CH_2)_{1-3}$— or phenyl-$(CH_2)_{1-3}$— is each optionally substituted with 1, 2 or 3 Rs; or $R_2$ and $R_3$ together with the carbon atom to which they are attached form a 3 to 6-membered ring;

$R_4$ is selected from the group consisting of $C_{1-6}$ alkyl and $C_{3-6}$ cycloalkyl-$(CH_2)_{1-3}$—, wherein the $C_{1-6}$ alkyl or $C_{3-6}$ cycloalkyl-$(CH_2)_{1-3}$— is each optionally substituted with 1, 2 or 3 Rs;

$R_5$ is selected from the group consisting of H and $C_{1-3}$ alkyl optionally substituted with 1, 2 or 3 Rs;

each R is independently selected from the group consisting of F, Cl, Br, I, OH, Me, $NH_2$, $NH(CH_3)$ and $N(CH_3)_2$;

wherein the prefix "hetero" in the $C_{1-3}$ heteroalkyl, $C_{1-6}$ heteroalkyl and 5 to 10-membered heteroaryl is each independently selected from the group consisting of —O—, —S—, —NH— and N; in any one of the above cases, the number of heteroatom or group containing a heteroatom is independently selected from 1, 2 or 3.

In some embodiments of the present application, n is selected from 0, 1 or 2.

In some embodiments of the present application, the prefix "hetero" in the $C_{1-3}$ heteroalkyl and $C_{1-6}$ heteroalkyl is each independently selected from the group consisting of —O—, —S— and —NH—, and the prefix "hetero" in the 5 to 10-membered heteroaryl is selected from the group consisting of N, —O— and —S—. In some embodiments of the present application, the prefix "hetero" in the $C_{1-3}$ heteroalkyl and $C_{1-6}$ heteroalkyl is —O—, and the prefix "hetero" in the 5 to 10-membered heteroaryl is selected from the group consisting of N and —S—.

In some embodiments of the present application, $R_1$ is each independently selected from the group consisting of halo, OH, $NH_2$, CN, $C_{1-3}$ alkyl, $C_{1-3}$ alkoxy, and phenyl, wherein the $C_{1-3}$ alkyl, $C_{1-3}$ alkoxy or phenyl is each optionally substituted with 1, 2 or 3 Rs; preferably, $R_1$ is each independently selected from the group consisting of halo, OH, $NH_2$, CN, $C_{1-3}$ alkoxy, phenyl and $C_{1-3}$ alkyl optionally substituted with 1, 2 or 3 substituents independently selected from the group consisting of F, Cl, Br and I; more preferably, $R_1$ is each independently selected from the group consisting of halo, OH, $NH_2$, CN, $C_{1-3}$ alkoxy, phenyl and $C_{1-3}$ alkyl optionally substituted with 1, 2 or 3 F; further more preferably, $R_1$ is each independently selected from the group consisting of halo, CN, phenyl and $C_{1-3}$ alkyl optionally substituted with 3 F; and most preferably, $R_1$ is each independently selected from the group consisting of F, Cl, CN, phenyl and methyl optionally substituted with 3 F.

In some embodiments of the present application, $R_1$ is each independently selected from the group consisting of F, Cl, Br, I, OH, $NH_2$, CN, Me,

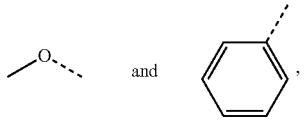

wherein the Me,

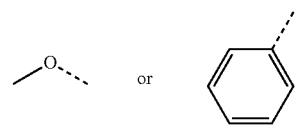

is optionally substituted with 1, 2 or 3 Rs.

In some preferred embodiments of the present application, $R_1$ is each independently selected from the group consisting of F, Cl, Br, I, CN, Me and

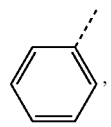

wherein the Me or

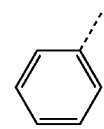

is optionally substituted with 1, 2 or 3 substituents independently selected from the group consisting of F, Cl, Br and I; preferably, $R_1$ is each independently selected from the group consisting of F, Cl, Br, I, CN,

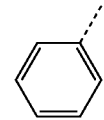

and Me optionally substituted with 1, 2 or 3 substituents independently selected from the group consisting of F, Cl, Br and I; further more preferably, $R_1$ is each independently selected from the group consisting of F, Cl, Br, I, CN,

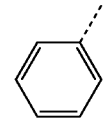

and Me optionally substituted with 1, 2 or 3 F; and most preferably, $R_1$ is each independently selected from the group consisting of F, Cl, Br, I, CN,

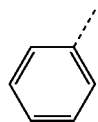

and Me optionally substituted with 3 F.

In some preferred embodiments of the present application, $R_1$ is each independently selected from the group consisting of F, Cl, Br, I, OH, $NH_2$, CN, Me, $CF_3$,

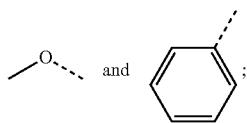

and preferably, $R_1$ is each independently selected from the group consisting of F, Cl, CN,

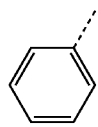

and $CF_3$.

In some embodiments of the present application, ring A is selected from the group consisting of phenyl and 5 to 10-membered heteroaryl.

In some embodiments of the present application, ring A is selected from the group consisting of cyclopropyl, phenyl, 5-membered heteroaryl, 6-membered heteroaryl, 7-membered heteroaryl, 8-membered heteroaryl, 9-membered heteroaryl and 10-membered heteroaryl; preferably, ring A is selected from the group consisting of cyclopropyl, phenyl, 5-membered heteroaryl, 6-membered heteroaryl and 9-membered heteroaryl; and more preferably, ring A is selected from the group consisting of cyclopropyl, phenyl, pyridyl, pyrimidinyl, pyrazinyl, pyridazinyl, 1,3,4-oxadiazolyl, thiazolyl, isothiazolyl, thienyl, pyrazolyl, imidazolyl and 1H-indazolyl.

In some preferred embodiments of the present application, ring A is selected from the group consisting of cyclopropyl, phenyl, pyridyl, pyrimidinyl, thiazolyl and pyridazinyl; and more preferably, ring A is selected from the group consisting of phenyl, pyridyl, pyrimidinyl, thiazolyl and pyridazinyl.

In some preferred embodiments of the present application, ring A is selected from the group consisting of phenyl, pyridyl, pyrimidinyl, pyrazinyl, 1,3,4-oxadiazolyl, thiazolyl, imidazolyl and 1H-indazolyl; preferably, ring A is selected from the group consisting of phenyl, pyridyl and pyrimidinyl; and more preferably, ring A is selected from phenyl.

In some embodiments of the present application, the structural unit

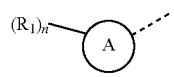

in the compound of Formula (I) is selected from the group consisting of

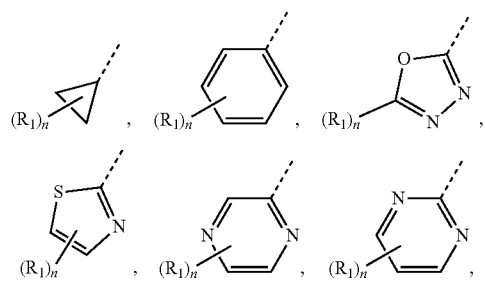

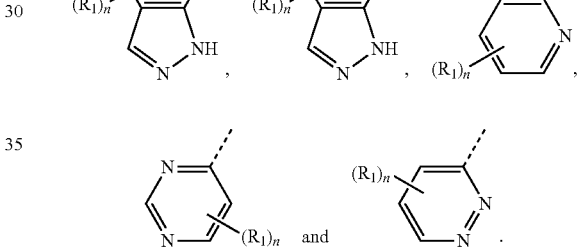

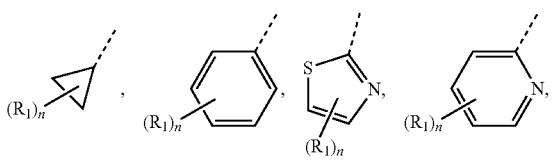

In some preferred embodiments of the present application, the structural unit

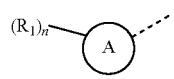

is selected from the group consisting of

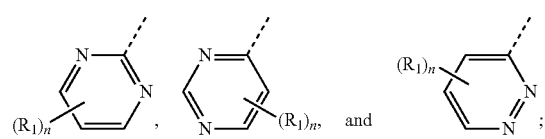

and more preferably, the structural unit

is selected from the group consisting of

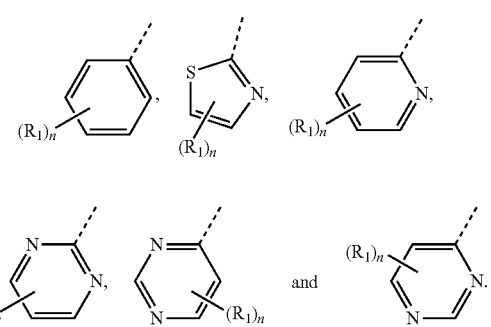

In some preferred embodiments of the present application, the structural unit

is selected from the group consisting of

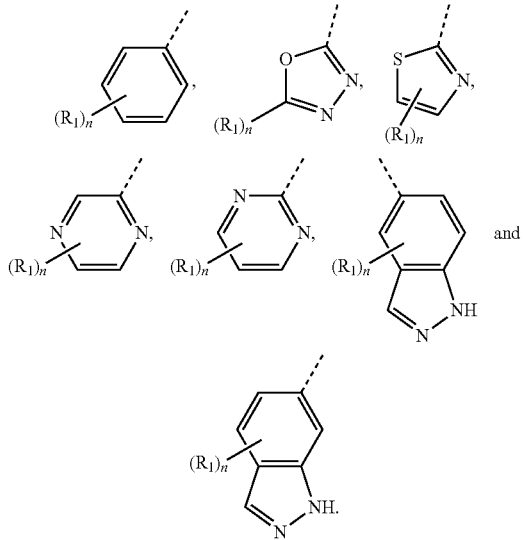

In some specific embodiments of the present application, the structural unit

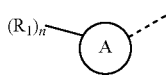

is selected from

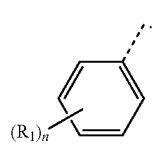

In some more preferred embodiments of the present application, the structural unit

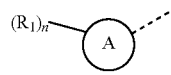

is selected from the group consisting of

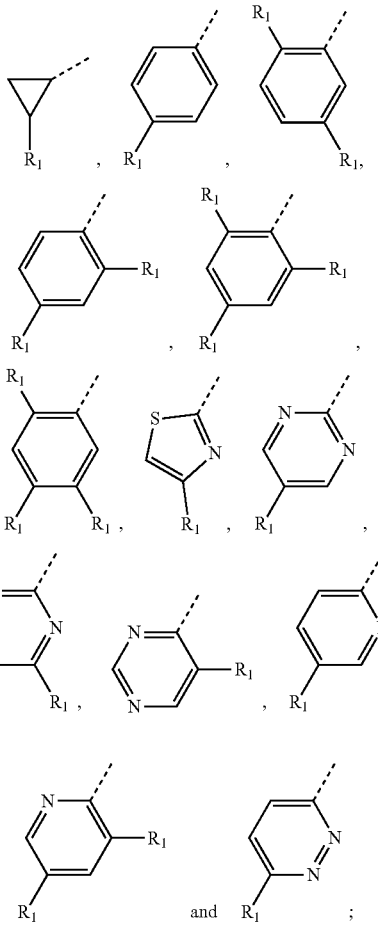

further more preferably, the structural unit

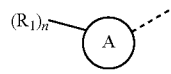

is selected from the group consisting of

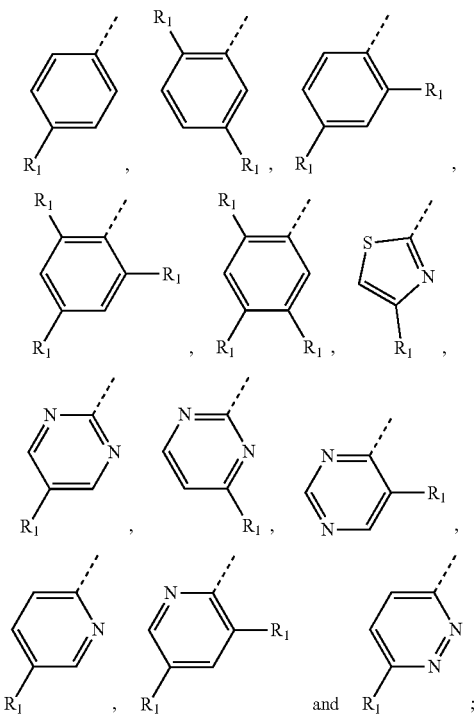

and most preferably, the structural unit is

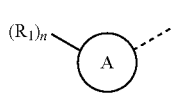

selected from the group consisting of

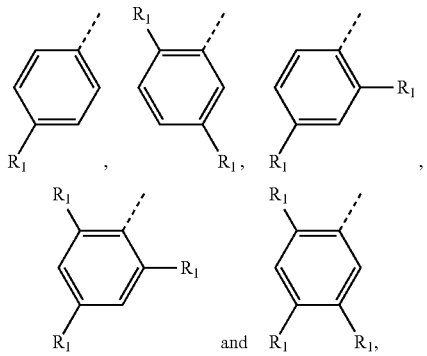

In some more preferred embodiments of the present application, the structural unit

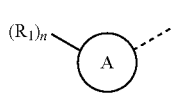

is selected from the group consisting of

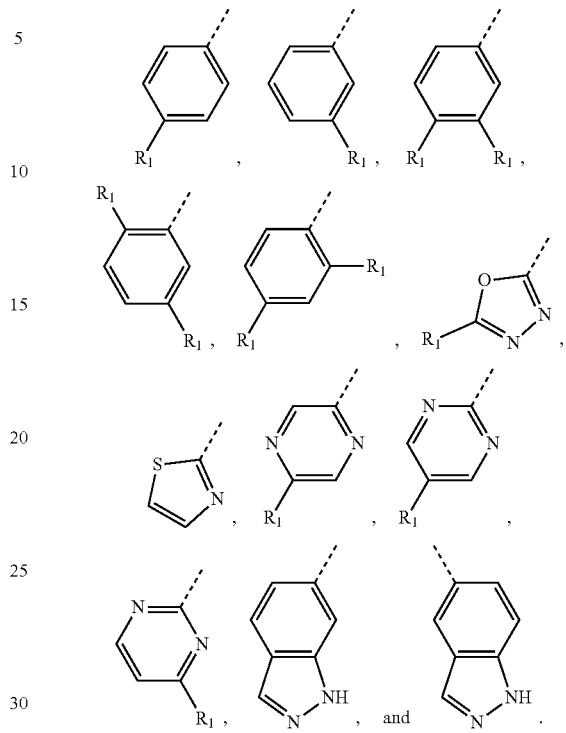

In some specific embodiments of the present application, the structural unit

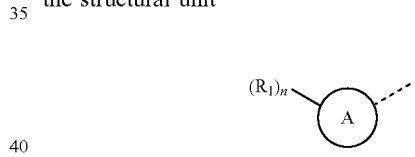

is selected from the group consisting of

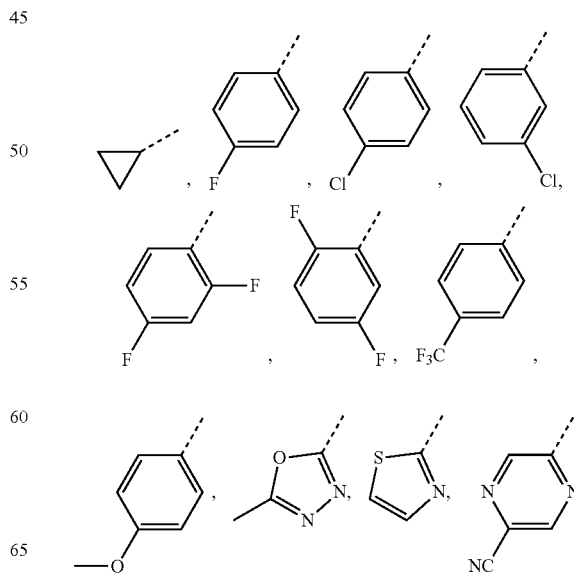

-continued
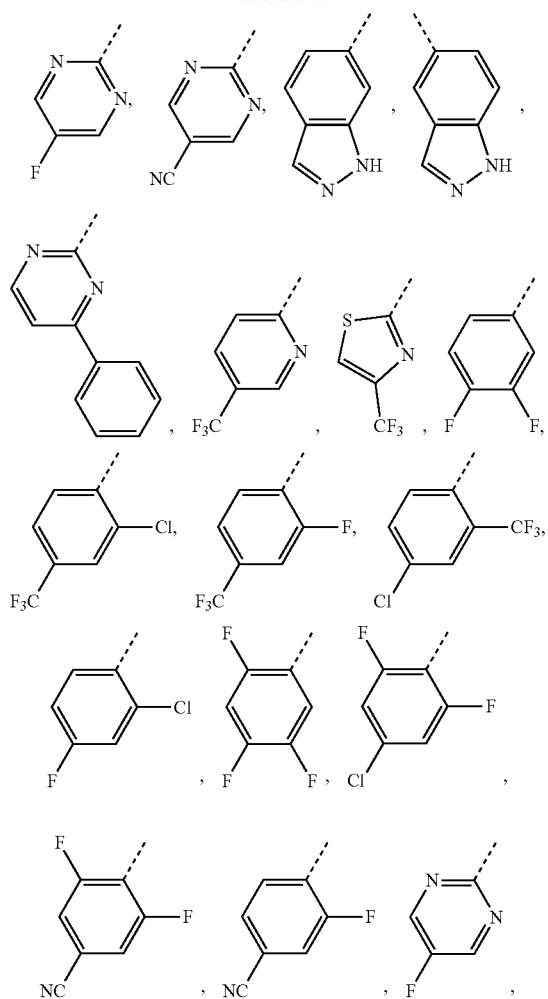
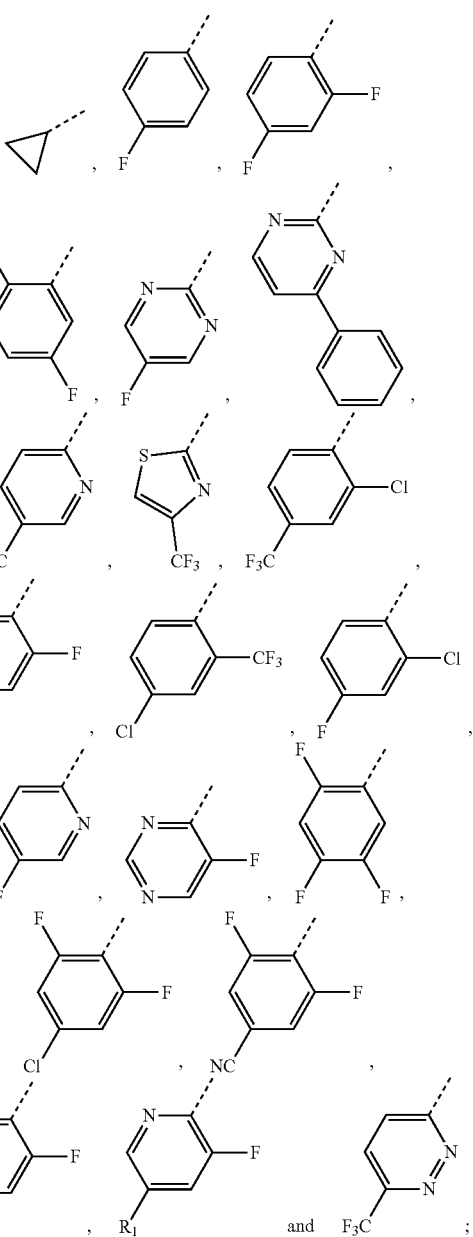
In some preferred specific embodiments of the present application, the structural unit
is selected from the group consisting of
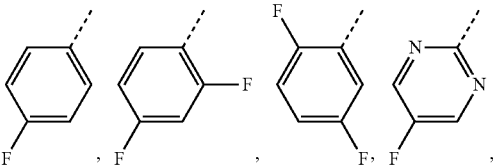
more preferably, the structural unit
is selected from the group consisting of -continued
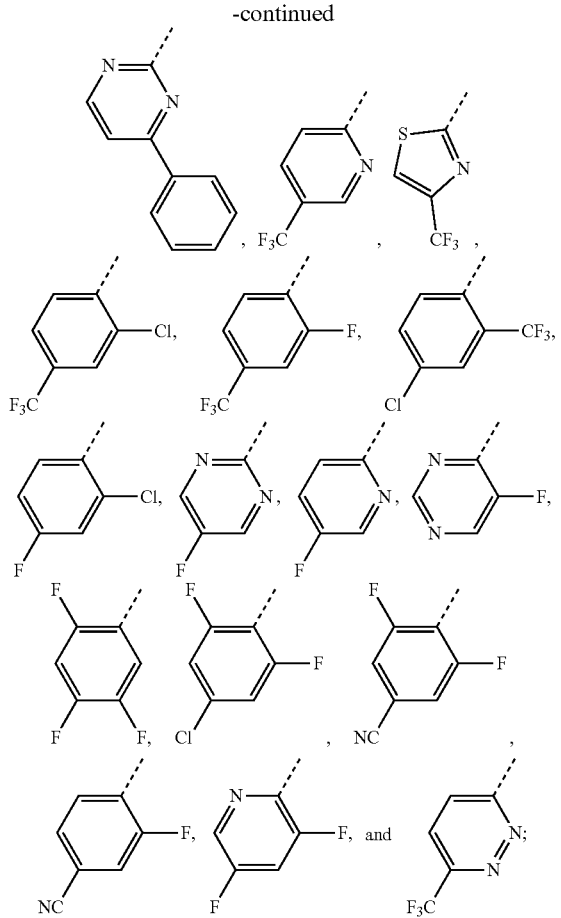
and further more preferably, the structural unit
is selected from the group consisting of
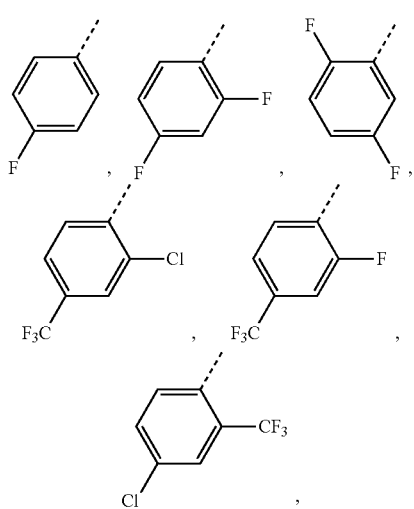
-continued
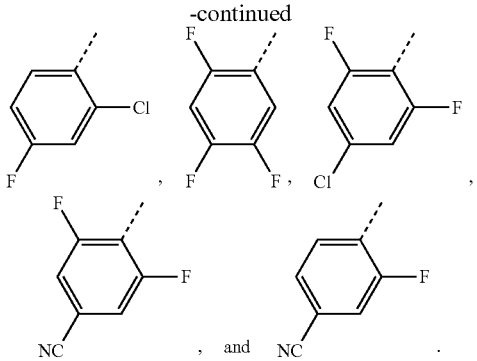
In some preferred specific embodiments of the present application, the structural unit
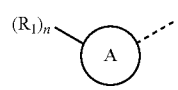
is selected from the group consisting of
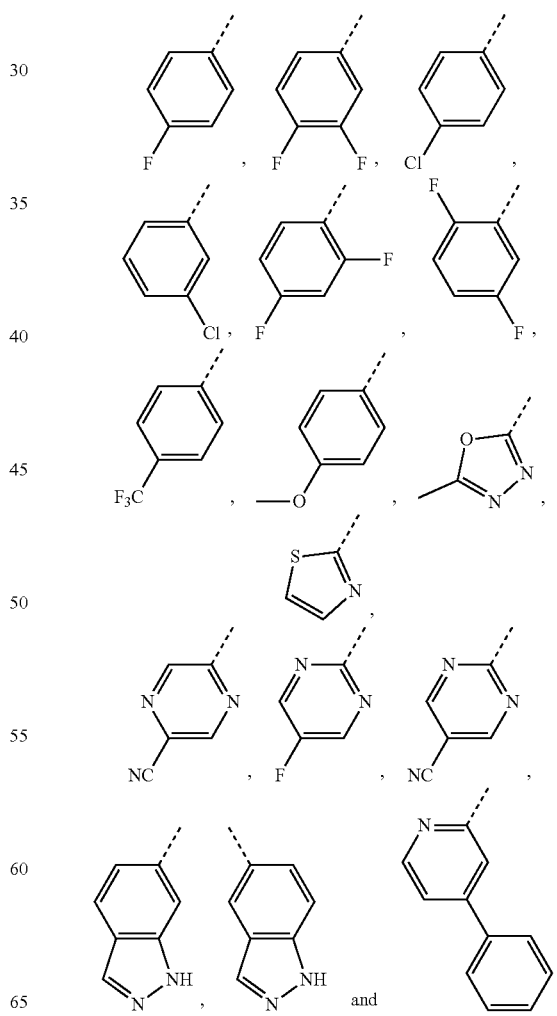

In some embodiments of the present application, $R_2$ and $R_3$ are each independently selected from the group consisting of H, halo, OH, $NH_2$, CN, $C_{1-6}$ alkyl, $C_{1-3}$ alkoxy, $C_{1-3}$ alkyl-O—$C_{1-3}$ alkyl-, $C_{3-6}$ cycloalkyl-$CH_2$— and phenyl-$CH_2$—, wherein the $C_{1-6}$ alkyl, $C_{1-3}$ alkoxy, $C_{1-3}$ alkyl-O—$C_{1-3}$ alkyl-, $C_{3-6}$ cycloalkyl-$CH_2$— or phenyl-$CH_2$— is each optionally substituted with 1, 2 or 3 Rs; or $R_2$ and $R_3$ together with the carbon atom to which they are attached form a 3 to 6-membered cycloalkyl; preferably, $R_2$ and $R_3$ are each independently selected from the group consisting of H, $C_{1-6}$ alkyl, $C_{1-3}$ alkoxy, $C_{1-3}$ alkyl-O—$C_{1-3}$ alkyl-, $C_{3-6}$ cycloalkyl-$CH_2$— and phenyl-$CH_2$—, wherein the $C_{1-6}$ alkyl, $C_{1-3}$ alkoxy, $C_{1-3}$ alkyl-O—$C_{1-3}$ alkyl-, $C_{3-6}$ cycloalkyl-$CH_2$— or phenyl-$CH_2$— is each optionally substituted with 1, 2 or 3 substituents independently selected from the group consisting of F, Cl, Br, I and hydroxyl; more preferably, $R_2$ and $R_3$ are each independently selected from the group consisting of H, $C_{1-6}$ alkyl, $C_{1-3}$ alkoxy, $C_{3-6}$ cycloalkyl-$CH_2$— and phenyl-$CH_2$—; further more preferably, $R_2$ and $R_3$ are each independently selected from the group consisting of H, $C_{1-6}$ alkyl, $C_{3-6}$ cycloalkyl-$CH_2$— and phenyl-$CH_2$—; and most preferably, $R_2$ and $R_3$ are each independently selected from the group consisting of H, Me,

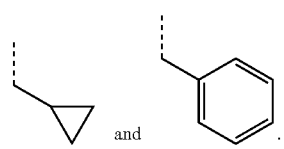

In some preferred embodiments of the present application, $R_3$ is H, and $R_2$ is selected from the group consisting of H, halo, OH, $NH_2$, CN, $C_{1-6}$ alkyl, $C_{1-3}$ alkoxy, $C_{1-3}$ alkyl-O—$C_{1-3}$ alkyl-, $C_{3-6}$ cycloalkyl-$CH_2$— and phenyl-$CH_2$—, wherein the $C_{1-6}$ alkyl, $C_{1-3}$ alkoxy, $C_{1-3}$ alkyl-O—$C_{1-3}$ alkyl-, $C_{3-6}$ cycloalkyl-$CH_2$— or phenyl-$CH_2$— is each optionally substituted with 1, 2 or 3 Rs; preferably, the above-mentioned $R_3$ is H, and $R_2$ is selected from the group consisting of H, $C_{1-6}$ alkyl, $C_{1-3}$ alkoxy, $C_{1-3}$ alkyl-O—$C_{1-3}$ alkyl-, $C_{3-6}$ cycloalkyl-$CH_2$— and phenyl-$CH_2$—, wherein the $C_{1-6}$ alkyl, $C_{1-3}$ alkoxy, $C_{1-3}$ alkyl-O—$C_{1-3}$ alkyl-, $C_{3-6}$ cycloalkyl-$CH_2$— or phenyl-$CH_2$— is each optionally substituted with 1, 2 or 3 substituents independently selected from the group consisting of F, Cl, Br, I and hydroxyl; more preferably, the above-mentioned $R_3$ is H, and $R_2$ is selected from the group consisting of H, $C_{1-6}$ alkyl, $C_{1-3}$ alkoxy, $C_{3-6}$ cycloalkyl-$CH_2$— and phenyl-$CH_2$—; more preferably, $R_3$ is H, and $R_2$ is selected from the group consisting of H, $C_{1-6}$ alkyl, $C_{3-6}$ cycloalkyl-$CH_2$— and phenyl-$CH_2$—; and most preferably, $R_3$ is H, and $R_2$ is selected from the group consisting of H, Me,

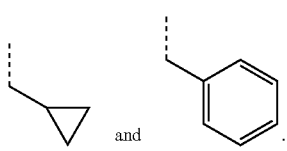

In some embodiments of the present application, $R_2$ and $R_3$ are each independently selected from the group consisting of H, F, Cl, Br, I, OH, $NH_2$, CN, Me, Et,

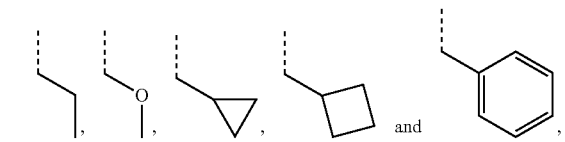

wherein Me, Et,

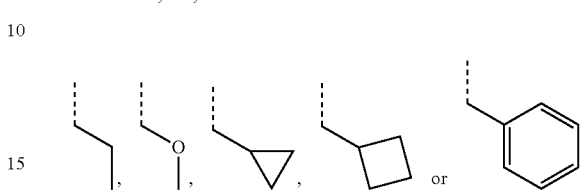

is optionally substituted with 1, 2 or 3 Rs.

In some embodiments of the present application, $R_2$ and $R_3$ are each independently selected from the group consisting of H, Me,

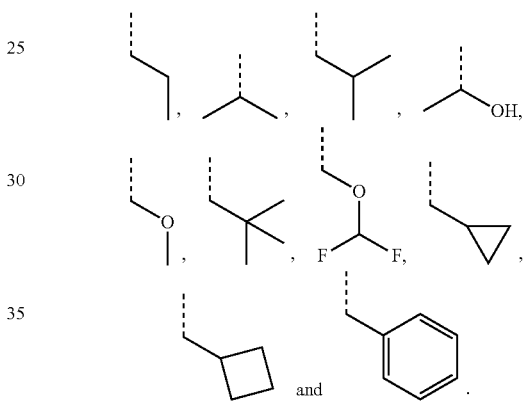

In some specific embodiments of the present application, $R_2$ is selected from the group consisting of H, Me,

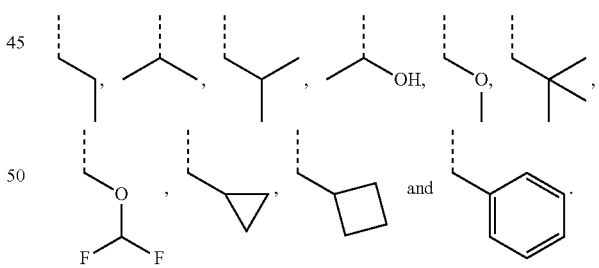

and $R_3$ is H.

In some embodiments of the present application, $R_2$ and $R_3$ together with the carbon atom to which they are attached form a 3 to 6-membered cycloalkyl.

In some embodiments of the present application, the structural unit

is

In some embodiments of the present application, $R_4$ is selected from the group consisting of $C_{1-6}$ alkyl and $C_{3-6}$ cycloalkyl-$CH_2$—, wherein the $C_{1-6}$ alkyl or $C_{3-6}$ cycloalkyl-$CH_2$— is each optionally substituted with 1, 2 or 3 Rs; preferably, $R_4$ is selected from the group consisting of $C_{1-6}$ alkyl and $C_{3-6}$ cycloalkyl-$CH_2$—; more preferably, $R_4$ is selected from the group consisting of $C_{1-4}$ alkyl and $C_{3-6}$ cycloalkyl-$CH_2$—; further more preferably, $R_4$ is selected from the group consisting of $C_{3-4}$ alkyl and $C_{3-4}$ cycloalkyl-$CH_2$—; and most preferably, $R_4$ is selected from the group consisting of $C_4$ alkyl and $C_4$ cycloalkyl-$CH_2$—.

In some embodiments of the present application, $R_4$ is selected from the group consisting of

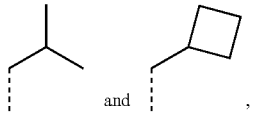

wherein

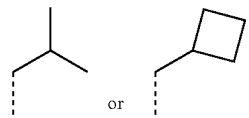

is each optionally substituted with 1, 2 or 3 Rs; preferably, $R_4$ is selected from the group consisting of

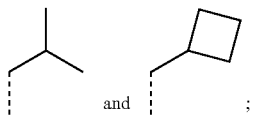

and more preferably, $R_4$ is

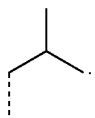

In some embodiments of the present application, $R_5$ is selected from the group consisting of H and $C_{1-3}$ alkyl; preferably, $R_5$ is selected from the group consisting of H, Me and Et; more preferably, $R_5$ is selected from the group consisting of H and Me; and most preferably, $R_5$ is H.

In some embodiments of the present application, each R is independently selected from the group consisting of F, Cl, Br, I, OH, Me and $NH_2$; preferably, each R is independently selected from the group consisting of F, Cl, Br, OH and Me; and more preferably, each R is independently selected from the group consisting of F and OH.

It should be understood that the above-mentioned variables n, R, $R_1$, $R_2$, $R_3$, $R_4$, $R_5$ and ring A in the present application may be combined in any manner to form a plurality of embodiments; and the above-mentioned variables R, $R_2$, $R_3$, $R_4$, $R_5$ and the structural unit

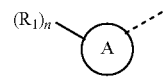

may also be combined in any manner to form a plurality of embodiments.

In some embodiments of the present application, the compound of Formula (I) is selected from the group consisting of

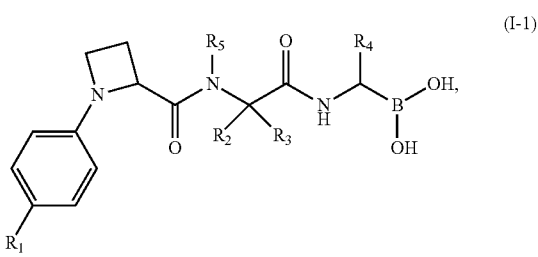
(I-1)

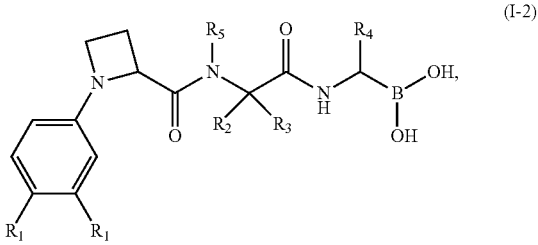
(I-2)

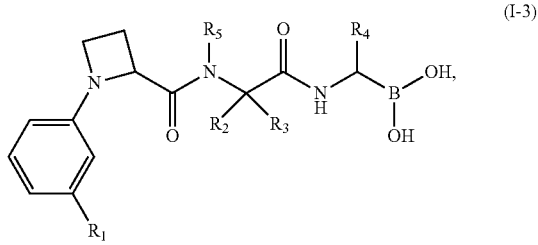
(I-3)

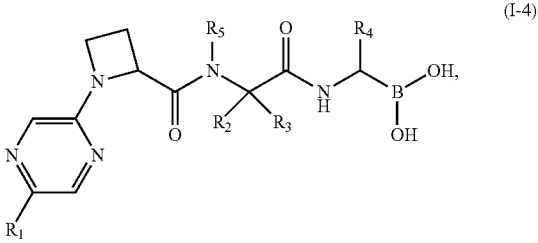
(I-4)

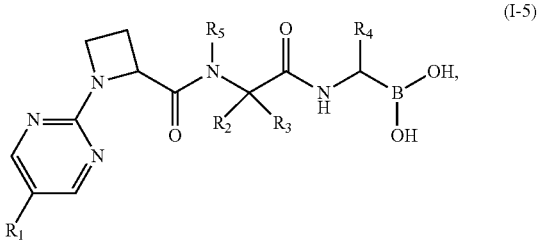
(I-5)

-continued
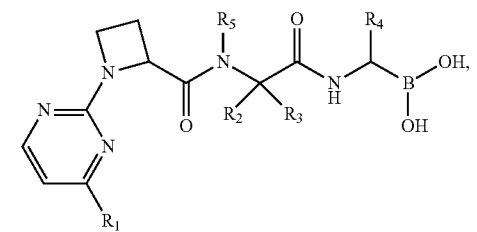
(I-6)
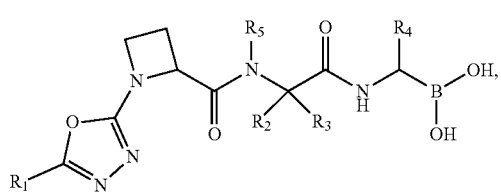
(I-7)
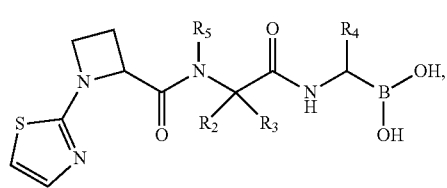
(I-8)
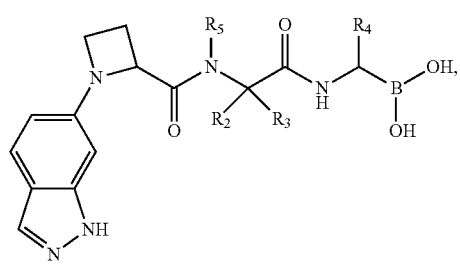
(I-9)
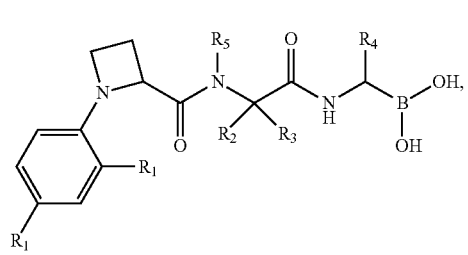
(I-10)
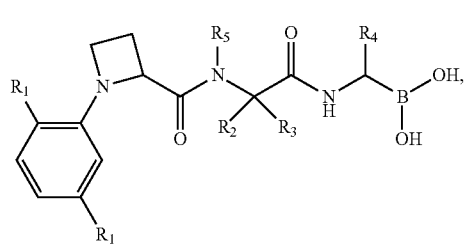
(I-11)
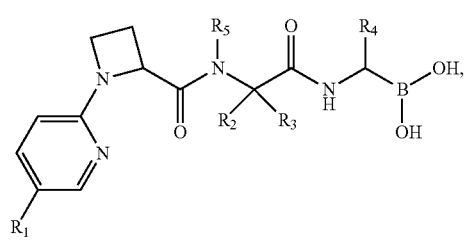
(I-12)
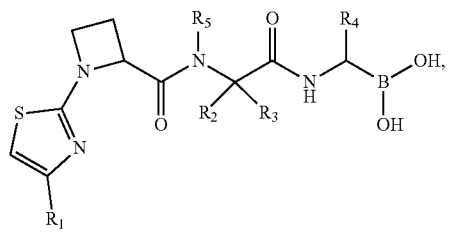
(I-13)
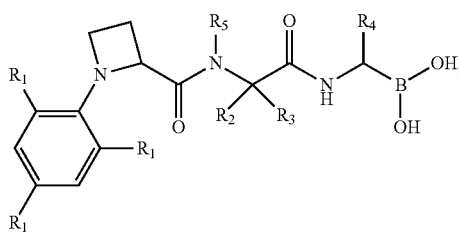
(I-14)
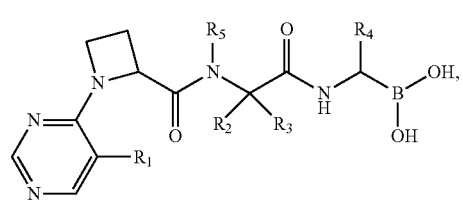
(I-15)
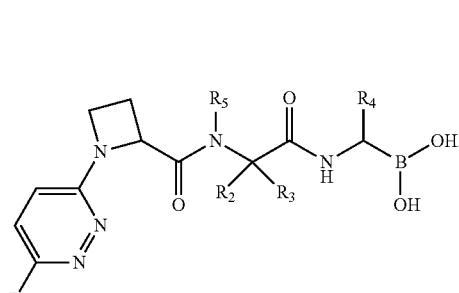
(I-16)
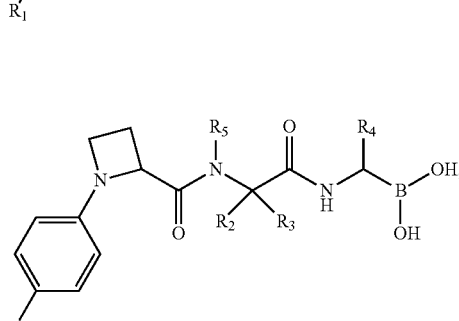
(I-17)
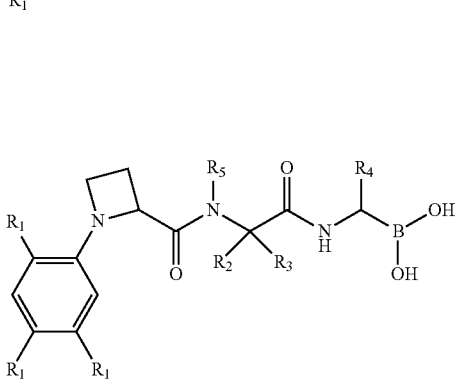
(I-18)
and -continued (I-19)

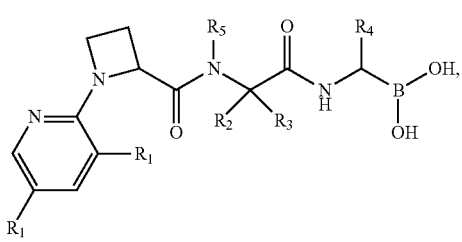

or a pharmaceutically acceptable salt, a tautomer, a stereoisomer or a geometric isomer thereof, wherein, $R_1$, $R_2$, $R_3$, $R_4$ and $R_5$ are as defined above.

The present application also provides a compound of Formula (II), a pharmaceutically acceptable salt, a tautomer, a stereoisomer or a geometric isomer thereof, (II)

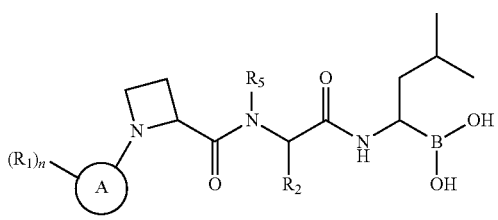

wherein, ring A, n, $R_1$, $R_2$ and $R_5$ are as defined above.

In some embodiments, the structural unit

is as defined above.

The present application also provides a compound of Formula (III) or a compound of Formula (IV), a pharmaceutically acceptable salt, a tautomer, a stereoisomer or a geometric isomer thereof, (III)

(IV)

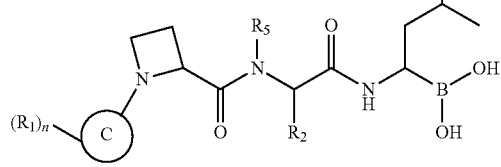

wherein, n, $R_1$, $R_2$ and $R_5$ are as defined above; and ring C is selected from the group consisting of cyclopropyl, 5-membered heteroaryl and 6-membered heteroaryl.

The present application also provides a compound of Formula (V) or a compound of Formula (VI), a pharmaceutically acceptable salt, a tautomer, a stereoisomer or a geometric isomer thereof, (V)

(VI)

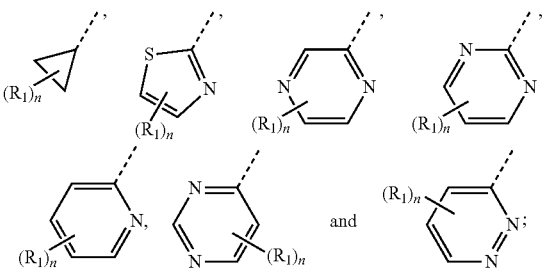

wherein n, $R_1$, $R_2$ and ring C are as defined above.

In some embodiments of the present application, ring C in the compound of Formula (IV) or the compound of Formula (VI) is selected from the group consisting of cyclopropyl, pyridyl, pyrimidinyl, pyrazinyl, pyridazinyl, 1,3,4-oxadiazolyl, thiazolyl, isothiazolyl, thienyl, pyrazolyl and imidazolyl; preferably, ring C is selected from the group consisting of cyclopropyl, pyridyl, pyrimidinyl, thiazolyl and pyridazinyl; and more preferably, ring C is selected from the group consisting of pyridinyl, pyrimidinyl, thiazolyl and pyridazinyl.

In some embodiments of the present application, the structural unit

in the compound of Formula (IV) or the compound of Formula (VI) is selected from the group consisting of preferably, the structural unit

is selected from the group consisting of

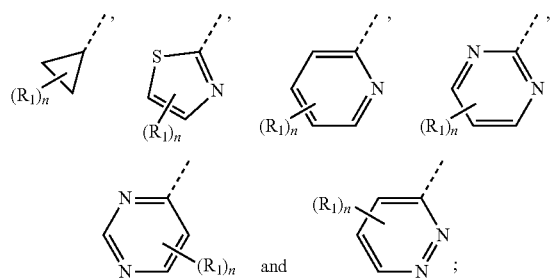

more preferably, the structural unit

is selected from the group consisting of

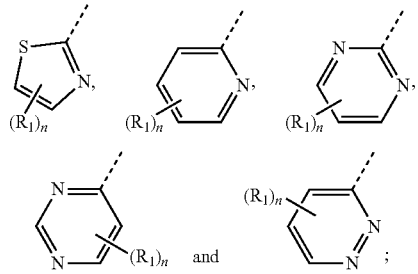

and most preferably, the structural unit

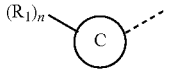

is selected from the group consisting of

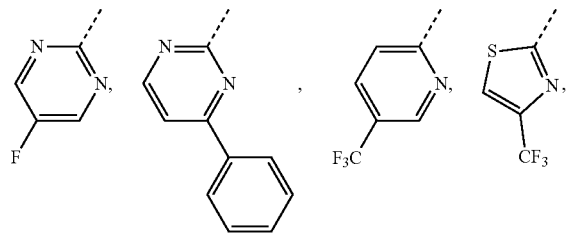

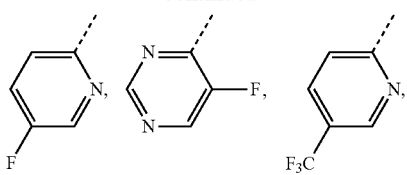

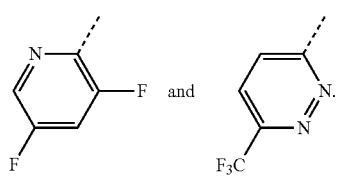

The present application also provides a compound of Formula (I-a) or a compound of Formula (I-b), a pharmaceutically acceptable salt, a stereoisomer or a geometric isomer thereof,

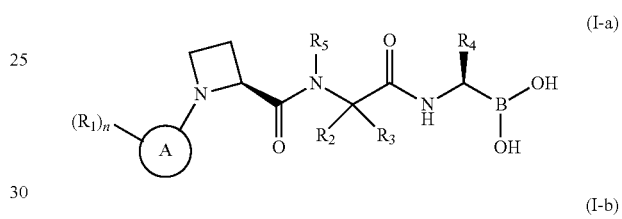

(I-a)

(I-b)

wherein ring A, n, $R_1$, $R_2$, $R_3$, $R_4$ and $R_5$ are as defined above.

In some embodiments, the structural unit

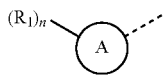

is as defined above.

The present application also provides a compound of Formula (II-a) or a compound of Formula (II-b), a pharmaceutically acceptable salt, a stereoisomer or a geometric isomer thereof, (II-a)

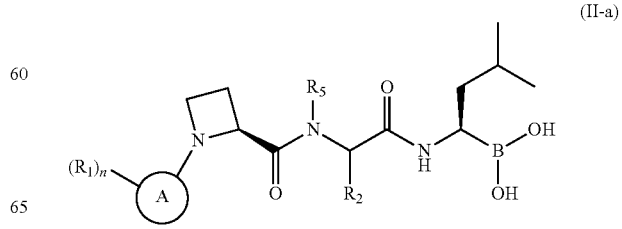

(II-b)

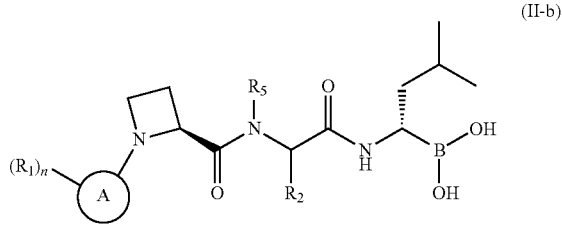

wherein ring A, n, $R_1$, $R_2$ and $R_5$ are as defined above.
In some embodiments, the structural unit

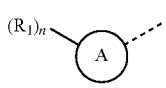

is as defined above.

The present application also provides a compound of Formula (III-a), Formula (III-b), Formula (IV-a) or Formula (IV-b), a pharmaceutically acceptable salt, a stereoisomer or a geometric isomer thereof, (III-a)

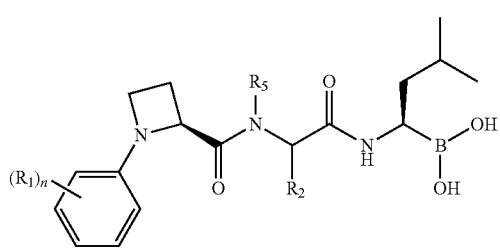

(III-b)

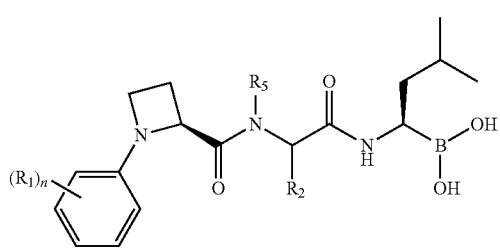

(IV-a)

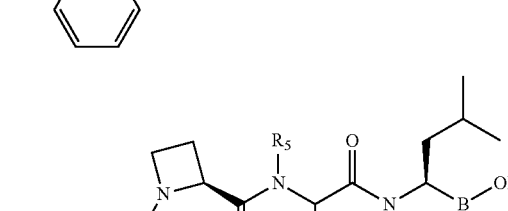

(IV-b)

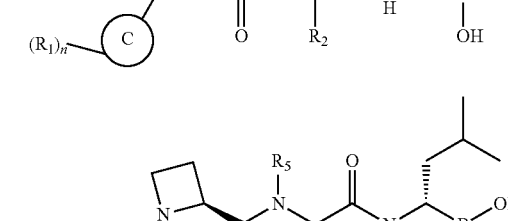

wherein n, $R_1$, $R_2$, $R_5$ and ring C are as defined above.

In some embodiments, the structural unit

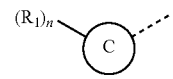

is as defined above.

The present application also provides a compound of Formula (V-a), Formula (V-b), Formula (VI-a) or Formula (VI-b), a pharmaceutically acceptable salt, a stereoisomer or a geometric isomer thereof, (V-a)

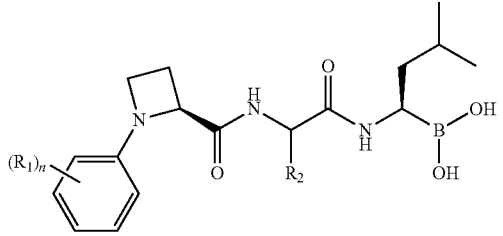

(V-b)

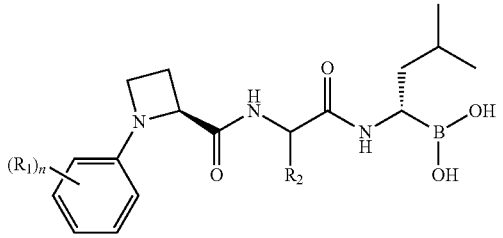

(VI-a)

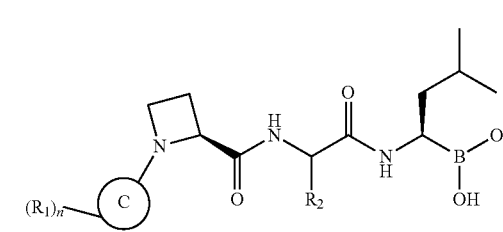

(VI-b)

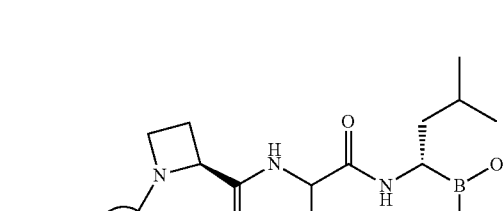

wherein n, $R_1$, $R_2$ and ring C are as defined above.
In some embodiments, the structural unit

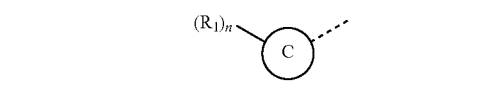

is as defined above.

The application also provides a compound selected from the following structures, a pharmaceutically acceptable salt, a tautomer, a stereoisomer or a geometric isomer thereof,
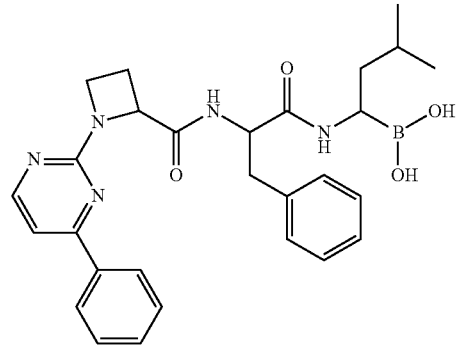
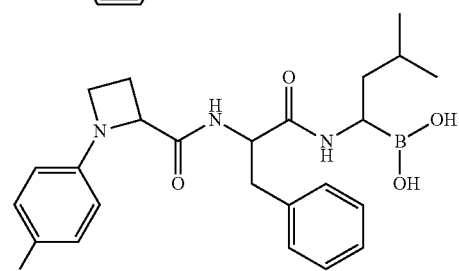
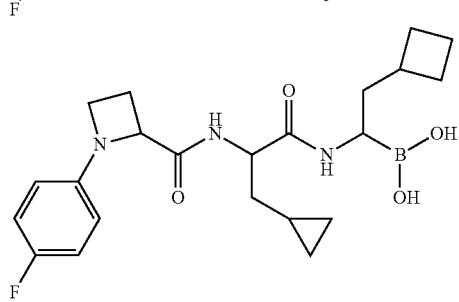
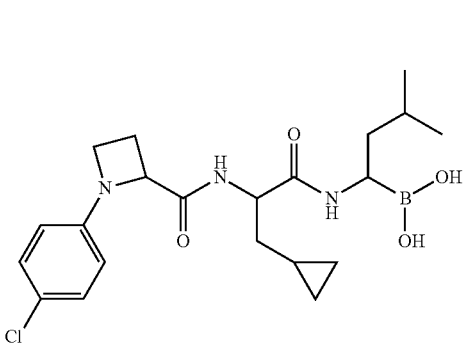
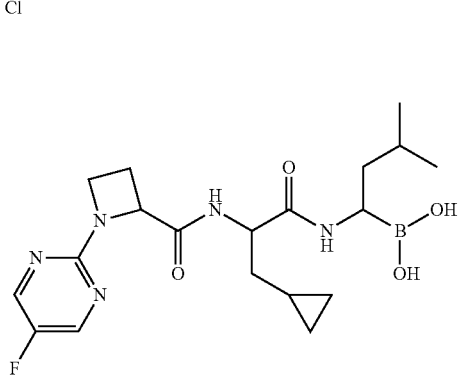
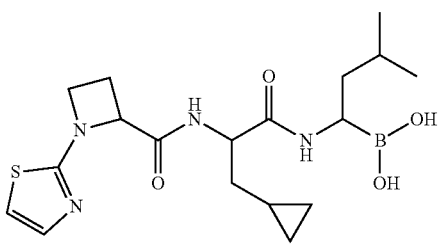
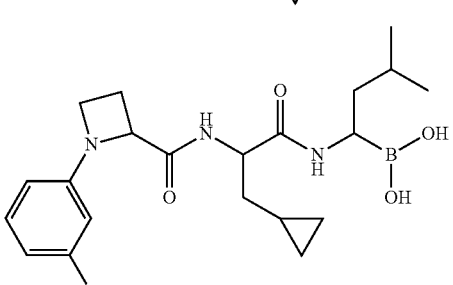
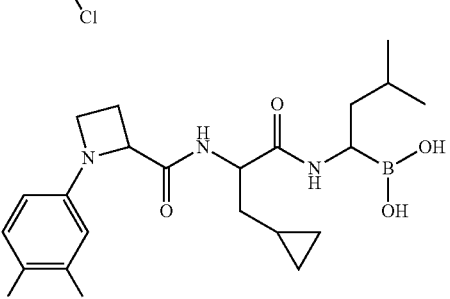
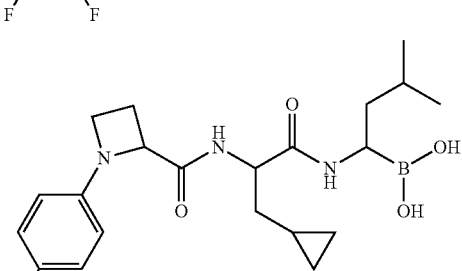
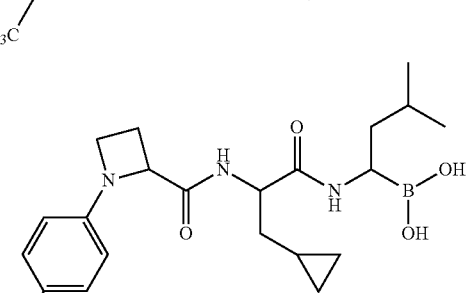
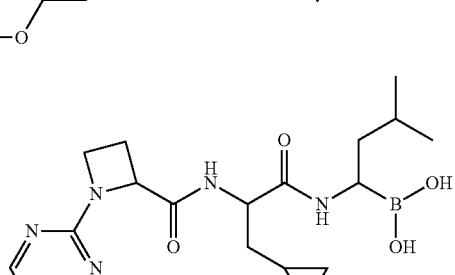

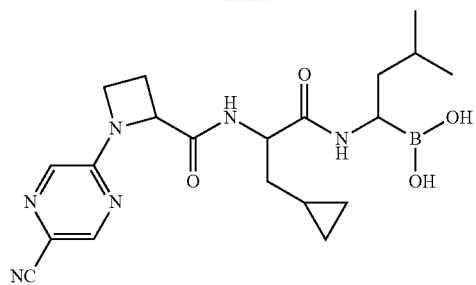
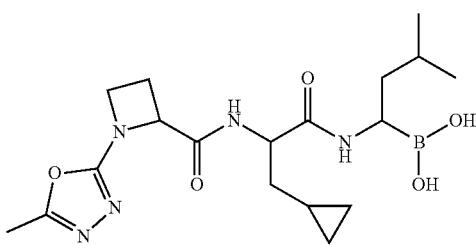
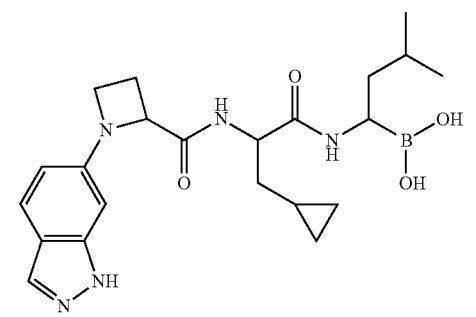
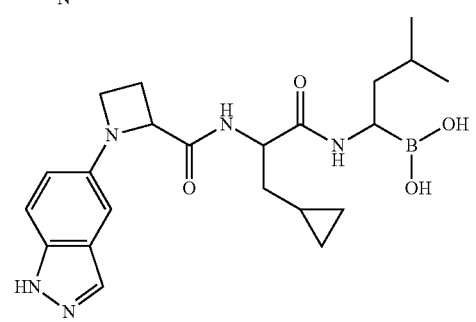
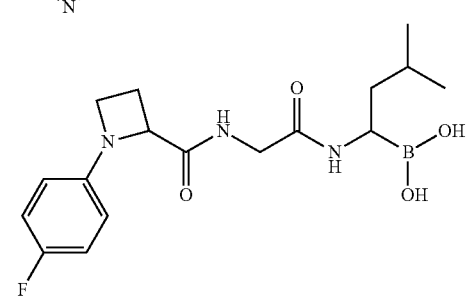
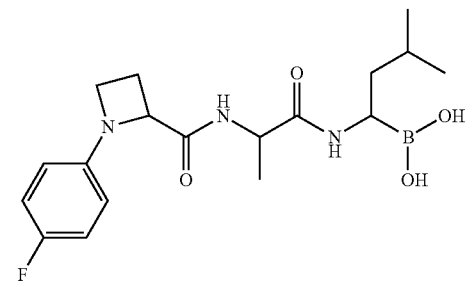
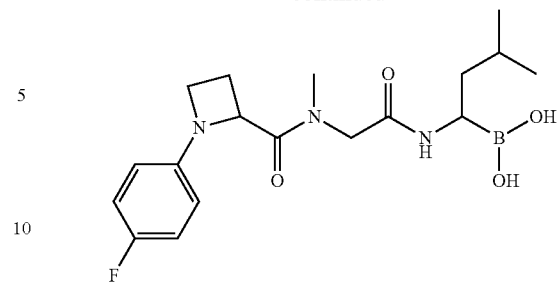
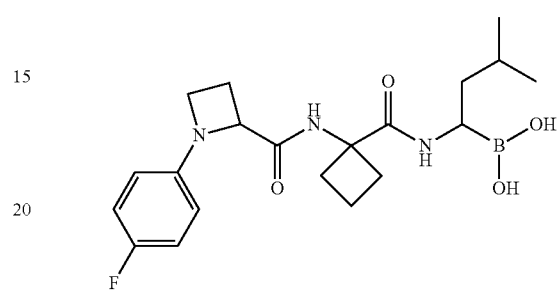
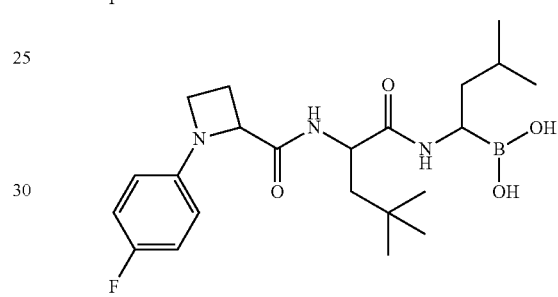
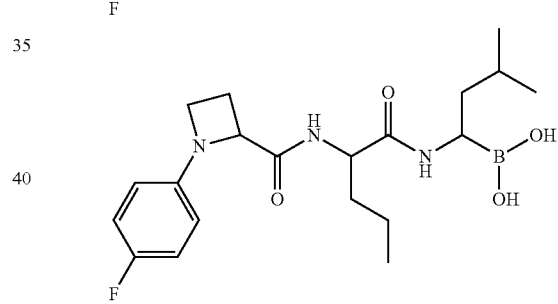
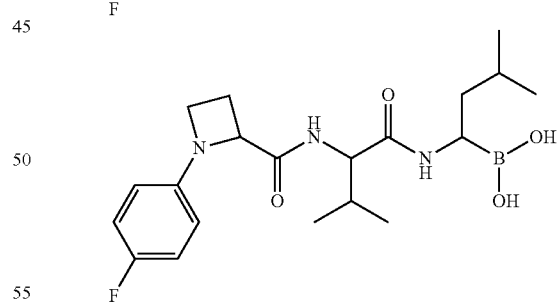
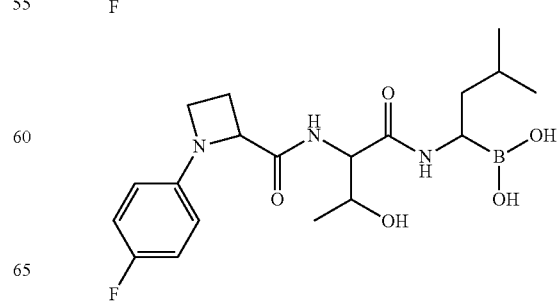

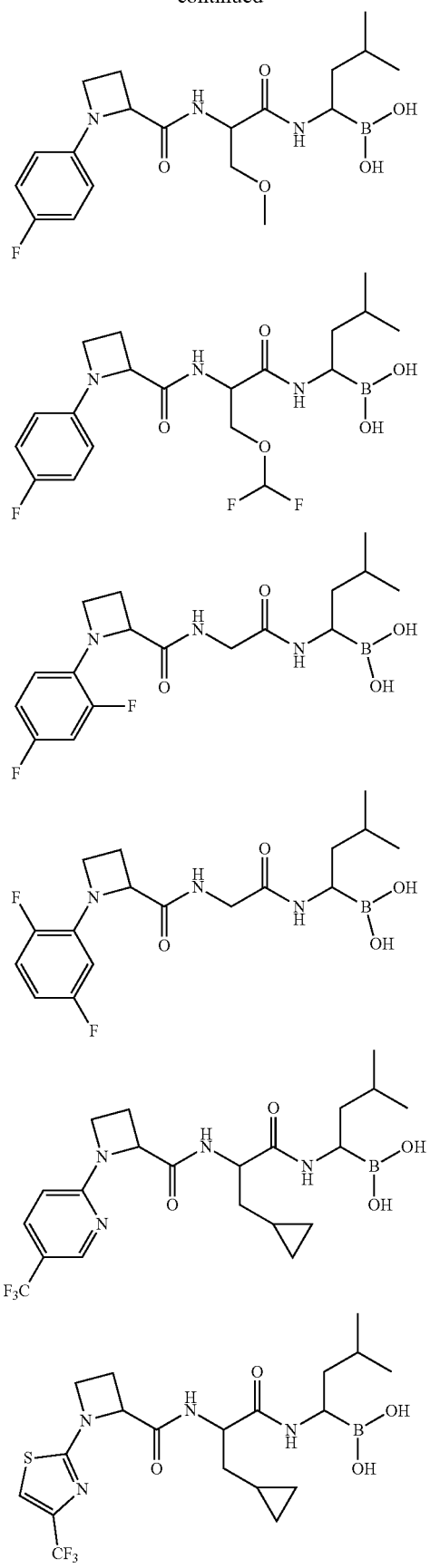
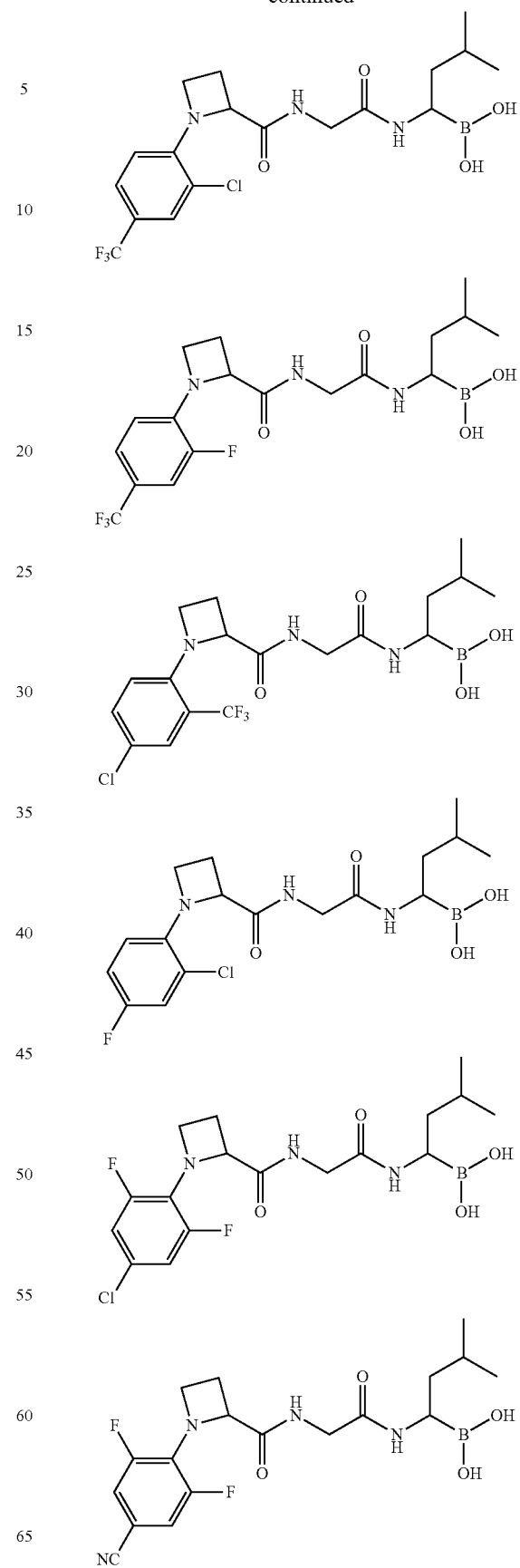

33
-continued
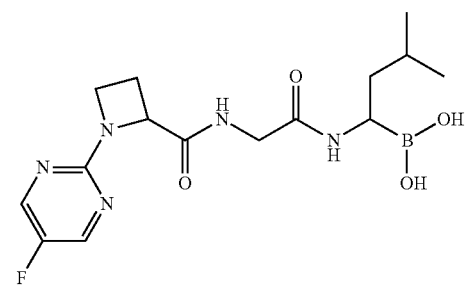
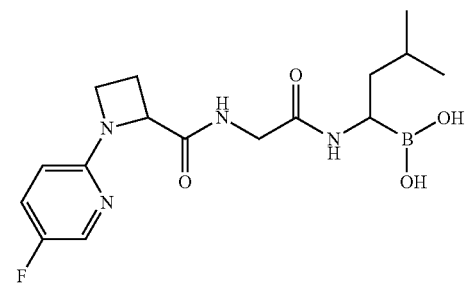
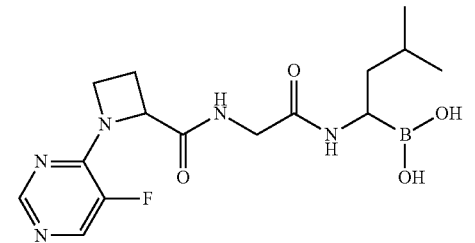
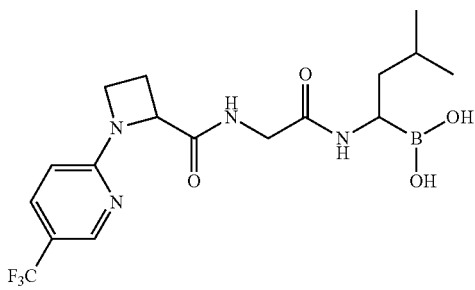
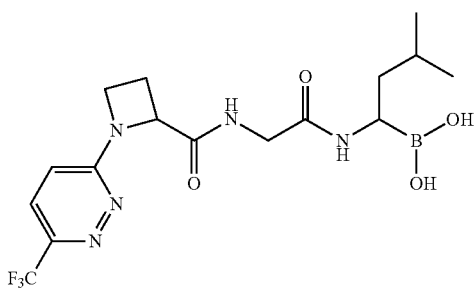
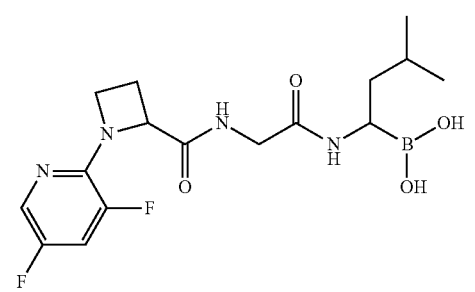
34
-continued
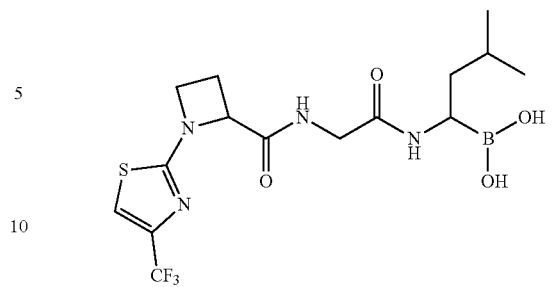
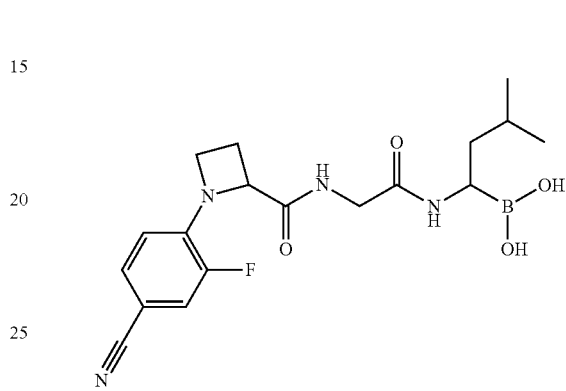
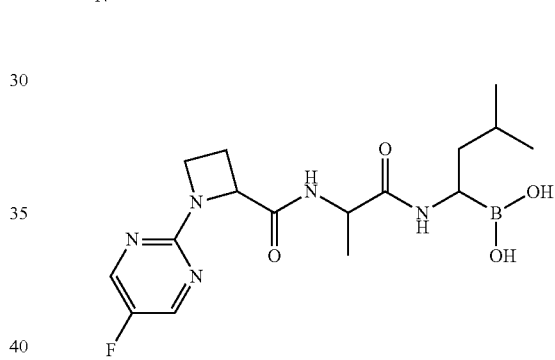
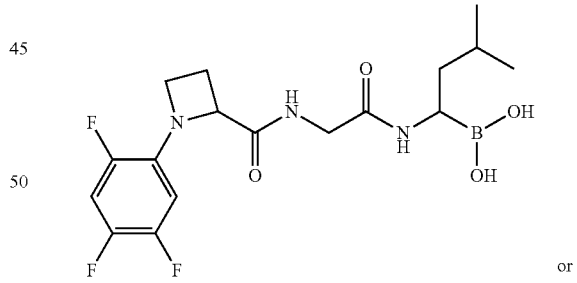
or
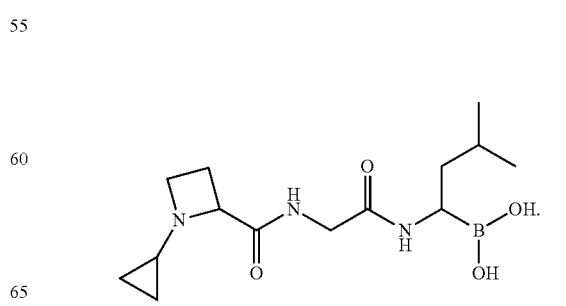

In some embodiments of the present application, the compound of Formula (I) is selected from the group consisting of
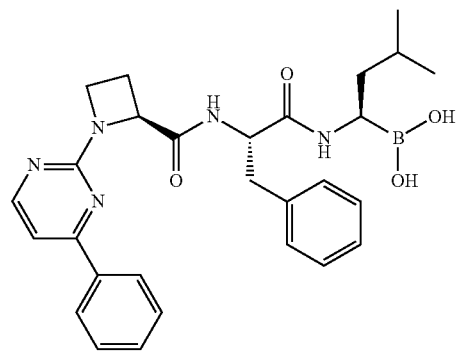
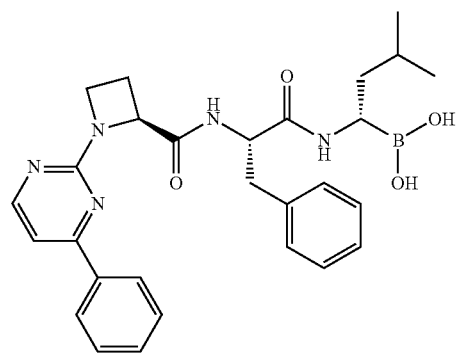
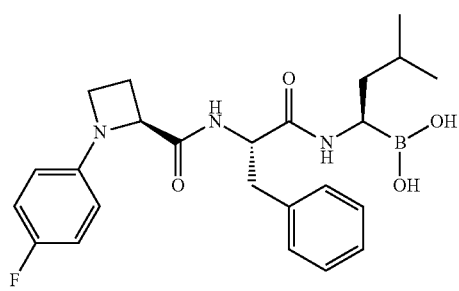
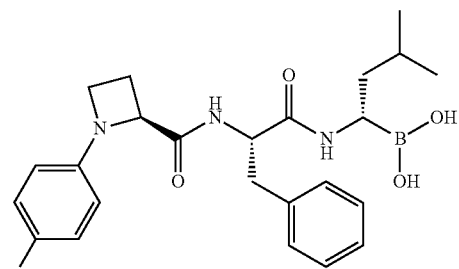
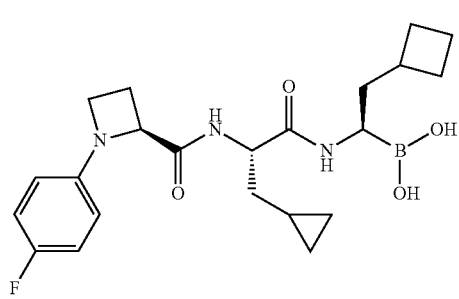
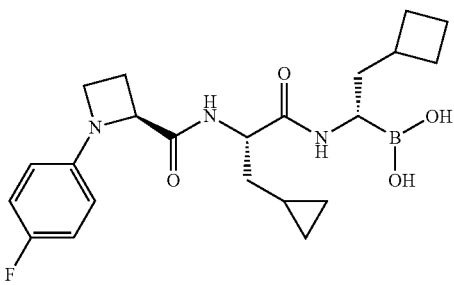
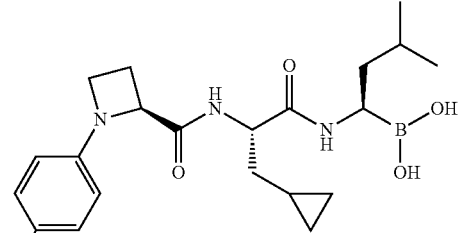
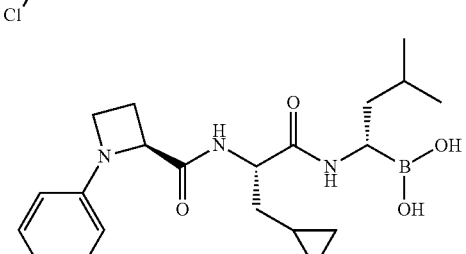
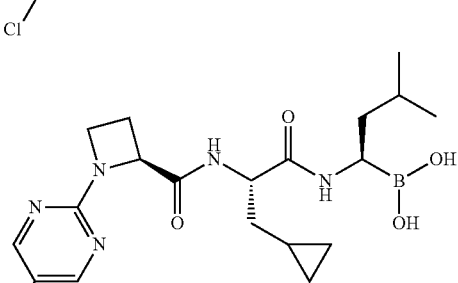
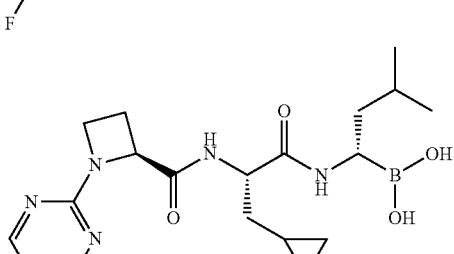
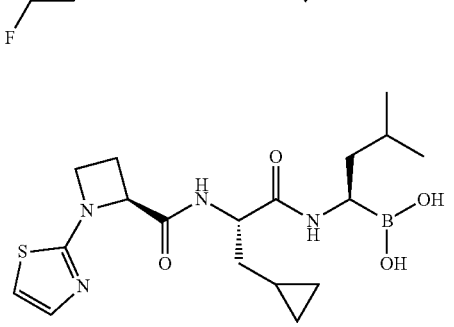

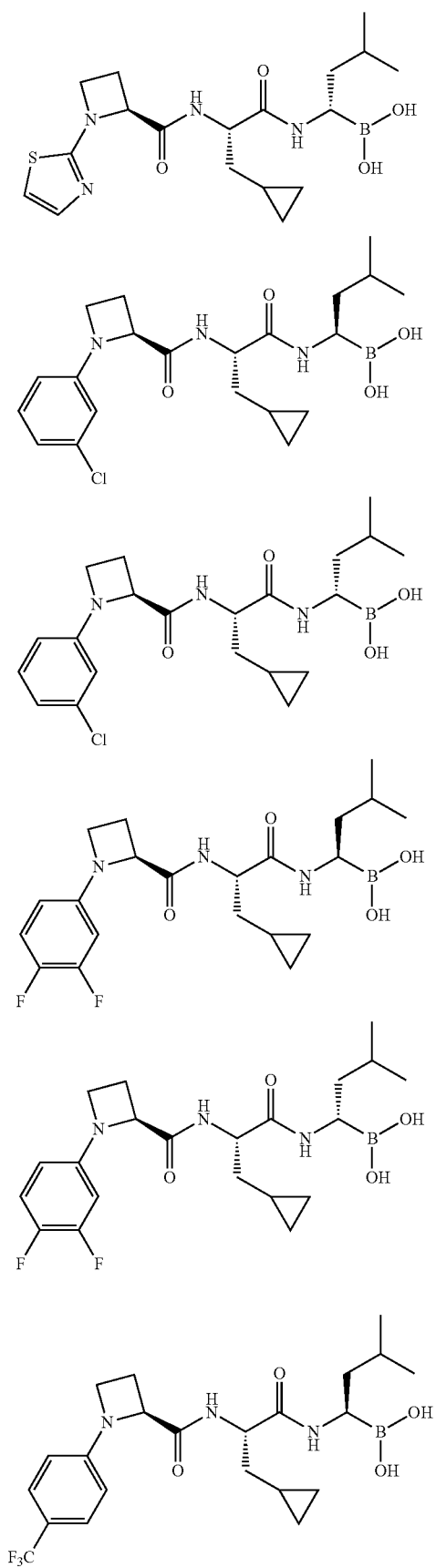
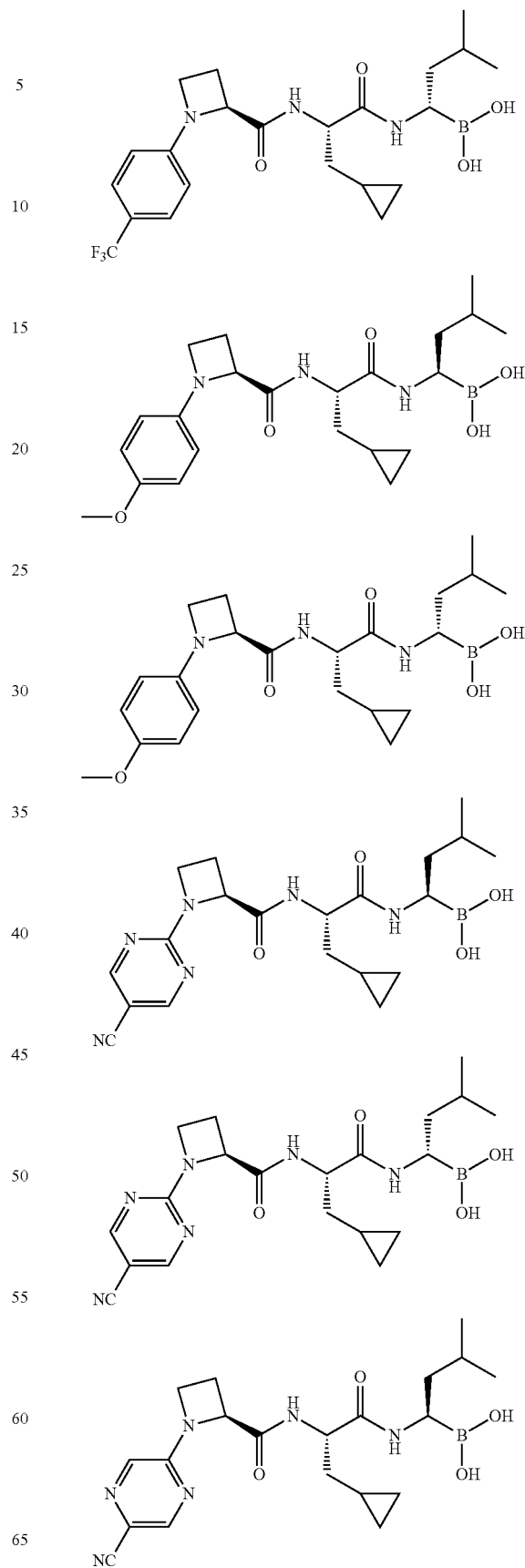

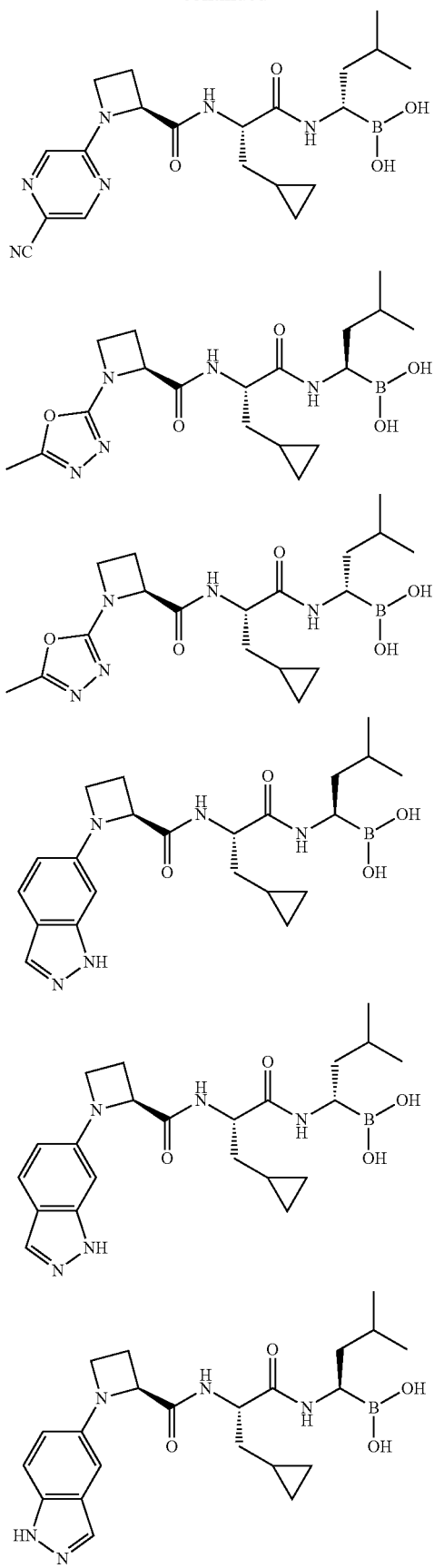
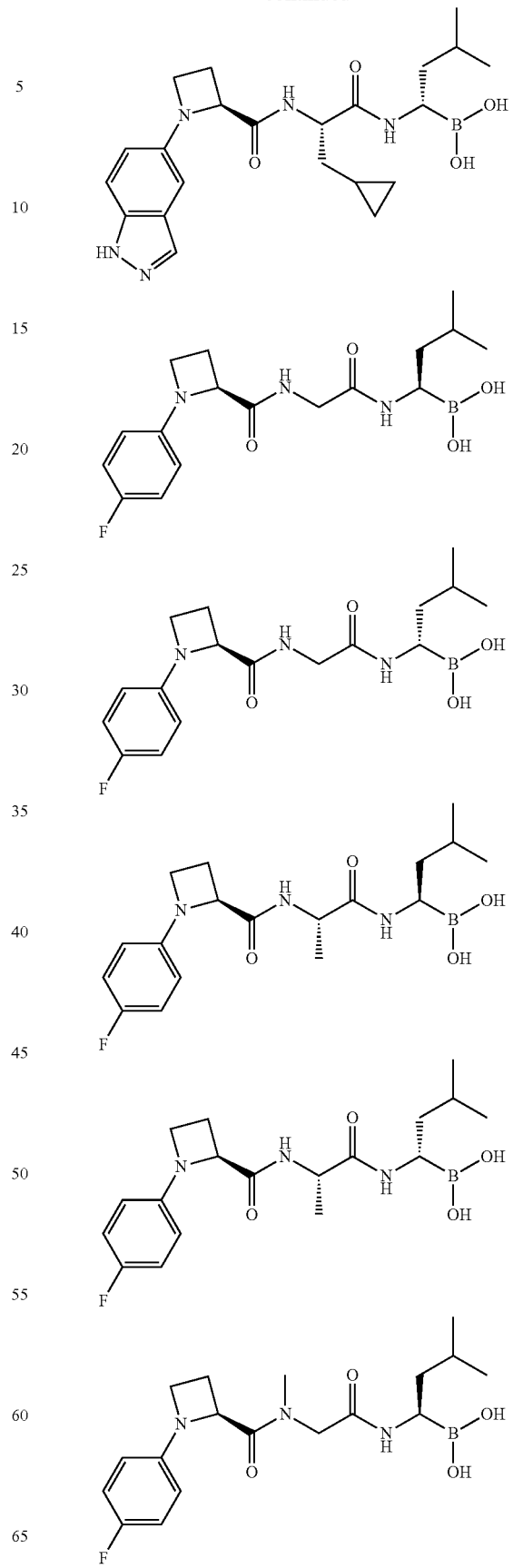

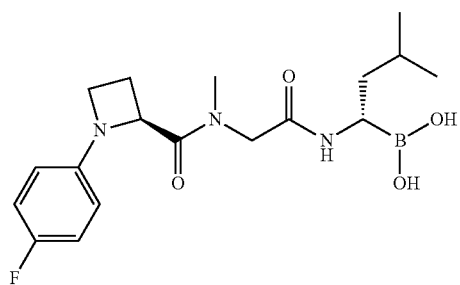
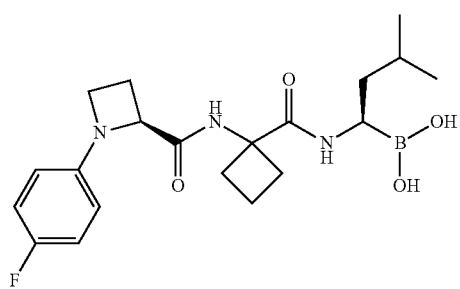
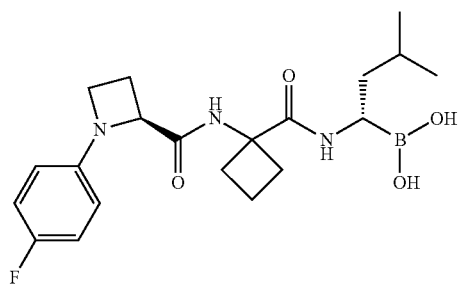
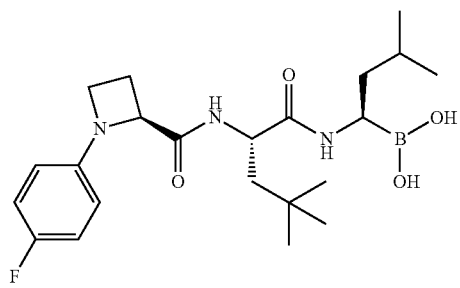
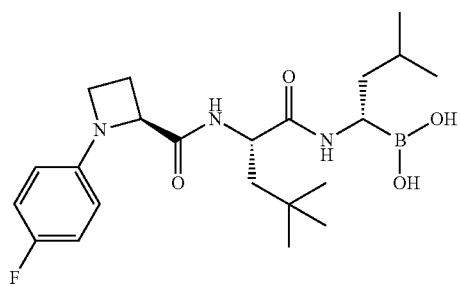
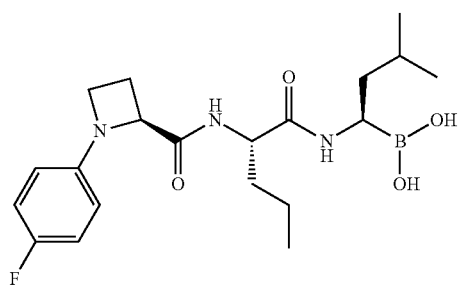
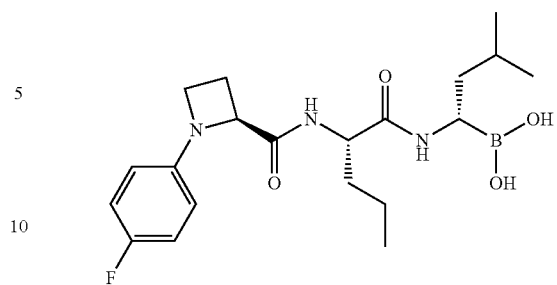
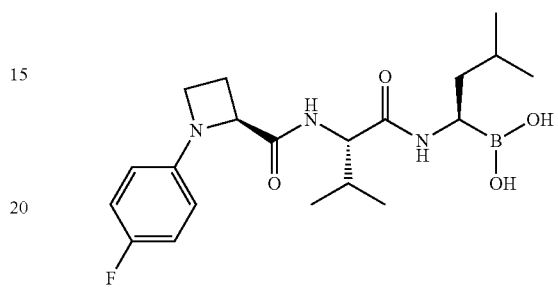
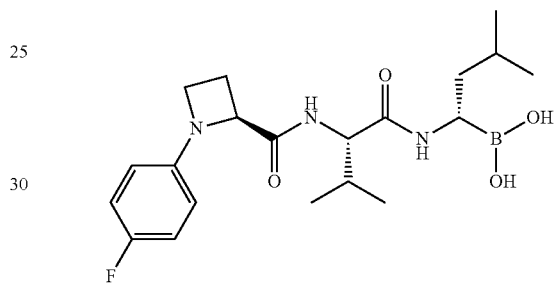
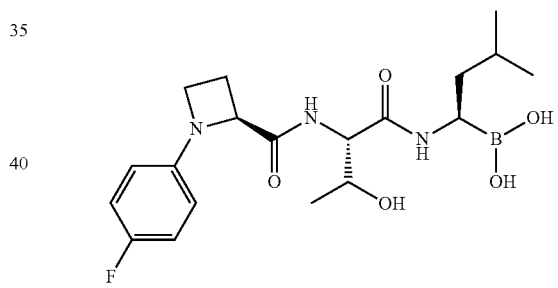
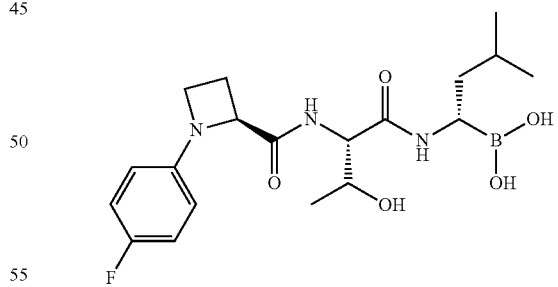
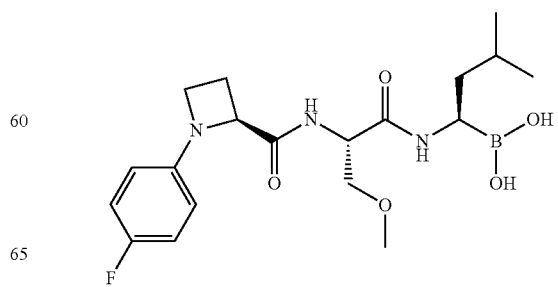

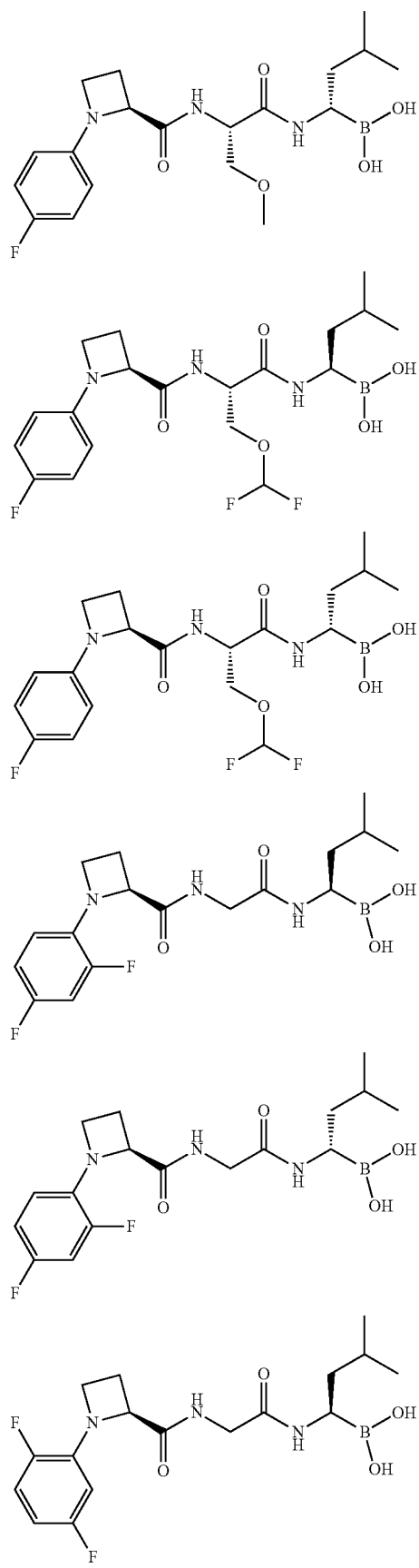 [SMILES: CCC[C@H](NC(=O)[C@@H]1CCN1c1ccc(F)cc1)C(=O)N[C@H](CC(C)C)B(O)O ; CC(C)C[C@H](NC(=O)[C@@H](NC(=O)[C@@H]1CCN1c1ccc(F)cc1)C(C)C)B(O)O ; CC(C)C[C@@H](NC(=O)[C@@H](NC(=O)[C@@H]1CCN1c1ccc(F)cc1)C(C)C)B(O)O ; CC(C)C[C@H](NC(=O)[C@@H](NC(=O)[C@@H]1CCN1c1ccc(F)cc1)C(C)O)B(O)O ; CC(C)C[C@@H](NC(=O)[C@@H](NC(=O)[C@@H]1CCN1c1ccc(F)cc1)C(C)O)B(O)O ; COC[C@H](NC(=O)[C@@H]1CCN1c1ccc(F)cc1)C(=O)N[C@@H](CC(C)C)B(O)O]
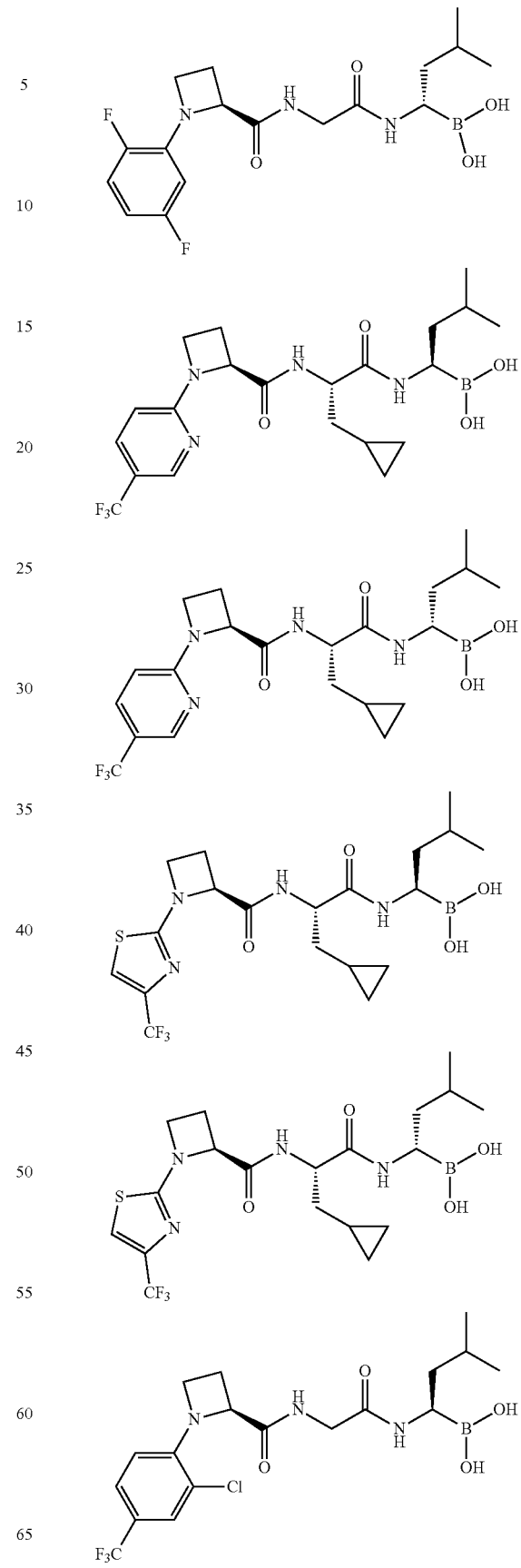

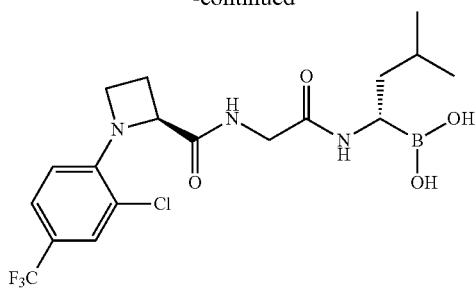
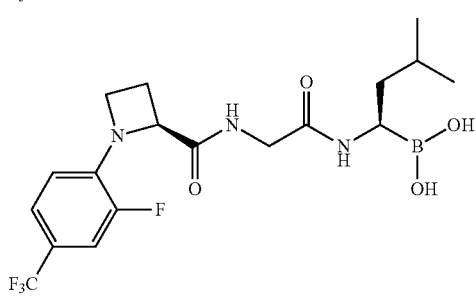
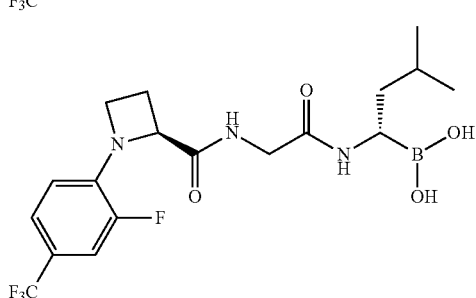
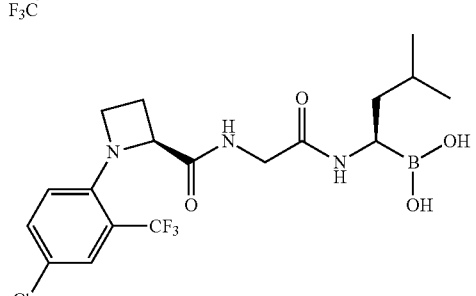
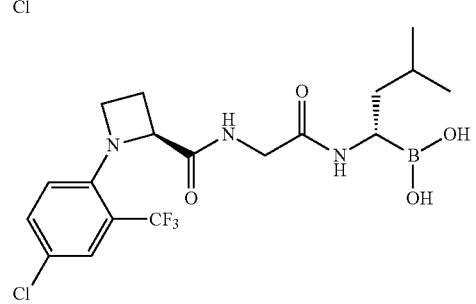
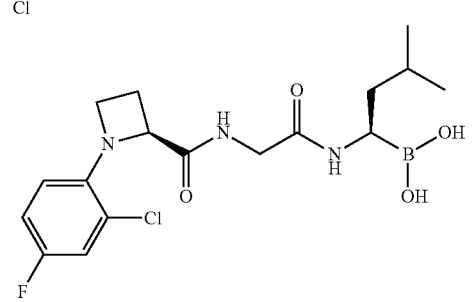
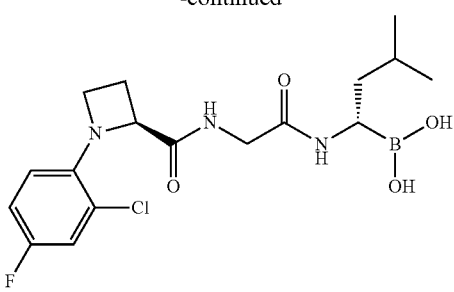
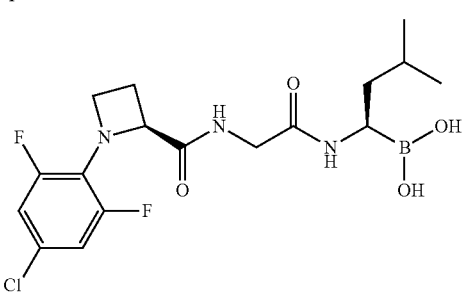
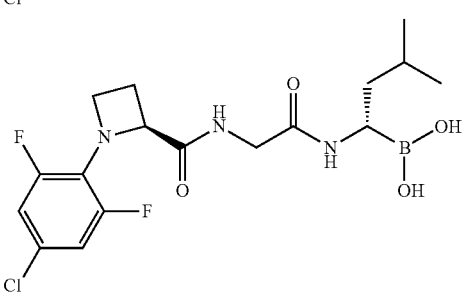
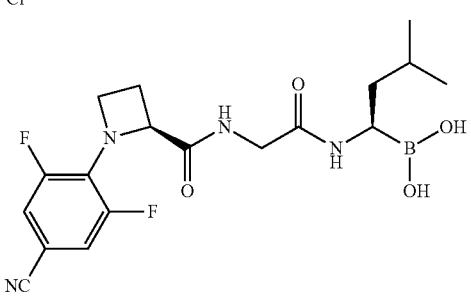
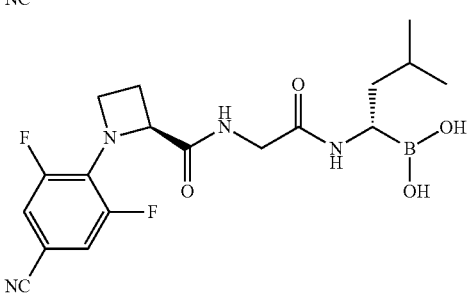
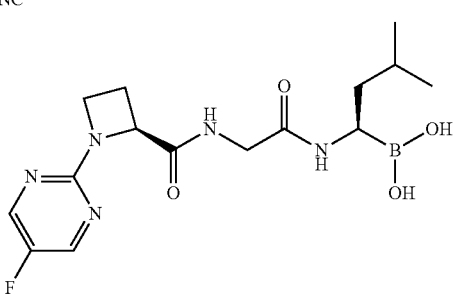

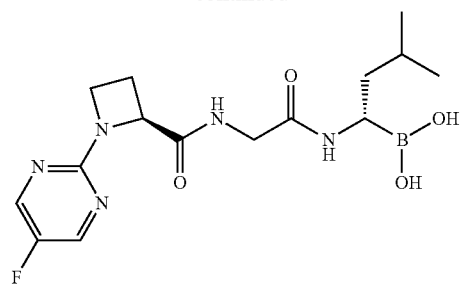
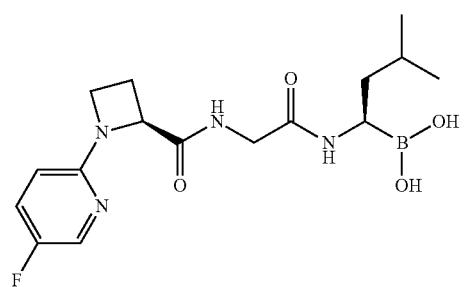
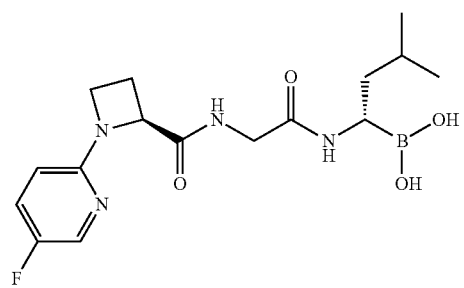
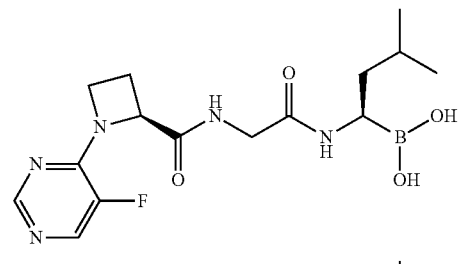
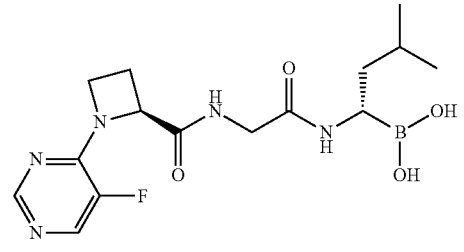
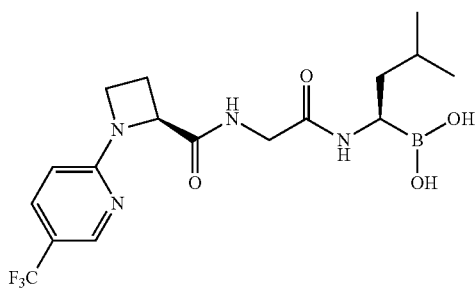
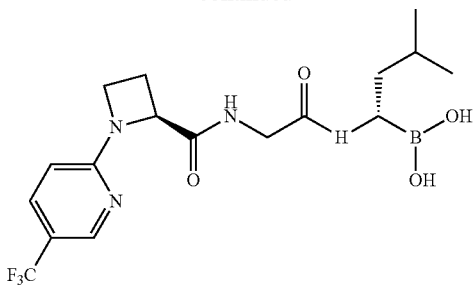
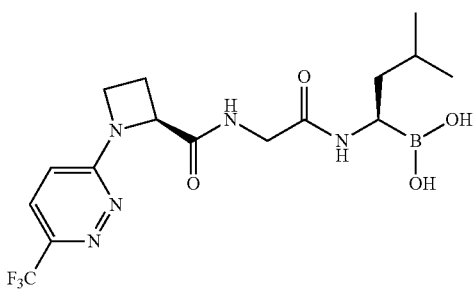
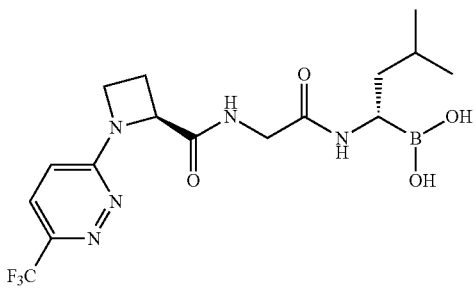
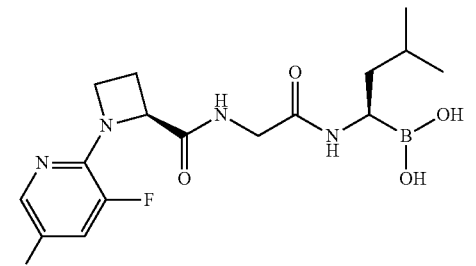
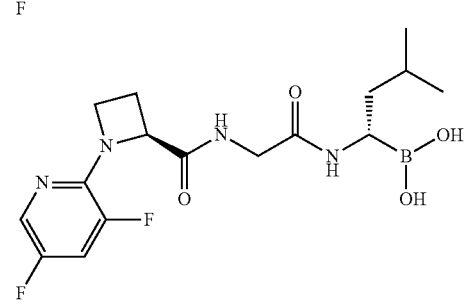
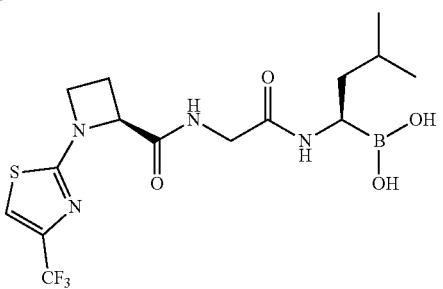

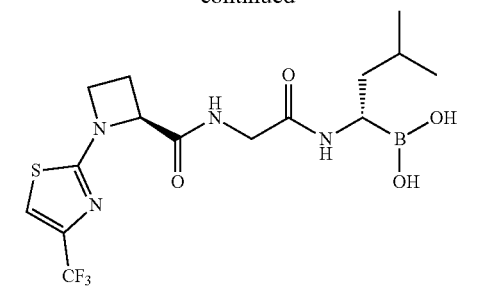

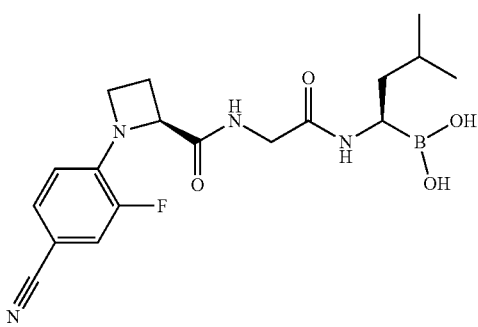

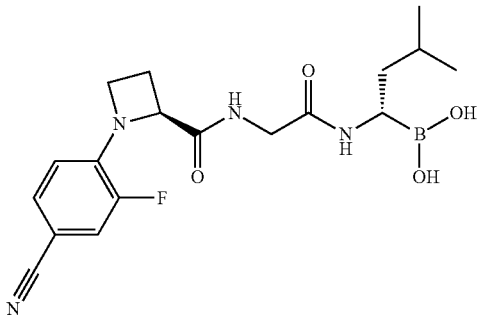

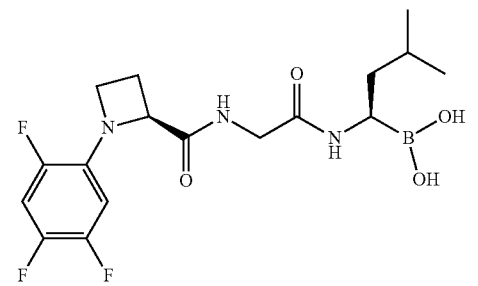

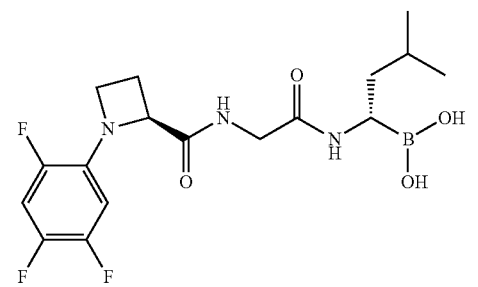

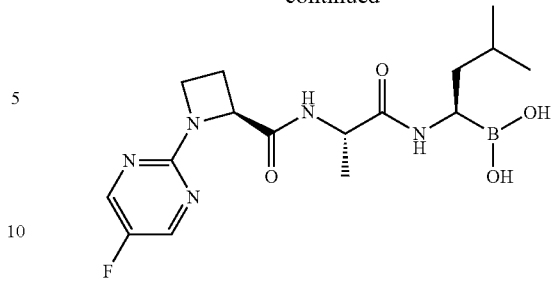

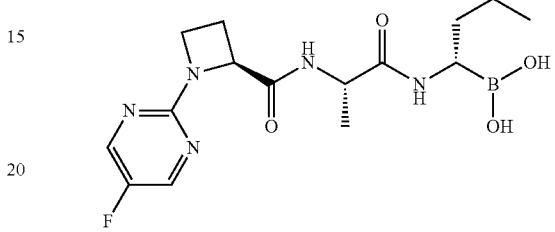

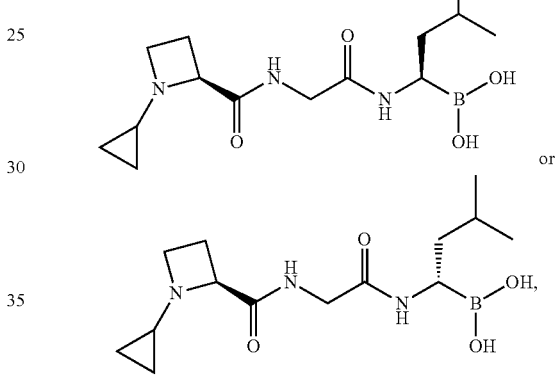

or a pharmaceutically acceptable salt thereof.

In another aspect, the present application also provides a pharmaceutical composition comprising the compound of Formula (I), a pharmaceutically acceptable salt, a tautomer, a stereoisomer or a geometric isomer thereof. In some embodiments, the pharmaceutical composition of the present application further comprises a pharmaceutically acceptable excipient, carrier or diluent.

In a further aspect, the present application also provides a method for the treatment of multiple myeloma in a mammal, comprising administering to the mammal in need thereof, preferably a human, a therapeutically effective amount of the compound of Formula (I), a pharmaceutically acceptable salt, a tautomer, a stereoisomer or a geometric isomer thereof, or a pharmaceutical composition thereof.

In still another aspect, the present application also provides use of the compound of Formula (I), a pharmaceutically acceptable salt, a tautomer, a stereoisomer or a geometric isomer thereof, or a pharmaceutical composition thereof in the preparation of a medicament for the prophylaxis or treatment of multiple myeloma.

In yet another aspect, the present application also provides use of the compound of Formula (I), a pharmaceutically acceptable salt, a tautomer, a stereoisomer or a geometric isomer thereof, or a pharmaceutical composition thereof in the prophylaxis or treatment of multiple myeloma.

In another aspect, the present application also provides the compound of Formula (I), a pharmaceutically acceptable salt, a tautomer, a stereoisomer or a geometric isomer thereof, or a pharmaceutical composition thereof for use in the prophylaxis or treatment of multiple myeloma.

In a further aspect, the compound of Formula (I) of the present application can be prepared by a person skilled in the art through the following general schemes and using a standard method in the art:

<General Scheme 1>

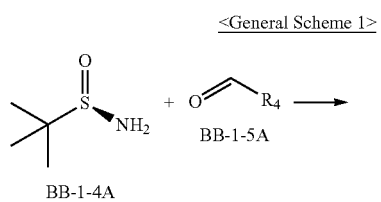

BB-1-4A  BB-1-5A

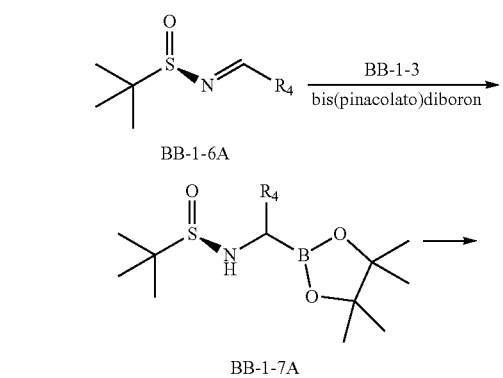

<General Scheme 2>

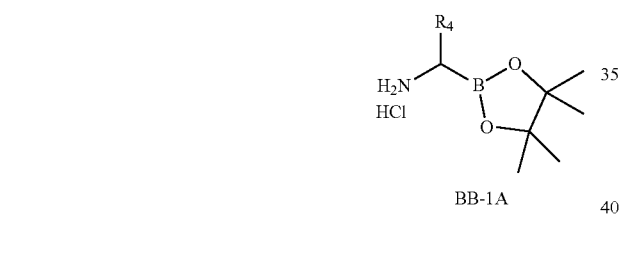

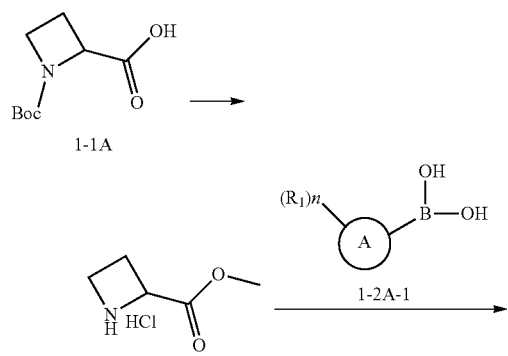

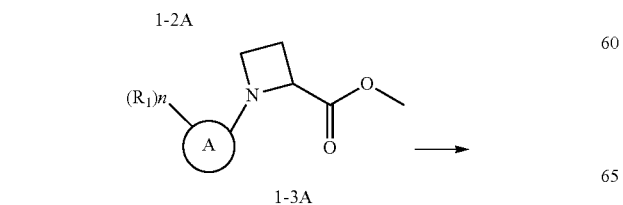

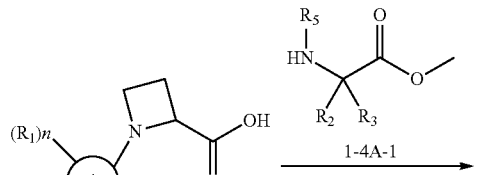

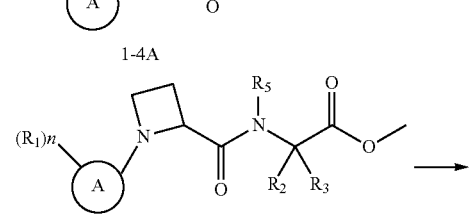

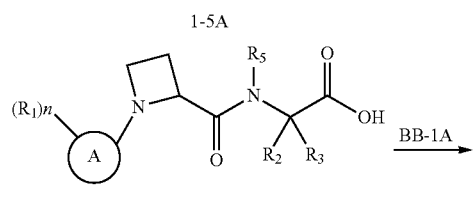

<General Scheme 3>

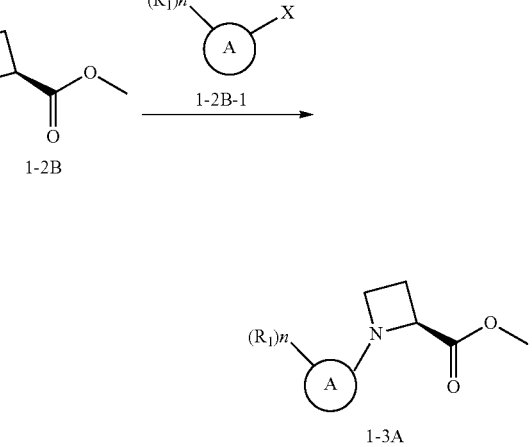

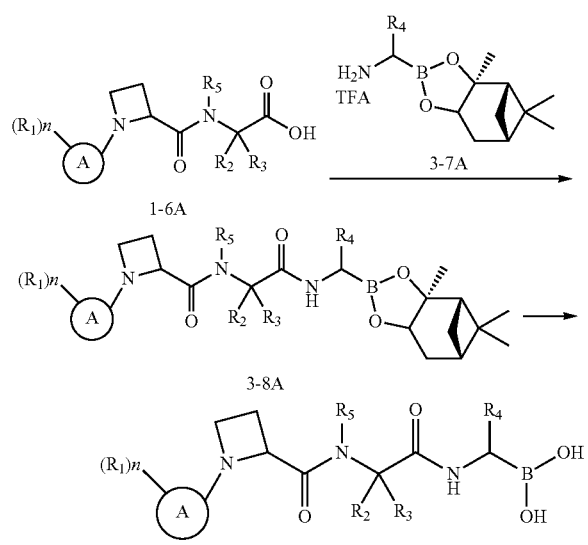

The compound of the present application has a good antitumor effect on multiple myeloma and good oral bioavailability, and has a therapeutic potential for multiple myeloma resistant to bortezomib.

Definition

Unless stated otherwise, the following terms and phrases used herein have the following meanings. A specific term or phrase shall not be considered unclear or indefinite when it is not specially defined. It should be understood according to its general meaning. A trade name used herein refers to a corresponding product or an active ingredient thereof.

The term "pharmaceutically acceptable" refers to a compound, material, composition and/or dosage form that is applicable to the contact with human and animal tissues without an excessive toxicity, irritation, allergic reaction or other problems or complications in the scope of reliable medical judgment, and is commensurate with an acceptable benefits/risk ratio.

The dashed line (----) in the structural units or groups in the present application refers to a covalent bond.

When a covalent bond in some of the structural units or groups in the present application (for example, the dashed line (----) in is not linked to a specific atom, it means that the covalent bond may be linked to any atom in the structural units or groups as long as the valence bond theory is not violated. Therefore, for example, the structural unit includes The term "pharmaceutically acceptable salt" refers to the salt of the compound of the present application, which is prepared from the compound with specific substituents discovered by the present application and a relatively non-toxic acid or base. When the compound of the present application contains a relatively acidic functional group, a base addition salt can be obtained by contacting the compound with a sufficient amount of a base. The pharmaceutically acceptable base addition salt includes the salt of sodium, potassium, calcium, ammonium, organic ammonium or magnesium or the like. When the compound of the present application contains a relatively alkaline functional group, an acid addition salt can be obtained by contacting the compound with a sufficient amount of an acid. Examples of the pharmaceutically acceptable acid addition salt include an inorganic acid salt, wherein the inorganic acid includes such as hydrochloric acid, hydrobromic acid, nitric acid, carbonic acid, bicarbonate, phosphoric acid, hydrogen phosphate, dihydrogen phosphate, sulfuric acid, hydrogen sulfate, hydriodic acid, phosphorous acid, etc.; and an organic acid salt, wherein the organic acid includes such as acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluene sulfonic acid, citric acid, tartaric acid, methylsulfonic acid and the like; and also includes a salt of an amino acid (e.g. arginine), and a salt of an organic acid such as glucuronic acid and the like (see Berge et al., "Pharmaceutical Salts", *Journal of Pharmaceutical Science* 66: 1-19 (1977)). Some specific compounds of the present application contain alkaline and acidic functional groups so as to be able to be converted to any base addition salts or acid addition salts.

Preferably, the parent form of a compound is regenerated by contacting a salt with a base or an acid in a conventional manner and then separating the parent compound. The differences between a parent form of a compound and the various salt forms thereof lie in some physical properties. For example, the solubilities in a polar solvent are different.

The "pharmaceutically acceptable salt" as used herein belongs to the derivatives of the compound of the present application, wherein the parent compound is modified by being salified with an acid or base. Examples of the pharmaceutically acceptable salt include but not limited to: an inorganic or organic acid salt of a base (such as amine), an alkali metal or organic salt of an acid (such as carboxylic acid), and so on. The pharmaceutically acceptable salt includes common non-toxic salts or quaternary ammonium salts of the parent compound, such as a salt formed by a non-toxic inorganic or organic acid. The common non-toxic salts include but not limited to those salts derived from inorganic acids and organic acids, wherein the inorganic acids or organic acids are selected from 2-acetoxybenzoic acid, 2-isethionic acid, acetic acid, ascorbic acid, benzenesulfonic acid, benzoic acid, bicarbonate, carbonic acid, citric acid, edetic acid, ethanedisulfonic acid, ethanesulfonic acid, fumaric acid, glucoheptonic acid, gluconic acid, glutamic acid, glycolic acid, hydrobromic acid, hydrochloric acid, hydriodate, hydroxynaphthoic acid, isethionic acid, lactic acid, dodecanesulfonic acid, maleic acid, malic acid, mandelic acid, methanesulfonic acid, nitric acid, oxalic acid, pamoic acid, pantothenic acid, phenylacetic acid, phosphoric acid, polygalacturonic acid, propionic acid, salicylic acid, stearic acid, subacetic acid, succinic acid, aminosulfonic acid, sulfanilic acid, sulphuric acid, tannic acid, tartaric acid and p-toluene sulfonic acid.

The pharmaceutically acceptable salt of the present application can be synthesized with a parent compound containing an acidic or alkaline group by a conventional chemical method. Generally, the preparation method of the salt comprises: reacting these compounds in the forms of free acids or bases with a stoichiometric amount of proper bases or acids in water or an organic solvent or a water-organic solvent mixture. In general, a non-aqueous media such as ether, ethyl acetate, ethanol, isopropanol or acetonitrile is preferable.

In addition to a salt form, there is a prodrug form for the compound of the present invention. The prodrug of the compound described in the present invention is easily converted to the compound of the present invention via chemical changes under physiological conditions. Besides, the prodrug can be converted to the compound of the present invention via a chemical or biochemical method in vivo environment.

Some compounds of the present application may exist in non-solvate or solvate forms, including hydrate forms. In general, the solvate form is similar to the non-solvate form, both of which are included within the scope of the present application.

Some compounds of the present application may contain asymmetric carbon atoms (stereocenter) or double bonds. Racemic isomers, diastereomers, geometric isomers and single isomers are included within the scope of the present application.

Unless otherwise indicated, the absolute configuration of a stereocenter is represented by wedge and dashed bonds ( ⌿ ,\\\\"); one of the absolute configurations (for example, one of ⌿ and ,\\\\") of a stereocenter is represented by the wavy line ⌇ ; and the relative configuration of a stereocenter is represented by ⌿ ,\\\\". When the compound of the present application contains an olefinic double bond or other geometrically asymmetric center, unless otherwise specified, E and Z geometric isomers are included. Similarly, all tautomeric forms are included within the scope of the present application.

The compound of the present application may exist in the form of a specific geometric or stereoisomeric isomer. The present application envisages all of these compounds, including tautomers, cis- and trans-isomers, (−)- and (+)-enantiomers, (R)- and (S)-enantiomers, diastereomers, (D)-isomers, (L)-isomers, as well as racemic mixtures and other mixtures, such as enantiomer- or diastereoisomer-enriched mixtures, all of which are included within the scope of the present application. Other asymmetric carbon atoms may exist in substituents such as alkyl. All of these isomers and their mixtures are included within the scope of the present application.

Optically active (R)- and (S)-isomers and (D)- and (L)-isomers can be prepared by chiral synthesis or chiral reagents or other conventional techniques. An enantiomer of a compound of the present application can be prepared by asymmetric synthesis or the derivatization action with chiral auxiliaries, in which the resulting diastereomer mixtures are isolated, and the auxiliary groups are cleaved to provide the desired pure enantiomer. Alternatively, when a molecule contains an alkaline functional group (such as amino) or an acidic functional group (such as carboxyl), the molecule is reacted with an appropriate optical active acid or base to form a diastereomer salt, the diastereomer is resoluted by well-known conventional methods in the art, and then pure enantiomers can be obtained. In addition, the separation of enantiomers and diastereomers is usually realized by chromatography, which employs a chiral stationary phase, and optionally is combined with the chemical derivatization method (e.g. a carbamate is generated from an amine).

The compound of the present application may comprise unnatural proportion of atomic isotopes at one or more atoms that constitute the compound. For example, the compound can be labeled by a radioactive isotope, such as tritium ($^{3}H$), iodine-125($^{125}I$) or C-14($^{14}C$). All the variants composed by isotopes of the compound disclosed in the present application, whether radioactive or not, are included within the scope of the present application.

The term "pharmaceutical composition" refers to a mixture of one or more of the compounds or salts thereof according to the present application and a pharmaceutically acceptable excipient. An object of the pharmaceutical composition is to facilitate administering the compound according to the present application to an organism.

The term "pharmaceutically acceptable carrier", "pharmaceutically acceptable excipients" or "pharmaceutically acceptable adjuvant" refers to those carriers, excipients or adjuvants that do not cause significant stimulation to an organism, and will not impair the bioactivity and properties of an active compound. Suitable carriers, excipients or adjuvants are well known to those skilled in the art, for example, carbohydrates, waxes, water-soluble and/or water-swellable polymers, hydrophilic or hydrophobic materials, gelatin, oils, solvents, water, and the like.

The term "comprise" and English variants thereof (such as comprises or comprising) should be understood as open and non-exclusive meanings, i.e. "including but not limited to".

The pharmaceutical composition according to the present application may be prepared by combining the compound according to the present application with a suitable pharmaceutically acceptable adjuvant. For example, it may be formulated into solid, semisolid, liquid or gaseous formulations, such as tablets, pills, capsules, powders, granules, lozenges, ointments, syrups, emulsions, suspensions, solutions, suppositories, injections, inhalants, gels, microspheres, aerosols, and the like.

Typical administration routes of the compound according to the present application or the pharmaceutically acceptable salt, the tautomer, the stereoisomer or the geometric isomer thereof, or the pharmaceutical composition thereof include, but are not limited to, oral, rectal, transmucosal, topical, transdermal, inhalation, parenteral, sublingual, intravaginal, intranasal, intraocular, intraperitoneal, intramuscular, subcutaneous, and intravenous administration. Preferred administration routes are oral administration and injection administration.

The pharmaceutical composition according to the present application may be manufactured by using a method known in the art, such as conventional mixing method, dissolution method, granulation method, dragee manufacture method, grinding method, emulsification method, lyophilization method and the like.

In some embodiments, the pharmaceutical composition of the present application is in oral form. For oral administration, the pharmaceutical composition may be formulated by mixing an active compound with a pharmaceutically acceptable adjuvant or excipient well-known in the art. Such adjuvant or excipient enables the compound according to the present application to be formulated into tablets, pills, lozenges, dragees, capsules, powders, granules, liquids, syrups, emulsions, gels, slurries, suspensions, and the like, which are used for oral administration to a patient.

A solid pharmaceutical composition suitable for oral administration may be prepared by a conventional mixing, filling or tabletting method. For example, oral compositions in solid form may be obtained by mixing the active compound with a solid adjuvant or excipient, optionally grinding the resulting mixture, if necessary, adding other appropriate adjuvants or excipients, and then processing the mixture into granules to obtain the cores of a tablet or dragee. Appropriate adjuvants or excipients include, but are not limited to, fillers, binders, diluents, disintegrating agents, lubricants, glidants, sweetening agents, flavoring agents, and the like.

The pharmaceutical composition of the present application may also be suitable for parenteral administration, such as a sterile solution, a suspension, an emulsion or a lyophilized product in an appropriate unit dosage form. A suitable excipient such as a filler, a buffering agent or a surfactant can be used.

The compound of Formula (I) of the present application may be administered daily at a dose of 0.01 mg/kg body weight to 200 mg/kg body weight in a single dose or in divided doses.

The term "a pharmaceutically acceptable carrier" refers to any agent, carrier or vehicle which is capable of delivering an effective amount of the active substance disclosed in the present application, does not interfere with the biological activity of the active substance, and has no toxic side-effects on a host or patient. Representative carriers include water, oil and minerals, cream base, lotion matrix, ointment matrix, etc. These matrixes include suspensions, suspending agent, viscosity increasers, transdermal enhancers, etc. These agents are well known to those skilled in the field of cosmetics or topical medicament. Other information about the carrier can refer to Remington: The Science and Practice of Pharmacy, 21st Ed., Lippincott, Williams & Wilkins (2005), the content of which is incorporated herein by reference.

The term "excipient" or "adjuvant" usually refers to a carrier, diluent and/or medium required for the preparation of an effective pharmaceutical composition.

For a drug or pharmacological active agent, the term "effective amount" or "therapeutically effective amount" refers to a sufficient amount of a drug or formulation that can achieve desired effects but is non-toxic. For the oral formulation of the present application, "an effective amount" of one active substance in the composition refers to the amount required to achieve a desired effect in combination with another active substance in the composition. The determination of an effective amount varies from person to person, depending on the age and general condition of a subject, and also depending on the specific active substance. An appropriate effective amount in individual cases can be determined by the person skilled in the art according to conventional tests.

The term "active ingredient", "therapeutic agent", "active substance" or "active agent" refers to a chemical entity, which can effectively treat a target disorder, disease or condition.

The term "treating" or "treatment" means that the compound or formulation of the present application is administrated to prevent, ameliorate or eliminate diseases, or one or more symptoms associated with said diseases, and comprises:

(i) preventing the occurrence of a disease or condition in mammals, particularly when such mammals are susceptible to the disease or the condition, but have not yet been diagnosed as suffering from said disease or condition;

(ii) inhibiting a disease or condition, i.e., suppressing the development of the disease or condition;

(iii) alleviating a disease or condition, i.e., causing the regression of the disease or condition.

The term "therapeutically effective amount" refers to the amount of the compound of the present application that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. The amount of the compound of the present application, which constitutes "therapeutically effective amount", varies depending on the nature of the compound, the state and severity of a disease, condition or disorder, the administration route and the age of a mammal to be treated. However the amount can be routinely determined by a person skilled in the art, based on his knowledge and the present disclosure.

The term "optional" or "optionally" means that the subsequently described event or circumstance may or may not occur, and that the description includes instances where said event or circumstance occurs and instances where said event or circumstance does not occurs.

The term "substituted" refers to one or more hydrogen atoms on a specific atom are substituted by a substituent, including deuterium and variants of hydrogen, as long as the valence state of the specific atom is normal and the compound obtained after substitution is stable. When the substituent is an oxo (i.e., =O), which means that two hydrogen atoms are replaced, the oxo substitution will not occur on an aromatic group. The term "optionally substituted" means that it may be substituted or not be substituted, and unless otherwise specified, the type and number of substituents can be arbitrary under the premise that it can be achieved in chemistry.

When any variable (e.g. R or R$_1$) occurs more than one time in the composition or structure of a compound, the definition in each occurrence is independent. Therefore, for example, if a group is substituted by 0-2 R, the group may optionally be substituted by at most two R, and R in each case has an independent option. As another example, each of the R is in the structural unit

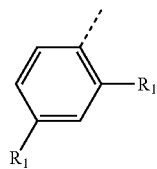

is independent, and they may be the same or different. In addition, the combination of substituents and/or their variants is allowed only if such a combination will lead to a stable compound.

When the number of a linking group is 0, such as —(CRR)$_0$—, it means that the linking group is a single bond.

Unless otherwise specified, C$_{3-6}$ cycloalkyl-(CH$_2$)$_{1-3}$— includes C$_{3-6}$ cycloalkyl-CH$_2$—, C$_{3-6}$ cycloalkyl-(CH$_2$)$_2$— and C$_{3-6}$ cycloalkyl-(CH$_2$)$_3$—. Similarly, phenyl-(CH$_2$)$_{1-3}$— includes phenyl-CH$_2$—, phenyl-(CH$_2$)$_2$— and phenyl-(CH$_2$)$_3$—.

When one of the variables is a single bond, it means that the two groups connected thereto are directly connected to each other. For example, when L in A-L-Z represents a single bond, it means that the structure is actually A-Z.

When a substituent is absent, it means that the substituent is not present. For example, when X in A-X is absent, it means that the structure is actually A. When a substituent may be linked to one or more atoms on a ring, the substituent can be bonded to any atom on the ring. For example, a structural unit

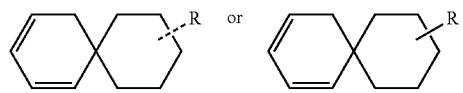

means that the substituent R may substitute for a hydrogen atom at any position on the ring of cyclohexyl or cyclohexadiene. When the atom through which an enumerated substituent is linked to the group to be substituted is not designated, such substituent can be bonded through any atom thereof. For example, pyridyl as a substituent can be linked to the group to be substituted through any carbon atom on the pyridine ring. When an enumerated linking group does not indicate its linking direction, the linking direction is arbitrary. For example, the linking group L in

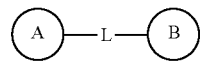

is -M-W-, then -M-W- can link ring A and ring B to form

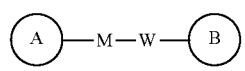

in the direction same as left-to-right reading order, and form

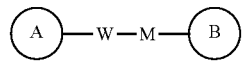

in the direction contrary to left-to-right reading order. The combination of the linking groups, substituents and/or their variants is allowed only if such a combination will lead to a stable compound.

Unless otherwise specified, the term "hetero" represents a heteroatom or a heteroatom group (i.e. a group containing a heteroatom), including atoms except for carbon (C) and hydrogen (H) and groups containing these heteroatoms, for example, including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O)—, —S(=O)$_2$—, and optionally substituted —C(=O)N(H)—, —N(H)—, —C(=NH)—, —S(=O)$_2$N(H)— or —S(=O)N(H)—.

Unless otherwise specified, the term "ring" refers to a substituted or unsubstituted cycloalkyl, heterocycloalkyl, cycloalkenyl, heterocycloalkenyl, cycloalkynyl, heterocycloalkynyl, aryl or heteroaryl. Said ring includes a monocycle, a bicycle, a dicycle, a spiro ring, a fused ring or a bridged ring. The number of the atoms in the ring is usually defined as the number of the members forming the ring. For example, "5- to 7-membered ring" refers to a ring formed by 5 to 7 atoms. Unless otherwise specified, the ring optionally contains 1-3 heteroatoms. Therefore, "5- to 7-membered ring" includes, for example, phenyl, pyridinyl and piperidinyl. On the other hand, the term "5- to 7-membered heterocyclyl" includes pyridyl and piperidinyl, but does not include phenyl. The term "ring" also includes a ring system containing at least one ring, wherein each "ring" independently meets the above definition.

Unless otherwise specified, the term "heterocycle" or "heterocyclyl" refers to a stable monocyclic, bicyclic or tricyclic ring containing a heteroatom or a heteroatom group, they may be saturated, partially unsaturated or unsaturated (aromatic), and they contain carbon atoms and 1, 2, 3 or 4 heteroatoms which are independently selected from the group consisting of N, O and S, wherein any of the above-mentioned heterocycle may be fused to a benzene ring to form a bicyclic ring. Nitrogen atoms and sulfur atoms may be optionally oxidized (i.e., NO and $S(O)_p$, p is 1 or 2). The nitrogen atoms may be substituted or unsubstituted (i.e. N or NR, wherein R is H or other substituents that have been defined herein). The heterocycle may be attached to the side group of any heteroatoms or carbon atoms to form a stable structure. If the formed compound is stable, the heterocycle described herein may be substituted on its carbon or nitrogen atoms. The nitrogen atoms in the heterocycle are optionally quaternized. A preferred embodiment is, when the total number of S and O atoms in the heterocycle is more than 1, these heteroatoms are not adjacent to each other. Another preferred embodiment is the total number of S and O atoms in the heterocycle is not more than 1. As used herein, the term "aromatic heterocyclic group" or "heteroaryl" refers to a stable 5-, 6-, 7-membered monocyclic or bicyclic or 7-, 8-, 9- or 10-membered bicyclic aromatic heterocyclyl, which contains carbon atoms and 1, 2, 3 or 4 heteroatoms which are independently selected from the group consisting of N, O and S. The nitrogen atoms may be substituted or unsubstituted (i.e. N or NR, wherein R is H or other substituents that have been defined herein). Nitrogen atoms and sulfur atoms may be optionally oxidized (i.e., NO and $S(O)_p$, p is 1 or 2). It is worth noting that, the total number of S and O atoms in the aromatic heterocycle is not more than 1. Bridged rings are also included in the definition of the heterocycle. When one or more atoms (i.e. C, O, N, or S) are connected to two nonadjacent carbon atoms or nitrogen atoms, a bridged ring is formed. It is worth noting that, a bridge always converts a monocyclic ring into a tricyclic ring. In the bridged ring, the substituent in the ring may also locate on the bridge.

Examples of heterocyclyl include but not limited to: acridinyl, azocinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl, decahydroquinolyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indoalkenyl, indolinyl, indolizinyl, indolyl, 3H-indolyl, isobenzofuranyl, isoindolyl, isoindolinyl, isoquinolyl, isothiazolyl, isoxazolyl, methylenedioxyphenyl, morpholinyl, naphthyridinyl, octahydroisoquinolyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxyindolyl, pyrimidyl, phenanthridinyl, phenanthrolinyl, phenazinyl, phenothiazinyl, benzoxanthinyl, phenoxazinyl, phthalazinyl, piperazinyl, piperidyl, piperidonyl, 4-piperidonyl, piperonyl, pteridyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyrrolidinyl, pyrrolinyl, 2H-pyrrolyl, pyrrolyl, quinazolinyl, quinolyl, 4H-quinolizinyl, quinoxalinyl, quinuclidinyl, tetrahydrofuryl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazyl, isothiazolylthienyl, thienoxazolyl, thienothiazolyl, thienoimidazolyl, thienyl, triazinyl, 1,2,3-triazolyl, 1,2,4-triazolyl, 1,2,5-triazolyl, 1,3,4-triazolyl and xanthenyl. Fused-ring and spiro-ring compounds are also included.

Unless otherwise specified, the term "hydrocarbyl" or its specific terms (such as alkyl, alkenyl, alkynyl, aryl and so on) themself or as a part of another substituent represent a linear, branched or cyclic hydrocarbon group or a combination thereof, which may be completely saturated (such as alkyl), or mono- or poly-unsaturated (such as alkenyl, alkynyl and aryl), may be monosubstituted or multisubstituted, may be monovalent (e.g., methyl), divalent (e.g., methylene) or multivalent (e.g., methine), may include bivalent or multivalent atomic groups, and have a specified number of carbon atoms (for example, $C_1$-$C_{12}$ represents 1 to 12 carbon atoms, $C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$, and $C_{3-12}$ is selected from $C_3$, $C_4$, $C_5$, $C_6$, $C_7$, $C_8$, $C_9$, $C_{10}$, $C_{11}$ and $C_{12}$). The term "hydrocarbyl" includes but not limited to aliphatic hydrocarbyl and aromatic hydrocarbyl. The aliphatic hydrocarbyl includes linear and cyclic aliphatic hydrocarbyl, and specifically includes but not limited to alkyl, alkenyl and alkynyl. The aromatic hydrocarbyl includes but not limited to 6- to 12-membered aromatic hydrocarbyl, such as phenyl, naphthyl and the like. In some embodiments, the term "hydrocarbyl" represents a linear or branched atomic group or a combination thereof, which may be completely saturated, or mono- or poly-unsaturated, and may include divalent and polyvalent groups. Examples of saturated hydrocarbon groups include but not limited to homologues or isomers of methyl, ethyl, n-propyl, iso-propyl, n-butyl, tert-butyl, iso-butyl, sec-butyl, cyclohexyl, (cyclohexyl)methyl, cyclopropyl methyl, and n-amyl, n-hexyl, n-heptyl, n-octyl and the like. Unsaturated hydrocarbyl has one or more double bonds or triple bonds, and its examples include but not limited to vinyl, 2-propenyl, butenyl, crotyl, 2-isopentenyl, 2-butadienyl, 2,4-pentadienyl, 3-(1,4-pentadienyl), acetenyl, 1-propinyl and 3-propinyl, 3-butynyl, and the like, and higher homologs and isomers.

Unless otherwise specified, the term "heterohydrocarbyl" or its specific terms (such as heteroalkyl, heteroalkenyl, heteroalkynyl, heteroaryl and the like) themself or combining with another term represents a stable linear, branched or cyclic hydrocarbon group or a combination thereof, which consists of a certain number of carbon atoms and at least one heteroatom. In some embodiments, the term "heteroalkyl" itself or combining with another term represents a stable linear, or branched hydrocarbon group or a combination thereof, which consists of a certain number of carbon atoms and at least one heteroatom. In a typical embodiment, the heteroatom is selected from the group consisting of B, O, N and S, in which the nitrogen and sulfur atoms are optionally oxidized, and the nitrogen atoms are optionally quaternized. Heteroatoms or heteroatom groups may be located in any internal positions of the heterohydrocarbyl, including the position where the hydrocarbyl is attached to the rest part of the molecule. However, the terms "alkoxy", "alkylamino" and "alkylthio" (or thioalkoxy) belong to customary expressions, and refer to those alkyl groups which are attached to the rest of a molecular via an oxygen atom, an amino group or a sulfur atom, respectively. Examples include but not limited to —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —$CH_2$—CH=N—$OCH_3$ and —CH=CH—N(CH$_3$)—CH$_3$. At most two heteroatoms may be adjacent, such as —CH$_2$—NH—OCH$_3$.

Unless otherwise specified, the terms "cyclohydrocarbyl", "heterocyclohydrocarbyl" or specific terms thereof (such as aryl, heteroaryl, cycloalkyl, heterocycloalkyl, cycloalkenyl, heterocycloalkenyl, cycloalkynyl, heterocycloalkynyl and the like) themself or combining with other terms respectively represent a cyclic "hydrocarbyl" or "heterohydrocarbyl". In addition, in terms of heterohydrocarbyl or heterocyclohydrocarbyl (such as heteroalkyl and heterocycloalkyl), heteroatoms may occupy the position where the heterocyclic ring is attached to the rest part of the molecule. Examples of cyclohydrocarbyl include but not limited to cyclopentyl, cyclohexyl, 1-cyclohexenyl, 3-cyclohexenyl, cycloheptyl, etc. Non-limited examples of heterocyclohydrocarbyl include 1-(1,2,5,6-tetrahydropyridinyl), 1-piperidyl, 2-piperidyl, 3-piperidyl, 4-morpholinyl, 3-morpholinyl, tetrahydrofuran-2-yl, tetrahydrofuranylindol-3-yl, tetrahydrothiophen-2-yl, tetrahydrothiophen-3-yl, 1-piperazinyl and 2-piperazinyl.

Unless otherwise specified, the term "alkyl" refers to a straight or branched saturated hydrocarbyl, which may be monosubstituted (e.g., —CH$_2$F) or multisubstituted (e.g., —CF$_3$), and may be monovalent (e.g., methyl), divalent (e.g., methylene) or multivalent (e.g., methine). Examples of alkyl include methyl (Me), ethyl (Et), propyl (e.g., n-propyl and isopropyl), butyl (e.g., n-butyl, isobutyl, s-butyl, and t-butyl), pentyl (e.g., n-pentyl, isopentyl, and neopentyl), and the like. For example, the term "C$_{1-3}$ alkyl" refers to an alkyl containing 1 to 3 carbon atoms (such as methyl, ethyl, n-propyl, isopropyl). For example, the term "C$_{1-6}$ alkyl" refers to an alkyl containing 1 to 6 carbon atoms (such as methyl, ethyl, n-propyl, isopropyl, n-butyl, isobutyl, sec-butyl, tert-butyl, n-pentyl, 1-methylbutyl, 2-methylbutyl, 3-methylbutyl, neopentyl, hexyl, 2-methylpentyl, etc.).

Unless otherwise specified, cycloalkyl includes any stable monocyclic or polycyclic hydrocarbyl, in which any carbon atom is saturated. Cycloalkyl may be monosubstituted or multi-substituted, and may be monovalent, divalent or multivalent. Examples of cycloalkyl include, but are not limited to, cyclopropyl, norbornanyl, [2.2.2]dicyclooctane, [4.4.0]dicyclodecane, and the like.

Unless otherwise specified, cycloalkenyl includes any stable cyclic or polycyclic hydrocarbyl having one or more unsaturated carbon-carbon double bonds at any position on the ring, which may be mono-substituted or multi-substituted, and may be monovalent, divalent or multivalent. Examples of the cycloalkenyl include, but are not limited to, cyclopentenyl, cyclohexenyl, etc.

Unless otherwise specified, cycloalkynyl includes any stable cyclic or polycyclic hydrocarbyl having one or more carbon-carbon triple bonds at any position on the ring, which may be mono-substituted or multisubstituted, and may be monovalent, divalent or multivalent.

Unless otherwise specified, the term "halo" or "halogen" per se or as the part of another substituent refers to fluorine (F), chlorine (Cl), bromine (Br) or iodine (I) atom. Furthermore, the term "haloalkyl" is meant to include monohaloalkyl and polyhaloalkyl. For example, the term "halo(C$_1$-C$_4$) alkyl" is meant to include, but not limited to, trifluoromethyl, 2,2,2-trifluoroethyl, 4-chlorobutyl, 3-bromopropyl and the like. Unless otherwise specified, Examples of haloalkyl include, but are not limited to, trifluoromethyl, trichloromethyl, pentafluoroethyl and pentachloroethyl.

The term "heteroalkyl" is a straight or branched alkyl which preferably has 1 to 14 carbon atoms, more preferably 1 to 10 carbon atoms, still more preferably 1 to 6 carbon atoms, and most preferably 1 to 3 carbon atoms in the chain, wherein one or more of the carbon atoms are substituted with a heteroatom selected from the group consisting of S, O and N. Exemplary heteroalkyl includes alkyl ethers, secondary alkyl amines and tertiary alkyl amines, amides, alkyl sulfides, etc., including alkoxy, alkylthio, alkylamino. Unless otherwise specified, C$_{1-6}$ heteroalkyl includes C$_1$, C$_2$, C$_3$, C$_4$, C$_5$ and C$_6$ heteroalkyl, such as C$_{1-6}$ alkoxy, C$_{1-6}$ alkylthio, and C$_{1-6}$ alkylamino.

The term "alkoxy" refers to an alkyl group as defined above with the indicated number of carbon atoms attached through an oxygen bridge. Unless otherwise specified, C$_{1-6}$ alkoxy includes C$_1$, C$_2$, C$_3$, C$_4$, C$_5$ and C$_6$ alkoxy. Examples of alkoxy include, but are not limited to methoxy, ethoxy, n-propoxy, isopropoxy, n-butoxy, sec-butoxy, tert-butoxy, n-pentyloxy and S-pentoxy.

Unless otherwise specified, the term "aryl" represents a polyunsaturated aromatic hydrocarbon substituent, which may be monosubstituted or multi-substituted, and may be monovalent, divalent or multivalent. It may be monocyclic or polycyclic (for example, 1-3 rings; wherein at least one ring is aromatic). They are fused together or connected covalently. The aryl preferably has 6 to 15 carbon atoms; and more preferably 6 to 12 carbon atoms.

The term "heteroaryl" refers to an aryl containing 1 to 4 heteroatoms. In an exemplary embodiment, the heteroatom is selected from the group consisting of B, N, O, and S, in which the nitrogen and sulfur atoms are optionally oxidized, and the nitrogen atoms are optionally quaternized. The heteroaryl may be connected to the rest part of the molecule via a heteroatom.

Non-limiting examples of aryl or heteroaryl include phenyl, naphthyl, biphenyl, pyrrolyl, pyrazolyl, imidazolyl, pyrazinyl, oxazolyl, phenyl-oxazolyl, isoxazolyl, thiazolyl, furanyl, thienyl, pyridyl, pyrimidinyl, benzothiazolyl, purinyl, benzimidazolyl, indolyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl. The substituent of any of the above aryl and heteroaryl ring systems is selected from the acceptable substituents described below.

Unless otherwise specified, when used in combination with other terms (e.g., aryloxy, arylthio, arylalkyl), the term aryl includes the aryl and heteroaryl ring as defined above. Therefore, the term "aralkyl" is intended to include those atomic groups (e.g., benzyl, phenethyl, pyridylmethyl, and the like) in which an aryl group is attached to an alkyl group, including an alkyl group in which a carbon atom (e.g. methylene) has been replaced with, for example, an oxygen atom, for example, phenoxymethyl, 2-pyridyloxymethyl, 3-(1-naphthyloxy)propyl, and the like.

The term "leaving group" refers to a functional group or atom which can be replaced with another functional group or atom through a substitution reaction (such as nucleophilic substitution reaction). By way of example, representative leaving groups include triflate; chloro, bromo and iodo; sulfonate group, such as mesylate, tosylate, brosylate, p-toluenesulfonate and the like; and acyloxy, such as acetoxy, trifluoroacetoxy and the like.

The term "protecting group" includes, but is not limited to, "amino-protecting group", "carboxyl-protecting group", "hydroxyl-protecting group" and "mercapto-protecting group". The term "amino-protecting group" refers to a protecting group that is suitable for preventing side reactions from occurring at the nitrogen atom of an amino group. Representative amino-protecting groups include, but are not limited to, formyl; acyl, for example, alkanoyl, such as acetyl, trichloroacetyl or trifluoroacetyl; alkoxycarbonyl, such as tert-butoxycarbonyl (Boc); arylmethoxycarbonyl, such as benzyloxycarbobyl (Cbz) and 9-fluorenylmethoxycarbonyl (Fmoc); arylmethyl, such as benzyl (Bn), trityl (Tr), and 1,1-di-(4'-methoxyphenyl)methyl; silyl, such as trimethylsilyl (TMS) and tert-butyldimethylsilyl (TBS); and the like. The term "hydroxyl protecting groups" refers to a protecting group that is suitable for preventing side reactions of a hydroxyl group. Representative hydroxy-protecting groups include, but are not limited to, alkyl, such as methyl, ethyl, and tert-butyl; acyl, for example, alkanoyl, such as acetyl; arylmethyl, such as benzyl (Bn), p-methoxybenzyl (PMB), 9-fluorenylmethyl (Fm), and diphenylmethyl (benzhydryl, DPM); silyl, such as trimethylsilyl (TMS) and tert-butyldimethylsilyl (TBS); and the like.

The compound of the present application can be prepared through many synthetic methods which are well-known to the person skilled in the art, including the following specific embodiments, embodiments obtained by combining the specific embodiments with other chemical synthetic methods and the equivalent alternative methods which are well-known to the person skilled in the art. The preferred embodiments include but not limited to the examples of the present application.

The solvents used in the present application are commercially available. The following abbreviations are used in the present application: aq represents water; HATU represents O-(7-azabenzotriazol-1-yl)-N,N,N',N'-tetramethyluronium hexafluorophosphate; EDC represents N-(3-dimethylaminopropyl)-N'-ethylcarbodiimide hydrochloride; m-CPBA represents 3-chloroperoxybenzoic acid; eq represents equivalent or equal-quantitative; CDI represents carbonyldiimidazole; DCM represents dichloromethane; PE represents petroleum ether; DIAD represents diisopropyl azodicarboxylate; DMF represents N,N-dimethylformamide; DMSO represents dimethyl sulfoxide; EtOAc represents ethyl acetate; EtOH represents ethanol; MeOH represents methanol; CBz represents benzyloxycarbonyl, which is an amino-protecting group; BOC represents tert-butoxycarbonyl, which is an amino-protecting group; HOAc/AcOH represents acetic acid; NaCNBH$_3$ represents sodium cyanoborohydride; rt represents room temperature; O/N represents overnight; THF represents tetrahydrofuran; Boc$_2$O represents di-tert-butyl dicarbonate; TFA represents trifluoroacetic acid; FA represents formic acid; ACN represents acetonitrile; Hepes represents 4-(2-hydroxyethyl)-1-piperazinyl ethanesulfonic acid; HBSS represents Hank's balanced salt solution; DIPEA/DIEA represents diisopropylethylamine; SOCl$_2$ represents thionyl chloride; CS$_2$ represents carbon disulfide; TsOH represents p-toluenesulfonic acid; NFSI represents N-fluoro-N-(phenylsulfonyl)benzenesulfonamide; NCS represents 1-chloropyrrolidine-2,5-dione; n-Bu$_4$NF represents tetrabutylammonium fluoride; iPrOH represents 2-propanol; mp represents melting point; LDA represents lithium diisopropylamide; IPA represents isopropanol; DEA represents diethylamine; DCE represents dichloroethane; TMSCl represents trimethyl chlorosilane; TBTU represents O-benzotriazole-N,N,N',N'-tetramethyluronium tetrafluoroborate; TEA represents triethylamine.

The vendor directory names are used for the commercially available compounds.

EXAMPLES

The present application is described in detail below by way of the following examples, but is not intended to be construed as a limitation. The present application has been described in detail herein, and the specific embodiments thereof are also disclosed herein. It will be apparent for a person skilled in the art that various changes and modifications of the embodiments of the present application can be made without departing from the spirit and scope of the present application.

Reference Example 1

Fragment BB-1

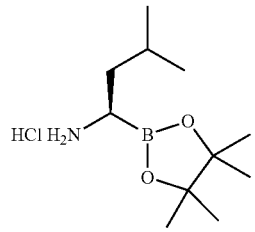

BB-1

Synthetic Route:

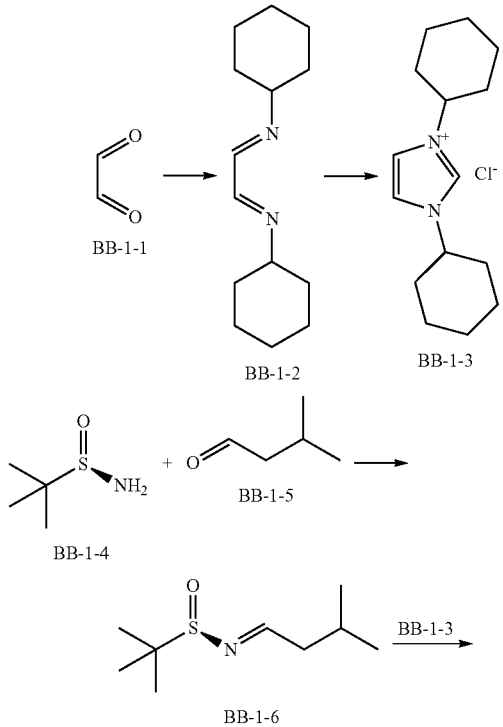

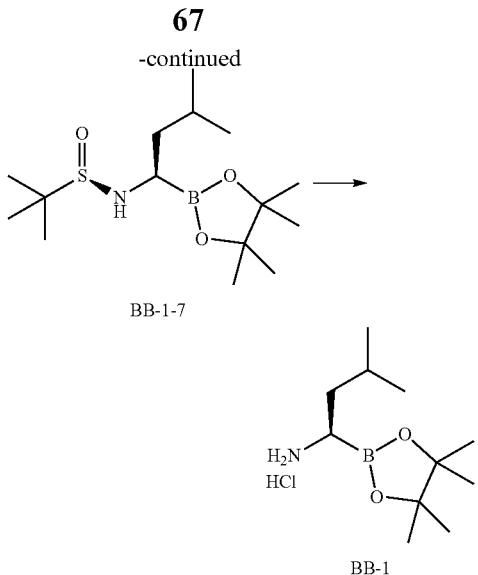

Step 1: Synthesis of Compound BB-1-2

To a solution of compound BB-1-1 (50.00 g, 344.59 mmol, 45.05 mL, 1.00 eq) in DCM (300.00 mL) were added cyclohexylamine (68.35 g, 689.18 mmol, 78.56 mL, 2.00 eq) and calcium chloride (38.24 g, 344.59 mmol, 1.00 eq) in an ice bath. The reaction mixture was warmed, stirred at room temperature for 12 h and then filtered. The filtrate was concentrated under reduced pressure to give a crude product, which was then recrystallized by using methanol (50 mL) to afford compound BB-1-2.

Step 2: Synthesis of Compound BB-1-3

To a solution of N,N,N',N'-tetramethyldiaminomethane (2.55 g, 24.96 mmol, 3.40 mL, 1.10 eq) in DCE (50.00 mL) was added acetyl chloride (1.23 g, 24.96 mmol, 1.10 eq) dropwise in an ice bath. The reaction mixture was stirred at 0° C. for 1 h, and then thereto was added compound BB-1-2 (5.00 g, 22.69 mmol, 1.00 eq). The resulting reaction mixture was warmed to room temperature, continuously stirred for 12 h, and then concentrated under reduced pressure to give a crude product, which was then purified by silica gel column chromatography (mobile phase: dichloromethane:methanol=50:1 to 20:1) to afford compound BB-1-3.

Step 3: Synthesis of Compound BB-1-6

To a solution of compound BB-1-4 (25.00 g, 290.26 mmol, 31.65 mL, 1.20 eq) in DCM (600.00 mL) were added compound BB-1-5 (30.00 g, 247.52 mmol, 1.02 eq), anhydrous magnesium sulfate (145.58 g, 1.21 mol, 5.00 eq) and p-toluenesulfonic acid (6.08 g, 24.19 mmol, 0.10 eq) at room temperature. The reaction mixture was heated to 40° C., continuously stirred for 12 h, and then filtered. The filtrate was concentrated under reduced pressure to give a crude product, which was then purified by silica gel column chromatography (mobile phase: petroleum ether:ethyl acetate=100:1 to 20:1) to afford compound BB-1-6.

Step 4: Synthesis of Compound BB-1-7

To a solution of compound BB-1-6 (38.00 g, 200.72 mmol, 1.00 eq) in toluene (300.00 mL) were added bis(pinacolato)diboron (56.07 g, 220.79 mmol, 1.10 eq), compound BB-1-3 (2.70 g, 10.04 mmol, 0.05 eq) and sodium tert-butoxide (5.79 g, 60.22 mmol, 0.30 eq) at room temperature. The reaction mixture was stirred at room temperature for 96 h under the protection of nitrogen gas, and then concentrated under reduced pressure to give a crude product, which was then purified by silica gel column chromatography (mobile phase: petroleum ether:ethyl acetate=100:1 to 20:1) to afford compound BB-1-7.

Step 5: Synthesis of Compound BB-1

To a solution of compound BB-1-7 (46.00 g, 144.97 mmol, 1.00 eq) in dioxane (120.00 mL) was added a solution of hydrochloric acid in dioxane (4 M, 80.00 mL, 2.21 eq) at room temperature. The reaction mixture was stirred at room temperature for 12 h, and then concentrated under reduced pressure to give a crude product. To the crude product was added a mixed solvent of petroleum ether and ethyl acetate (petroleum ether:ethyl acetate=5:1, 100 mL), stirred for 15 minutes, and then filtered. The filter cake was washed with methyl tert-butyl ether (100 mL) to afford compound BB-1. $^1$H NMR (400 MHz, DMSO-d6): δ 7.97 (s, 3H), 2.62-2.66 (m, 1H), 1.51-1.72 (m., 1H), 1.43-1.50 (m., 2H), 1.23 (s, 12H), 0.85 (d, J=6.4 Hz, 6H).

Example 1

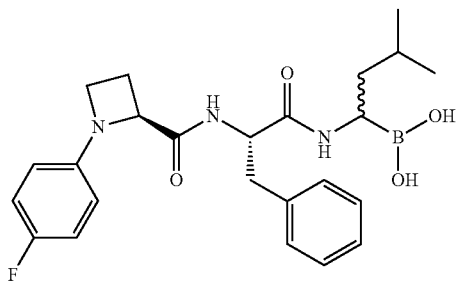 [SMILES: CC(C)CC(NC(=O)[C@H](Cc1ccccc1)NC(=O)[C@@H]1CCN1c1ccc(F)cc1)B(O)O]

Synthetic Route:

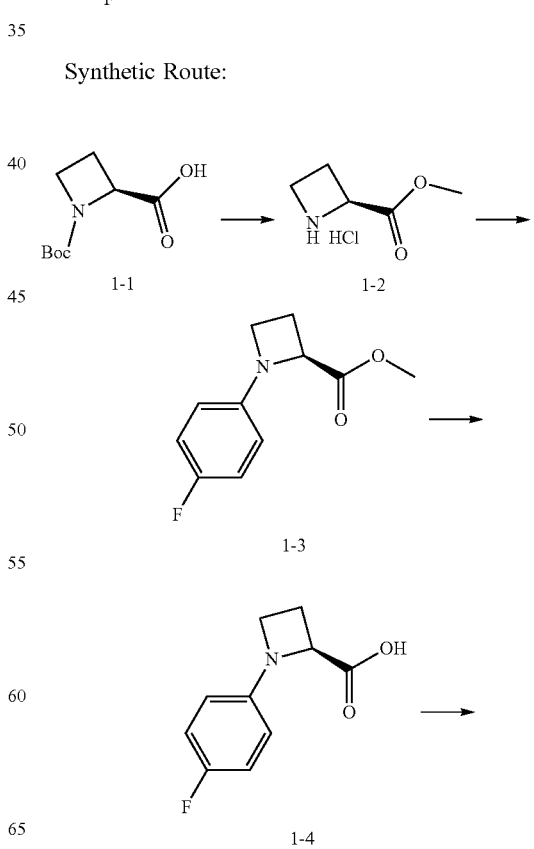

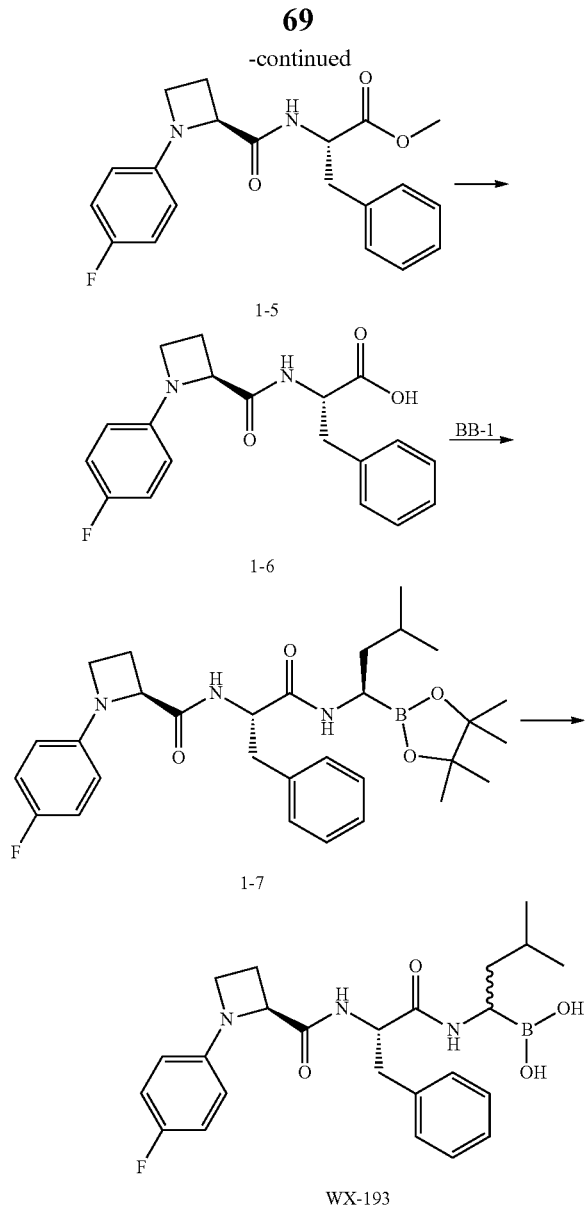

Step 1: Synthesis of Compound 1-2:
To a mixed solution of compound 1-1 (15.00 g, 74.55 mmol, 1.00 eq) and methanol (150.00 mL) was added TMSCl (40.49 g, 372.75 mmol, 47.08 mL, 5.00 eq) at 0° C., and then the reaction mixture was stirred at room temperature for 12 h under the protection of nitrogen gas. The resulting reaction mixture was concentrated under reduced pressure to afford a crude product, i.e., compound 1-2. $^1$H NMR: (400 MHz, METHANOL-$d_4$) δ 5.18 (t, J=9.03 Hz, 1H), 4.15 (q, J=9.29 Hz, 1H), 3.88-4.00 (m, 1H), 3.79-3.86 (m, 3H), 2.60-2.87 (m, 1H), 2.60-2.87 (m, 1H).

Step 2: Synthesis of Compound 1-3:
To a solution of p-fluorophenylboronic acid (2.21 g, 15.83 mmol, 1.20 eq) in acetonitrile (35.00 mL) were added compound 1-2 (2.00 g, 13.19 mmol, 1.00 eq, hydrochloride), 4 A molecular sieve (1.00 g), Cu(OAc)$_2$ (2.64 g, 14.51 mmol, 1.10 eq) and TEA (5.34 g, 52.76 mmol, 7.32 mL, 4.00 eq) at room temperature. The reaction mixture was heated to 80° C. and continuously stirred for 12 h. Then, the reaction mixture was filtered, and the filtrate was concentrated. The resulting residue was purified by silica gel column chromatography (mobile phase: petroleum ether:ethyl acetate=10:1) to afford compound 1-3. $^1$HNMR: (400 MHz, CHLOROFORM-d) δ 6.87-6.97 (m, 2H), 6.44-6.52 (m, 2H), 4.45 (dd, J=7.65, 8.66 Hz, 1H), 4.00 (ddd, J=3.76, 6.78, 8.53 Hz, 1H), 3.82 (s, 3H), 3.62-3.71 (m, 1H), 2.49-2.69 (m, 2H). MS (ESI) m/z: 210.0 [M+1].

Step 3: Synthesis of Compounds 1-4:
To a solution of compound 1-3 (400.00 mg, 1.91 mmol, 1.00 eq) in a mixture of methanol (2.00 mL), tetrahydrofuran (2.00 mL) and water (1.00 mL) was added LiOH.H$_2$O (401.11 mg, 9.56 mmol, 5.00 eq) in an ice bath. The reaction mixture was stirred at room temperature for 1 h and then adjusted to pH=3 with 1N diluted hydrochloric acid. Then the mixture solution was concentrated and extracted with ethyl acetate. The organic phases were combined and concentrated to afford a crude product of compound 1-4, which was directly used in a next step. MS (ESI) m/z: 195.9 [M+1].

Step 4: Synthesis of compound 1-5:
To a solution of compound 1-4 (370.00 mg, 1.90 mmol, 1.00 eq) in DMF (5.00 mL) were added methyl phenylalaninate hydrochloride (491.75 mg, 2.28 mmol, 1.20 eq), TBTU (732.06 mg, 2.28 mmol, 1.20 eq) and DIEA (982.22 mg, 7.60 mmol, 1.33 mL, 4.00 eq) at −10° C. The reaction mixture was stirred at −10° C. to 0° C. for 1 h, and then thereto was added a saturated aqueous solution of ammonium chloride (10 mL). The aqueous phase was extracted with ethyl acetate, and the organic phases were combined, washed with a saturated saline solution, dried over anhydrous sodium sulfate, filtered, and then concentrated. The resulting crude product was purified by silica gel column chromatography (mobile phase: petroleum ether:ethyl acetate=1:1) to afford compound 1-5. $^1$HNMR: (400 MHz, CHLOROFORM-d) δ 7.21-7.33 (m, 4H), 7.13-7.19 (m, 2H), 6.87-6.95 (m, 2H), 6.38-6.46 (m, 2H), 4.88-4.96 (m, 1H), 4.20 (dd, J=7.78, 9.03 Hz, 1H), 3.82 (ddd, J=3.39, 6.96, 8.47 Hz, 1H), 3.71 (s, 3H), 3.60-3.67 (m, 1H), 3.29 (dd, J=5.65, 13.93 Hz, 1H), 3.07 (dd, J=7.78, 14.05 Hz, 1H), 2.45-2.56 (m, 1H), 2.03-2.17 (m, 1H). MS (ESI) m/z: 357.1 [M+1].

Step 5: Synthesis of Compound 1-6
To a solution of compound 1-5 (500.00 mg, 1.40 mmol, 1.00 eq) in a mixture of THF (2.00 mL), MeOH (2.00 mL) and H$_2$O (1.00 mL) was added LiOH.H$_2$O (293.72 mg, 7.00 mmol, 5.00 eq) at room temperature. The reaction mixture was stirred at room temperature for 12 h and then adjusted to pH=3 with 1N diluted hydrochloric acid. The resulting mixture solution was concentrated, and then extracted with ethyl acetate. The organic phases were combined and concentrated to afford a crude product of compound 1-6 which was directly used in a next step. MS (ESI) m/z: 343.1 [M+1].

Step 6: Synthesis of Compound 1-7
To a solution of compound 1-6 (250.00 mg, 730.23 μmol, 1.00 eq) in DMF (5.00 mL) were added compound BB-1 (218.70 mg, 876.27 μmol, 1.20 eq, HCl), TBTU (304.80 mg, 949.29 μmol, 1.30 eq) and DIEA (377.50 mg, 2.92 mmol, 510.13 μL, 4.00 eq) at −10° C. The reaction mixture was stirred at −10° C. to 0° C. for 1 h, and then thereto was added a saturated aqueous solution of ammonium chloride (10 mL). The aqueous phase was extracted with ethyl acetate, and the organic phases were combined, washed with a saturated saline solution, dried over anhydrous sodium sulfate, filtered, and then concentrated to afford a crude product of compound 1-7. MS (ESI) m/z: 538.3 [M+1].

Step 7: Synthesis of Compound WX-193
To a solution of compound 1-7 (390.00 mg, 725.62 μmol, 1.00 eq) in methanol (5.00 mL) were added isobutylboronic acid (517.79 mg, 5.08 mmol, 7.00 eq) and an aqueous solution of HCl (1 M, 51.87 μL, 2.00 eq) in an ice bath. The reaction mixture was warmed to room temperature and continuously stirred for 4 h. The resulting reaction mixture was concentrated under reduced pressure to give a crude product, which was then separated and purified by preparative HPLC (0.225% FA) and then SFC to afford compound WX-193. ¹HNMR: (400 MHz, METHANOL-$d_4$) δ 7.33-7.14 (m, 5H), 6.86 (br t, J=8.7 Hz, 2H), 6.63-6.45 (m, 2H), 4.77 (br t, J=8.0 Hz, 1H), 4.66-4.58 (m, 1H), 4.52-4.41 (m, 1H), 3.17-2.97 (m, 4H), 2.65 (br t, J=7.5 Hz, 1H), 2.24-1.98 (m, 2H), 1.34 (dt, J=6.7, 13.2 Hz, 1H), 1.13 (br t, J=7.4 Hz, 2H), 0.83 (br t, J=6.7 Hz, 6H)0 MS (ESI) m/z: (M−17)438.2.

SFC Separation Method:
Column: AD 250 mm×30 mm, 5 μm
Mobile phase: A: carbon dioxide; B: ethanol (containing 0.1% aqueous ammonia), elution gradient B %: 15%~15%
Flow rate: 50 mL/min
Column temperature: 40° C.
Compound WX-193 was the second peak in high performance chiral liquid column chromatography.

The compounds WX-268, WX-301, WX-351, WX-355, WX-365, WX-373, WX-381 and WX-385 were synthesized by using the same method, and the separation conditions were as follows:

| Compound No. | Compound Structure | MS-17 | ¹HNMR | Separation Conditions |
| --- | --- | --- | --- | --- |
| WX-268 | 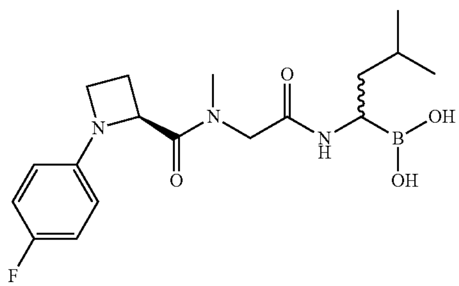 [SMILES: CC(C)CC(NC(=O)CN(C)C(=O)[C@@H]1CCN1c1ccc(F)cc1)B(O)O] | 362.1 | ¹H NMR (400 MHz, METHANOL-d4) δ 6.91 (br s, 2H), 6.49 (br s, 2H), 4.60 (br s, 1H), 4.00-4.40 (m, 1H), 3.50-3.97 (m, 2H), 2.95-3.19 (m, 3H), 2.69 (br s, 1H), 2.49 (br s, 1H), 2.03 (br s, 1H), 1.59 (br s, 3H), 0.93 (br s, 9H) | SFC separation, column: OJ (250 mm * 30 mm, 5 μm); mobile phase: A: carbon dioxide, B: ethanol, elution gradient B%: 15%-15%; flow rate: 60 mL/min, the peak position thereof was the second peak in high performance chiral liquid column chromatography. |
| WX-301 | 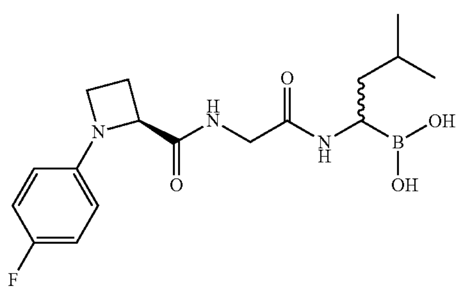 [SMILES: CC(C)CC(NC(=O)CNC(=O)[C@@H]1CCN1c1ccc(F)cc1)B(O)O] | 348.0 | ¹H NMR (400 MHz, METHANOL-d4) δ 6.76-6.93 (m, 2H), 6.63 (br d, J = 4.52 Hz, 2H), 4.59 (br s, 5H), 4.08 (br d, J = 10.29 Hz, 1H), 2.73 (br s, 1H), 2.07-2.40 (m, 2H), 1.52-1.75 (m, 1H), 1.31 (br d, J = 16.81 Hz, 2H), 0.80-0.97 (m, 6H) | SFC separation, Column: AD (250 mm * 30 mm, 10 μm); mobile phase: A: carbon dioxide, B: ethanol, elution gradient B%: 25%-25%; flow rate: 50 mL/min; the peak position thereof was the second peak in high performance chiral liquid column chromatography. |
| WX-351 | 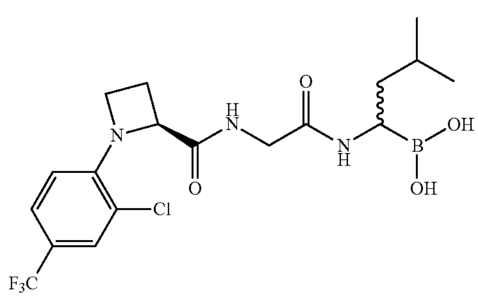 [SMILES: CC(C)CC(NC(=O)CNC(=O)[C@@H]1CCN1c1ccc(C(F)(F)F)cc1Cl)B(O)O] | 432.1 | ¹H NMR (400 MHz, METHANOL-d4) δ 7.38-7.57 (m, 2H), 6.69 (br d, J = 8.53 Hz, 1H), 4.41-4.55 (m, 1H), 4.01-4.18 (m, 3H), 2.59-2.84 (m, 2H), 2.38-2.51 (m, 1H), 1.53-1.73 (m, 1H), 1.27-1.43 (m, 2H), 0.92 (d, J = 6.78 Hz, 6H) | Preparative HPLC separation, column: Xtimate C18 150 * 25 mm, 5 μm; mobile phase: A: water (0.225% FA), B: methanol, elution gradient B%: 70%-100%, the retention time thereof was 13 min in high performance liquid column chromatography. |
| WX-355 | 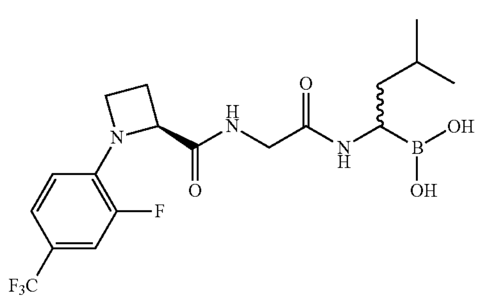 [SMILES: CC(C)CC(NC(=O)CNC(=O)[C@@H]1CCN1c1ccc(C(F)(F)F)cc1F)B(O)O] | 416.1 | ¹H NMR (400 MHz, METHANOL-d4) δ 7.16-7.42 (m, 2H), 6.59-6.80 (m, 1H), 4.56-4.77 (m, 1H), 3.96-4.33 (m, 4H), 2.42-2.81 (m, 3H), 1.64 (br dd, J = 6.53, 13.55 Hz, 1H), 1.20-1.48 (m, 2H), 0.92 (br d, J = 5.52 Hz, 6H) | Preparative HPLC separation, column: Xtimate C18 150 * 25 mm, 5 μm; mobile phase: A: water (0.225% FA), B: acetonitrile, elution gradient B%: 75%-85%, the retention time thereof was 13.0 min in high performance liquid column chromatography. |

-continued

| Compound No. | Compound Structure | MS-17 | ¹HNMR | Separation Conditions |
|---|---|---|---|---|
| WX-365 | 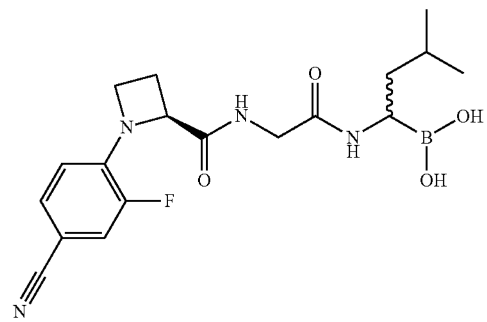 [SMILES: CC(C)CC(NC(=O)CNC(=O)[C@@H]1CCN1c1ccc(C#N)cc1F)B(O)O] | 372.9 | ¹H NMR (400 MHz, METHANOL-d4) δ 7.28-7.44 (m, 2H), 6.64 (t, J = 8.78 Hz, 1H), 4.73-4.80 (m, 2H), 3.96-4.32 (m, 4H), 2.62-2.81 (m, 2H), 2.38-2.57 (m, 1H), 1.64 (qd, J = 6.86, 13.55 Hz, 1H), 1.23-1.43 (m, 2H), 0.93 (d, J = 6.53 Hz, 6H) | SFC separation, column: AS (250 mm * 30 mm, 5 μm); mobile phase: A: carbon dioxide, B: ethanol, elution gradient B%: 15%-15%; the peak position thereof was the second peak in high performance chiral liquid column chromatography. |
| WX-373 | 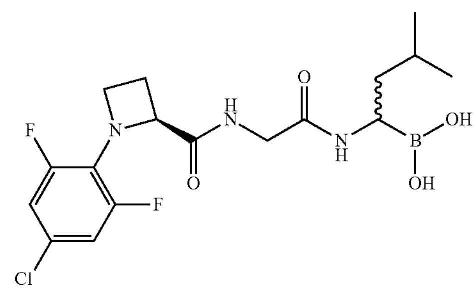 [SMILES: CC(C)CC(NC(=O)CNC(=O)[C@@H]1CCN1c1c(F)cc(Cl)cc1F)B(O)O] | 400.1 | ¹H NMR (400 MHz, METHANOL-d4) δ 6.81-7.05 (m, 2H), 4.30-4.43 (m, 1H), 3.94-4.35 (m, 4H), 2.52-2.81 (m, 2H), 2.32-2.50 (m, 1H), 1.64 (qd, J = 6.72, 13.46 Hz, 1H), 1.26-1.49 (m, 2H), 0.93 (dd, J = 2.26, 6.53 Hz, 6H) | Preparative HPLC separation, Column: Xtimate C18 150 * 25 mm, 5 μm; mobile phase: A: water (0.225% FA), B: methanol, elution gradient B%: 72%-82%, the retention time thereof was 12.0 min in high performance liquid column chromatography. |
| WX-381 | 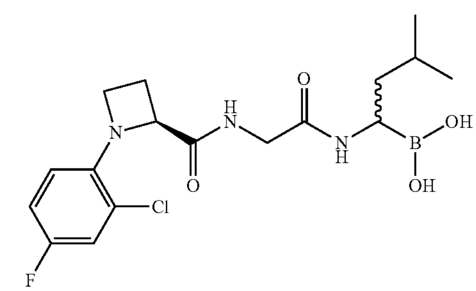 [SMILES: CC(C)CC(NC(=O)CNC(=O)[C@@H]1CCN1c1ccc(F)cc1Cl)B(O)O] | 381.9 | ¹H NMR (400 MHz, METHANOL-d4) δ 7.08 (dd, J = 2.76, 8.28 Hz, 1H), 6.88-7.00 (m, 1H), 6.61 (dd, J = 5.02, 9.03 Hz, 1H), 4.60 (br t, J = 8.28 Hz, 1H), 4.30-4.43 (m, 1H), 4.03-4.17 (m, 2H), 3.79 (q, J = 7.86 Hz, 1H), 2.35-2.79 (m, 3H), 1.56-1.73 (m, 1H), 1.25-1.40 (m, 2H), 0.91 (d, J = 6.53 Hz, 7H) | Preparative HPLC separation, Column: Xtimate C18 150 * 25 mm, 5 μm; mobile phase: A: water (0.225% FA), B: methanol, elution gradient B%: 65%-85%, the retention time thereof was 13.0 min in high performance liquid column chromatography. |
| WX-385 | 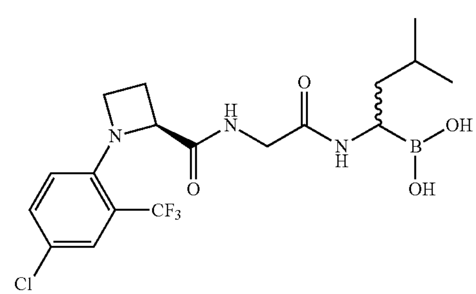 [SMILES: CC(C)CC(NC(=O)CNC(=O)[C@@H]1CCN1c1ccc(Cl)cc1C(F)(F)F)B(O)O] | 432.1 | ¹H NMR (400 MHz, METHANOL-d4) δ 7.29-7.59 (m, 2H), 6.62 (d, J = 9.03 Hz, 1H), 4.54-4.78 (m, 1H), 4.26 (br s, 1H), 3.84-4.15 (m, 3H), 2.52-2.82 (m, 2H), 2.32-2.49 (m, 1H), 1.63 (td, J = 6.71, 13.18 Hz, 1H), 1.23-1.42 (m, 2H), 0.91 (br d, J = 6.27 Hz, 6H) | Preparative HPLC separation, Column: Xtimate C18 150 * 25 mm, 5 μm; mobile phase: A: water (0.225% FA), B: methanol, elution gradient B%: 70%-100%, the retention time thereof was 9.5 min in high performance liquid column chromatography. |

Example 2

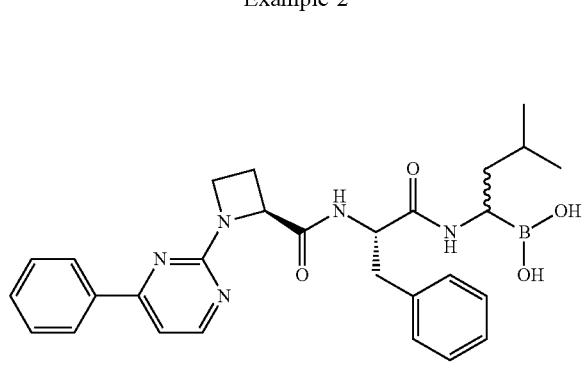

Synthetic Route:

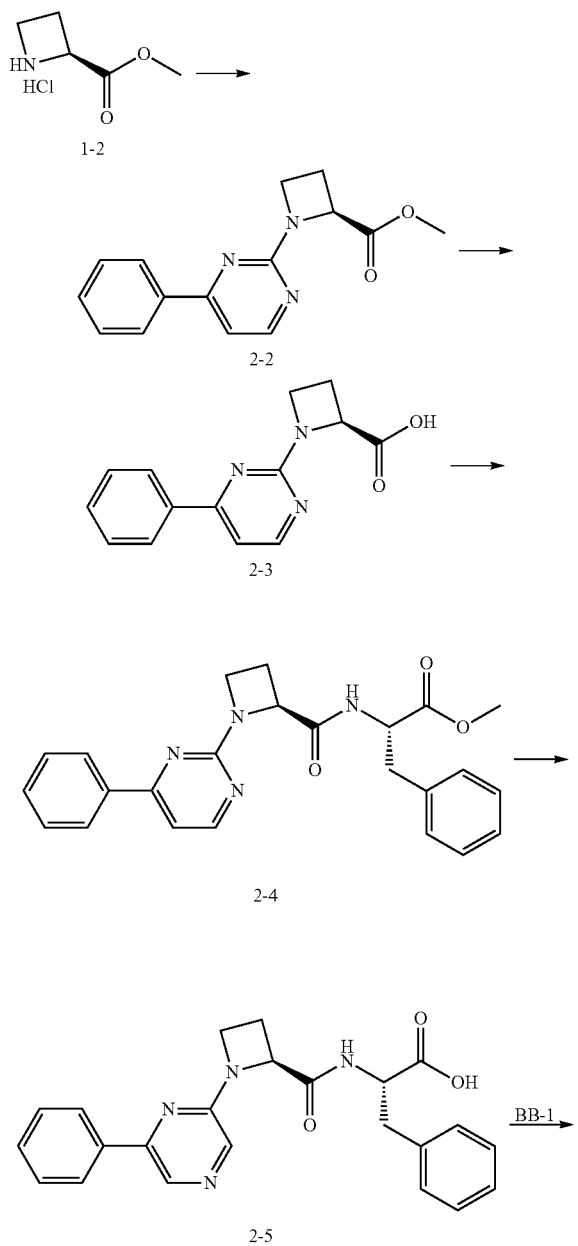

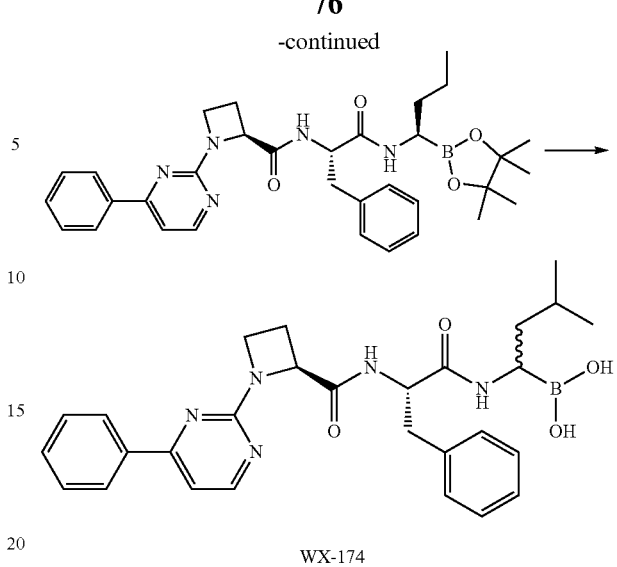

Step 1: Synthesis of Compound 2-2

To a solution of compound 1-2 (1.00 g, 6.60 mmol, 1.00 eq) and 2-chloro-4-phenyl-pyrimidine (1.26 g, 6.60 mmol, 1.00 eq) in EtOH (20.00 mL) were added DIPEA (2.56 g, 19.80 mmol, 3.46 mL, 3.00 eq) and $Na_2CO_3$ (2.10 g, 19.80 mmol, 3.00 eq) at room temperature. The reaction mixture was heated to 40° C. and stirred for 12 h. Then the solvent was removed by rotary evaporation under reduced pressure, and the residue was diluted with water (20 mL) and then extracted with ethyl acetate. The organic phases were combined, washed with a saturated saline solution, dried over anhydrous sodium sulfate, filtered, and then concentrated. The resulting residue was separated by preparative chromatography (mobile phase: petroleum ether/ethyl acetate=5/1) to afford compound 2-2. MS (ESI) m/z: 269.9 [M+1].

Step 2: Synthesis of Compound 2-3

To a solution of compound 2-2 (150.00 mg, 0.56 mmol, 1.00 eq) in a mixture of MeOH (3.00 mL) and $H_2O$ (0.50 mL) was added $LiOH.H_2O$ (23.37 mg, 0.57 mmol, 1.00 eq) at room temperature. The reaction mixture was stirred at room temperature for 4 h, and then adjusted to pH=6-7 with 1N diluted hydrochloric acid. The resulting mixture solution was concentrated to afford a crude product of compound 2-3, which was directly used in a next step. MS (ESI) m/z: 255.9 [M+1].

Step 3: Synthesis of Compound 2-4

To a solution of compound 2-3 (150.00 mg, 0.59 mmol, 1.00 eq) in DMF (2.00 mL) were added methyl phenylalaninate hydrochloride (126.37 mg, 0.71 mmol, 1.20 eq), TBTU (377.34 mg, 1.18 mmol, 2.00 eq) and DIPEA (303.77 mg, 2.35 mmol, 0.41 mL, 4.00 eq) at −20° C. The reaction mixture was stirred at −20° C. to 0° C. for 2 h, and then thereto was added water (10 mL). The aqueous phase was extracted with ethyl acetate, and the organic phases were combined, washed with a saturated saline solution, dried over anhydrous sodium sulfate, filtered, and then concentrated to give a crude product, which was then separated and purified by preparative chromatography (mobile phase: petroleum ether:ethyl acetate=2:1) to afford compound 2-4.

Step 4: Synthesis of Compound 2-5

To a solution of compound 2-4 (250.00 mg, 600.28 μmol, 1.00 eq) in a mixture of water (1.00 mL) and MeOH (2.00 mL) was added $LiOH.H_2O$ (75.56 mg, 1.80 mmol, 3.00 eq) at room temperature. The reaction mixture was stirred at room temperature for 12 h and then adjusted to about pH=3 with 1N diluted hydrochloric acid. The resulting mixture solution was concentrated, and extracted with ethyl acetate. The organic phases were combined, and concentrated to afford a crude product of compound 2-5, which was directly used in a next step. MS (ESI) m/z: 403.5 [M+1].

Step 5: Synthesis of Compound 2-6

To a solution of compound 2-5 (260.00 mg, 646.06 μmol, 1.00 eq) in DMF (5.00 mL) were added compound BB-1 (193.49 mg, 775.27 μmol, 1.20 eq), TBTU (311.15 mg, 969.09 μmol, 1.50 eq) and DIPEA (333.99 mg, 2.58 mmol, 451.33 μL, 4.00 eq) at −10° C. The reaction mixture was stirred at −10° C. to 0° C. for 1 h, and then thereto was added a saturated aqueous solution of ammonium chloride (10 mL). The aqueous phase was extracted with ethyl acetate, and the organic phases were combined, washed with a saturated saline solution, dried over anhydrous sodium sulfate, filtered, and then concentrated to afford a crude product of compound 2-6. MS (ESI) m/z: 599.2 [M+1].

Step 6: Synthesis of Compound WX-174

To a solution of compound 2-6 (380.00 mg, 634.88 μmol, 1.00 eq) in MeOH (3.00 mL) were added isobutylboric acid (478.92 mg, 4.70 mmol, 7.40 eq) and an aqueous solution of HCl (1 M, 1.27 mL, 2.00 eq) at 0° C. The reaction mixture was stirred at 0° C. to 20° C. for 1 h, and then concentrated under reduced pressure to give a crude product, which was then separated by preparative HPLC (0.225% FA) to afford compound WX-174. $^1$HNMR (400 MHz, METHANOL-d4) δ 8.38 (br d, J=5.3 Hz, 1H), 8.21-8.03 (m, 2H), 7.59-7.45 (m, 3H), 7.36-7.05 (m, 6H), 4.20-3.95 (m, 2H), 3.23-2.93 (m, 2H), 2.67-2.44 (m, 2H), 2.23 (br s, 1H), 1.49-1.07 (m, 3H), 0.83 (br t, J=6.0 Hz, 6H). MS (ESI) m/z: 497.9 [M−17].

SFC Analysis Method of WX-174:

Column: AS 150 mm×4.6 mm, 5 μm

Mobile phase: A: carbon dioxide; B: ethanol (containing 0.05% diethanolamine), elution gradient B %: 5%~40%

Flow rate: 3 mL/min

Column temperature: 40° C.

The retention time of compound WX-174 was 2.592 min in high performance chiral liquid column chromatography.

Compounds WX-260, WX-306, WX-308, WX-311, WX-313, WX-317, WX-319, WX-327, WX-329, WX-367, WX-379, WX-387 and WX-393 were synthesized by using the same method, and their separation conditions were as follows:

| Compound No. | Compound Structure | MS-17 | $^1$HNMR | Separation Conditions |
|---|---|---|---|---|
| WX-260 | 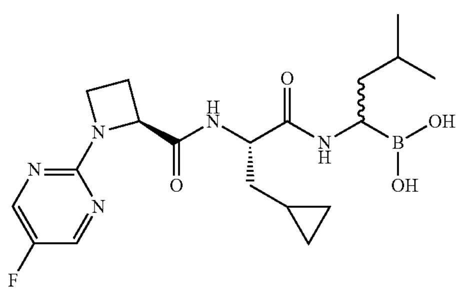 [SMILES: CC(C)CC(NC(=O)[C@H](CC1CC1)NC(=O)[C@@H]1CCN1c1ncc(F)cn1)B(O)O] | 404.2 | $^1$H NMR (400 MHz, METHANOL-d4) δ 8.17 (s, 2H), 4.52-4.66 (m, 2H), 3.88-3.95 (m, 2H), 3.15 (td, J = 1.54, 3.20 Hz, 1H), 2.24-2.60 (m, 3H), 1.61-1.76 (m, 1H), 1.43-1.55 (m, 2H), 1.12-1.23 (m, 2H), 0.76 (d, J = 6.53 Hz, 6H), 0.56-0.67 (m, 1H), 0.24-0.41 (m, 2H), −0.08-0.06 (m, 2H). | Preparative HPLC separation, Column: Xtimate C18 150 mm * 25 mm, 5 μm; mobile phase: A: water (0.225% FA), B: methanol, elution gradient B%: 60%-80%, the retention time thereof was 7.0 min in high performance liquid column chromatography. |
| WX-306 | 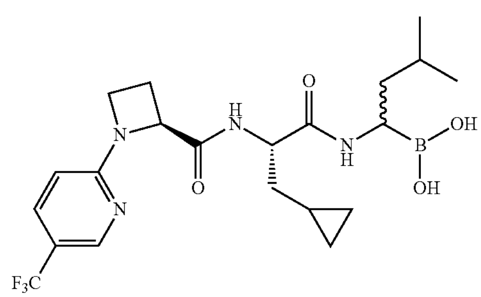 [SMILES: CC(C)CC(NC(=O)[C@H](CC1CC1)NC(=O)[C@@H]1CCN1c1ccc(C(F)(F)F)cn1)B(O)O] | 452.9 | $^1$H NMR (400 MHz, METHANOL-d$_4$) δ 8.35 (s, 1H), 7.98-8.12 (m, 1H), 6.86 (d, J = 9.29 Hz, 1H), 5.11-5.24 (m, 1H), 4.61-4.73 (m, 1H), 4.18-4.41 (m, 2H), 2.83-2.97 (m, 1H), 2.75 (br dd, J = 6.27, 8.78 Hz, 1H), 2.48-2.62 (m, 1H), 1.81-1.92 (m, 1H), 1.58-1.72 (m, 2H), 1.26-1.42 (m, 2H), 0.89-0.96 (m, 6H), 0.74-0.87 (m, 1H), 0.43-0.59 (m, 2H), 0.13-0.24 (m, 2H) | Preparative HPLC separation, Column: Phenomenex Synergi C18 (150 mm * 30 mm, 4 μm); mobile phase: A: water (0.225% FA), B: methanol), elution gradient B%: 70%-85%, 10 min); flow rate: 25 mL/min, the retention time thereof was 2.8 min in high performance liquid column chromatography. |
| WX-308 | 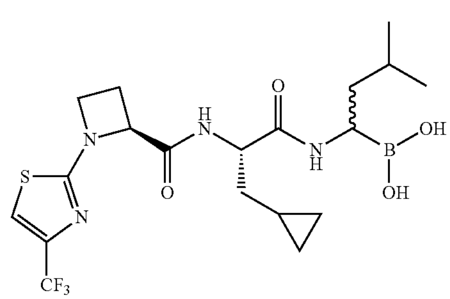 [SMILES: CC(C)CC(NC(=O)[C@H](CC1CC1)NC(=O)[C@@H]1CCN1c1nc(C(F)(F)F)cs1)B(O)O] | 459.1 | $^1$H NMR (400 MHz, METHANOL-d4) δ 7.38 (s, 1H), 4.84 (br s, 1H), 4.69 (t, J = 7.28 Hz, 1H), 4.08-4.19 (m, 1H), 4.03 (q, J = 7.61 Hz, 1H), 2.67-2.79 (m, 2H), 2.51-2.65 (m, 1H), 1.78-1.90 (m, 1H), 1.58-1.72 (m, 2H), 1.31-1.38 (m, 2H), 0.90-0.94 (m, 6H), 0.73-0.85 (m, 1H), 0.40-0.57 (m, 2H), 0.11-0.20 (m, 2H) | Preparative HPLC separation, Column: Phenomenex Synergi C18 (150 mm * 30 mm, 4 μm); mobile phase: A: water (0.225% FA), B: methanol, elution gradient B%: 70%-85%, 10 min); flow rate: 25 mL/min, the retention time thereof was 2.8 min in high performance liquid column chromatography. |

| Compound No. | Compound Structure | MS-17 | ¹HNMR | Separation Conditions |
|---|---|---|---|---|
| WX-311 | 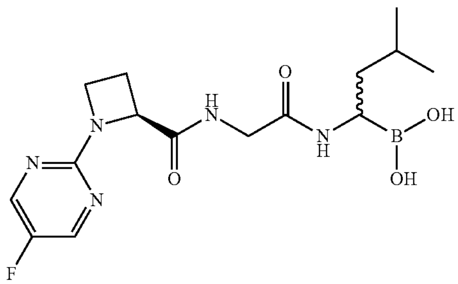 [SMILES: CC(C)CC(NC(=O)CNC(=O)[C@@H]1CCN1c1ncc(F)cn1)B(O)O] | 350.2 | ¹H NMR (400 MHz, METHANOL-d₄) δ 8.35 (s, 2H), 4.76 (dd, J = 6.78, 9.29 Hz, 1H), 4.03-4.17 (m, 4H), 2.74 (br t, J = 7.65 Hz, 1H), 2.57-2.69 (m, 1H), 2.46 (qd, J = 7.72, 10.98 Hz, 1H), 1.59-1.71 (m, 1H), 1.31-1.41 (m, 2H), 0.92 (d, J = 6.53 Hz, 6H) | Preparative HPLC separation, Column: Phenomenex Synergi C18 150 mm * 30 mm, 4 μm; mobile phase: A: water (0.225% FA), B: methanol, elution gradient B%: 50%-75%, the retention time thereof was 7.5 min in high performance liquid column chromatography. |
| WX-313 | 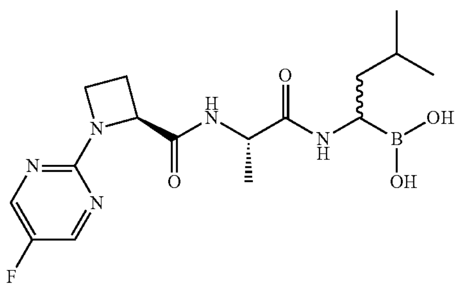 [SMILES: CC(C)CC(NC(=O)[C@H](C)NC(=O)[C@@H]1CCN1c1ncc(F)cn1)B(O)O] | 364.1 | ¹H NMR (400 MHz, METHANOL-d4) δ 8.36 (s, 2H), 4.61-4.84 (m, 2H), 4.05-4.16 (m, 2H), 2.38-2.80 (m, 3H), 1.61-1.73 (m, 1H), 1.48 (d, J = 7.28 Hz, 3H), 1.29-1.40 (m, 2H), 0.95 (d, J = 6.53 Hz, 7H). | SFC separation, Column: AD (250 mm * 30 mm, 5 μm); Mobile phase: A: carbon dioxide, B: ethanol, elution gradient B%: 15%-15%; the peak position thereof was the second peak in high performance chiral liquid column chromatography. |
| WX-317 | 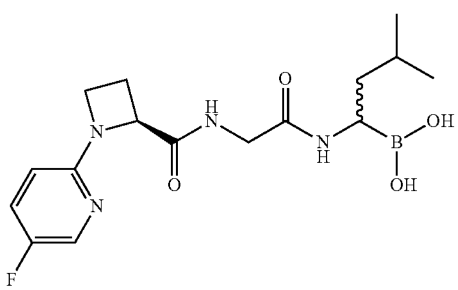 [SMILES: CC(C)CC(NC(=O)CNC(=O)[C@@H]1CCN1c1ccc(F)cn1)B(O)O] | 349.1 | ¹H NMR (400 MHz, METHANOL-d4) δ 7.98 (br s, 1H), 7.47 (dt, J = 2.89, 8.60 Hz, 1H), 6.57 (dd, J = 3.51, 9.03 Hz, 1H), 4.64 (br t, J = 8.28 Hz, 1H), 4.05-4.25 (m, 2H), 3.90 (q, J = 7.86 Hz, 1H), 2.74 (br s, 1H), 2.42-2.67 (m, 2H), 1.57-1.75 (m, 1H), 1.36 (br t, J = 7.03 Hz, 2H), 1.15 (d, J = 6.27 Hz, 1H), 0.93 (br d, J = 6.53 Hz, 6H) | SFC separation, Column: Chiralpak AS-H 250 mm * 30 mm, 5 μm; mobile phase: A: carbon dioxide, B: ethanol (containing 0.1% NH₃•H₂O), elution gradient B%: 20%-20%; the peak position thereof was the second peak in high performance chiral liquid column chromatography. |
| WX-319 | 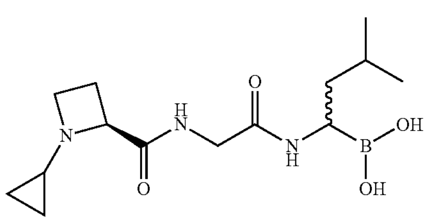 [SMILES: CC(C)CC(NC(=O)CNC(=O)[C@@H]1CCN1C1CC1)B(O)O] | 294.1 | ¹H NMR (400 MHz, METHANOL-d4) δ 4.03-4.25 (m, 2H), 3.87-3.98 (m, 1H), 3.42-3.52 (m, 1H), 2.76 (br s, 1H), 2.33-2.46 (m, 1H), 2.05-2.22 (m, 2H), 1.58-1.78 (m, 1H), 1.30-1.46 (m, 3H), 1.16-1.24 (m, 1H), 0.88-0.99 (m, 6H), 0.39-0.65 (m, 4H). | Preparative HPLC separation, Column: DuraShell 150 mm * 25 mm, 5 μm; mobile phase: A: water (0.225% FA), B: acetonitrile, elution gradient B%: 0%-30%, the retention time thereof was 6.5 min in high performance liquid column chromatography. |
| WX-327 | 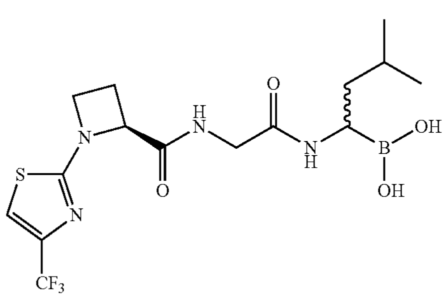 [SMILES: CC(C)CC(NC(=O)CNC(=O)[C@@H]1CCN1c1nc(C(F)(F)F)cs1)B(O)O] | 405.1 | ¹H NMR (400 MHz, METHANOL-d₄) δ 7.43 (s, 1H), 4.84 (br s, 1H), 4.00-4.27 (m, 4H), 2.47-2.91 (m, 3H), 1.69 (td, J = 6.62, 13.11 Hz, 1H), 1.28-1.47 (m, 2H), 0.94 (br d, J = 6.27 Hz, 6H). | Preparative HPLC separation, Column: Phenomenex Synergi C18 150 mm * 30 mm, 4 μm; mobile phase: A: water (0.225% FA), B: methanol, elution gradient B%: 50%-75%, the retention time thereof was 9.4 min in high performance liquid column chromatography. |

| Compound No. | Compound Structure | MS-17 | ¹HNMR | Separation Conditions |
|---|---|---|---|---|
| WX-329 | 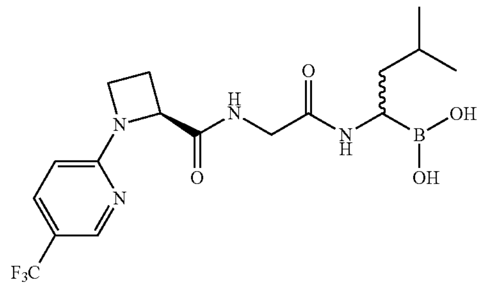 [SMILES: CC(C)CC(NC(=O)CNC(=O)[C@@H]1CCN1c1ccc(C(F)(F)F)cn1)B(O)O] | 399.1 | ¹H NMR (400 MHz, METHANOL-d4) δ 8.36 (br s, 1H), 7.83 (br d, J = 8.78 Hz, 1H), 6.63 (br d, J = 8.78 Hz, 1H), 4.77-4.84 (m, 1H), 4.01-4.26 (m, 4H), 2.49-2.84 (m, 3H), 1.68 (br dd, J = 6.40, 12.92 Hz, 1H), 1.24-1.47 (m, 2H), 0.94 (br d, J = 6.27 Hz, 6H) | Preparative HPLC separation, Column: Phenomenex Synergi C18 150 mm * 30 mm, 4 μm; mobile phase: A: water (0.225% FA), B: methanol, elution gradient B%: 55%-80%, the retention time thereof was 9.2 min in high performance liquid column chromatography. |
| WX-367 | 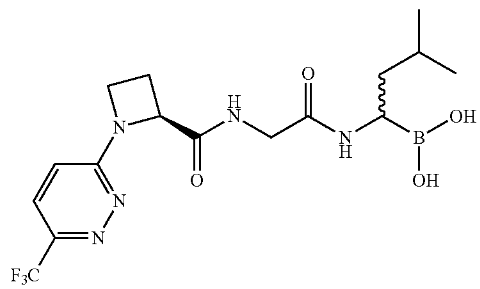 [SMILES: CC(C)CC(NC(=O)CNC(=O)[C@@H]1CCN1c1ccc(C(F)(F)F)nn1)B(O)O] | 400.1 | ¹H NMR (400 MHz, METHANOL-d4) δ 7.77 (dd, J = 2.38, 9.41 Hz, 1H), 7.03 (d, J = 9.29 Hz, 1H), 4.95-5.06 (m, 1H), 4.07-4.29 (m, 4H), 2.53-2.86 (m, 3H), 1.61-1.80 (m, 1H), 1.27-1.49 (m, 2H), 0.86-1.00 (m, 6H) | Preparative HPLC separation, Column: Xtimate C18 150 mm * 25 mm, 5 μm; mobile phase: A: water (0.225% FA), B: methanol, elution gradient B%: 55%-85%, the retention time thereof was 13.0 min in high performance liquid column chromatography. |
| WX-379 | 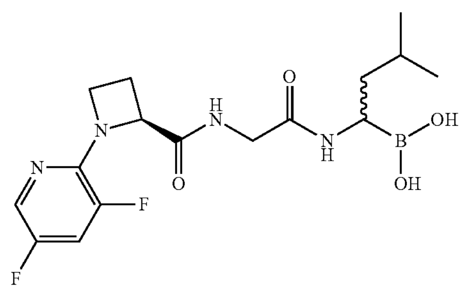 [SMILES: CC(C)CC(NC(=O)CNC(=O)[C@@H]1CCN1c1ncc(F)cc1F)B(O)O] | 367.1 | ¹H NMR (400 MHz, METHANOL-d4) δ 7.89 (br s, 1H), 7.43 (br t, J = 9.54 Hz, 1H), 4.78-4.83 (m, 1H), 3.96-4.24 (m, 4H), 2.74 (br s, 1H), 2.63 (br d, J = 7.03 Hz, 1H), 2.46-2.58 (m, 1H), 1.65 (br d, J = 6.02 Hz, 1H), 1.35 (br t, J = 6.90 Hz, 2H), 0.92 (br d, J = 5.77 Hz, 6H) | Preparative HPLC separation, Column: Xtimate C18 (150 mm * 25 mm, 5 μm); mobile phase: A: carbon dioxide, B: ethanol, elution gradient B%: 55%-85%, 9.5 min); flow rate: 25 mL/min, the retention time thereof was 4.0 min in high performance liquid column chromatography. |
| WX-387 | 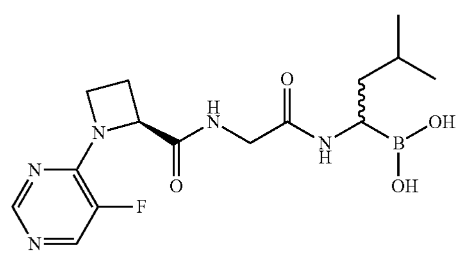 [SMILES: CC(C)CC(NC(=O)CNC(=O)[C@@H]1CCN1c1ncncc1F)B(O)O] | 350.1 | ¹H NMR (400 MHz, METHANOL-d4) δ 8.28 (br s, 1H), 7.98-8.16 (m, 2H), 4.93-5.10 (m, 1H), 4.32 (br d, J = 5.52 Hz, 2H), 4.01-4.23 (m, 2H), 2.70-2.84 (m, 1H), 2.37-2.67 (m, 2H), 1.53-1.72 (m, 1H), 1.20-1.42 (m, 2H), 0.88 (d, J = 6.53 Hz, 6H) | Preparative HPLC separation, Column: Xtimate C18 150 mm * 25 mm, 5 μm; mobile phase: A: water (0.225% FA), B: methanol, elution gradient B%: 21%-51%, the retention time thereof was 13.0 min in high performance liquid column chromatography. |
| WX-393 | 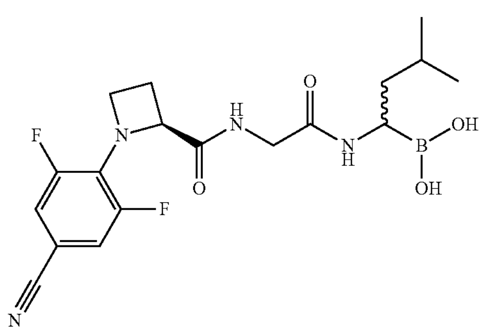 [SMILES: CC(C)CC(NC(=O)CNC(=O)[C@@H]1CCN1c1c(F)cc(C#N)cc1F)B(O)O] | 391.1 | ¹H NMR (400 MHz, METHANOL-d4) δ 8.08 (br s, 1H), 7.17-7.38 (m, 2H), 5.06 (dt, J = 3.39, 6.21 Hz, 1H), 4.23-4.53 (m, 2H), 4.11 (s, 2H), 2.30-2.84 (m, 3H), 1.56-1.75 (m, 1H), 1.23-1.45 (m, 2H), 0.80-1.03 (m, 6H) | Preparative HPLC separation, Column: Xtimate C18 150 mm * 25 mm, 5 μm; mobile phase: A: water (0.225% FA), B: methanol, elution gradient B%: 64%-74%, the retention time thereof was 12.0 min in high performance liquid column chromatography. |

Example 3

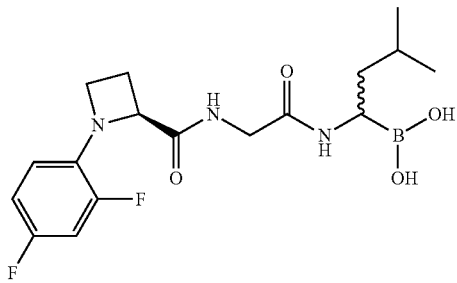 [SMILES: CC(C)CC(NC(=O)CNC(=O)[C@@H]1CCN1c1ccc(F)cc1F)B(O)O]

Synthetic Route:

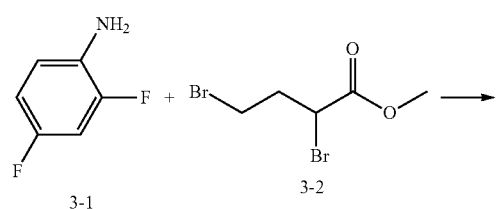

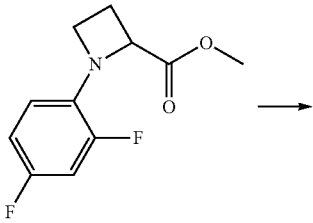

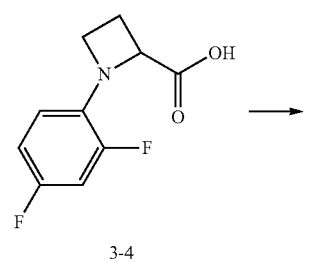

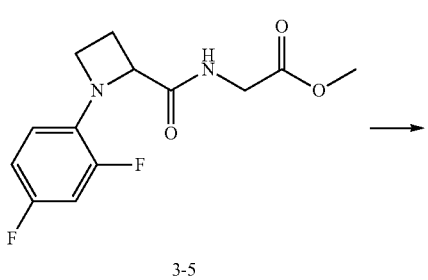

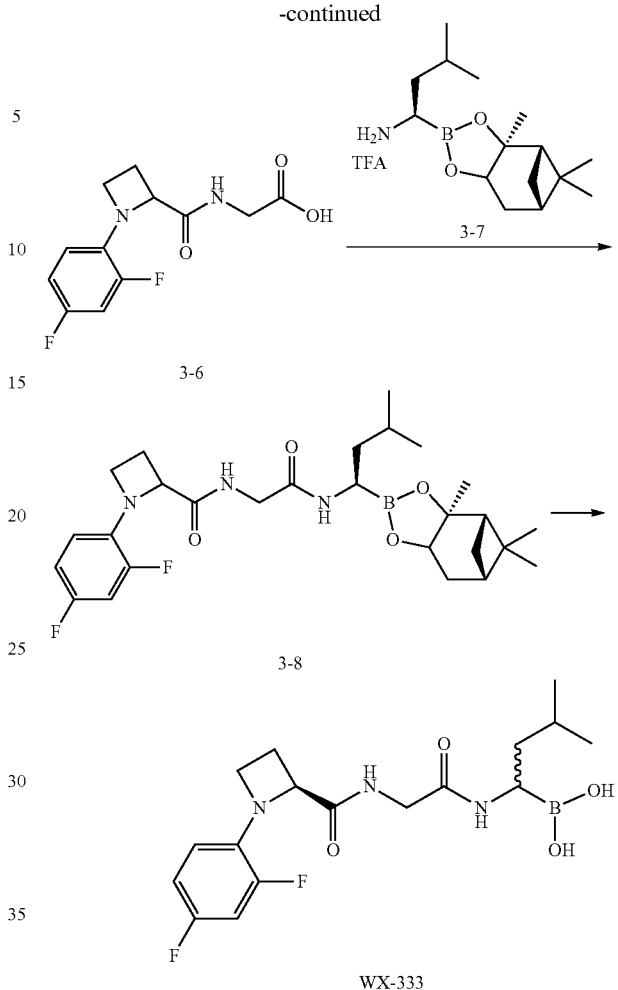

WX-333

Step 1: Synthesis of Compound 3-3

To a solution of compound 3-1 (10 g, 77.46 mmol, 1.00 eq) and compound 3-2 (20.13 g, 77.46 mmol, 1.00 eq) in acetonitrile (200 mL) was added N,N-diisopropylethylamine (22.02 g, 170.40 mmol, 2.20 eq) at room temperature. The reaction mixture was stirred at 100° C. for 16 h, then cooled to room temperature and subsequently added to ethyl acetate. The organic layer was washed sequentially with water and a saturated saline solution, dried over anhydrous sodium sulfate, and filtered. The filtrate was concentrated, and then purified by silica gel column chromatography (mobile phase: petroleum ether:ethyl acetate=10:1) to afford compound 3-3. MS (ESI) m/z: 227.9 [M+1].

Step 2: Synthesis of Compound 3-4

To a solution of compound 3-3 (7.2 g, 31.69 mmol, 1.00 eq) in a mixture of methanol (20 mL), tetrahydrofuran (20 mL) and water (10 mL) was added LiOH.H$_2$O (6.65 g, 158.45 mmol, 5.00 eq) at 0° C. The reaction mixture was stirred at room temperature for 1 h, and then concentrated under reduced pressure, diluted with water and ethyl acetate, and layered. The aqueous layer was adjusted to pH=6 with 1N hydrochloric acid and then extracted with ethyl acetate. The organic phase was combined and washed with a saturated saline solution, dried over anhydrous sodium sulfate and filtered. The filtrate was concentrated to afford compound 3-4, which was directly used in a next step. MS (ESI) m/z: 213.9 [M+1].

Step 3: Synthesis of Compound 3-5

To a solution of compound 3-4 (1.5 g, 7.04 mmol, 1.00 eq) in dichloromethane (50 mL) were added glycine methyl ester hydrochloride (1.06 g, 8.44 mmol, 1.20 eq, hydrochloride), TBTU (2.71 g, 8.44 mmol, 1.20 eq) and N,N-diisopropylethylamine (3.64 g, 28.15 mmol, 4.90 mL, 4.00 eq) at −10° C. The reaction mixture was stirred at −10° C. to 0° C. for 3 h, and then diluted with water (40 mL) and extracted with dichloromethane. The organic phase was combined and washed with a saturated saline solution, dried over anhydrous sodium sulfate and filtered. The filtrate was concentrated, and then purified by silica gel column chromatography (mobile phase: petroleum ether:ethyl acetate=5:1) to afford compound 3-5. MS (ESI) m/z: 284.9 [M+1].

Step 4: Synthesis of compound 3-6:

To a solution of compound 3-5 (0.5 g, 1.76 mmol, 1.00 eq) in a mixture of tetrahydrofuran (2 mL), methanol (2 mL) and water (1 mL) was added LiOH.H$_2$O (369.03 mg, 8.79 mmol, 5.00 eq) at 0° C. The reaction mixture was stirred at 0° C. to 20° C. for 2 h, and then concentrated, diluted with water (3 mL) and layered. The aqueous layer was adjusted to pH=6 with 1N hydrochloric acid and then extracted with ethyl acetate. The organic phase was combined and washed with a saturated saline solution, dried over anhydrous sodium sulfate and filtered. The filtrate was concentrated to give compound 3-6, which was directly used in a next step. MS (ESI) m/z: 270.9 [M+1]

Step 5: Synthesis of Compound 3-8

To a solution of compound 3-6 (0.26 g, 962.14 μmol, 1.00 eq), compound 3-7 (437.84 mg, 1.15 mmol, 1.20 eq) and TBTU (370.71 mg, 1.15 mmol, 1.20 eq) in dichloromethane (10 mL) was added N,N-diisopropylethylamine (273.56 mg, 2.12 mmol, 2.20 eq) at −10° C. The reaction mixture was slowly warmed to room temperature and continuously stirred for 2 h. The reaction mixture was then diluted with water (10 mL) and extracted with dichloromethane. The organic phase was combined and washed with a saturated saline solution, dried over anhydrous sodium sulfate and filtered. The filtrate was concentrated and then purified by silica gel column chromatography (mobile phase: petroleum ether:ethyl acetate=1:1) to afford compound 3-8. MS (ESI) m/z: 518.2 [M+1]

Step 6: Synthesis of Compound WX-333

To a solution of compound 3-8 (0.17 g, 328.56 μmol, 1.00 eq) in a mixture of methanol (4 mL) and n-hexane (6 mL) were added isobutylboric acid (234.45 mg, 2.30 mmol, 7.00 eq) and 1 M HCl (1.31 mL, 4.00 eq) at 0° C. The reaction mixture was slowly warmed to room temperature, continuously stirred for 12 h and then concentrated under reduced pressure to give a residue. The residue was purified by preparative HPLC and then separated by SFC to afford compound WX-333. $^1$H NMR (400 MHz, METHANOL-d4) δ 6.83 (br s, 2H), 6.61 (br s, 1H), 4.49 (br s, 1H), 4.10 (br s, 3H), 3.84 (br s, 1H), 2.75 (br s, 1H), 2.59 (br s, 1H), 2.48 (br s, 1H), 1.62 (br s, 1H), 1.30 (br s, 2H), 0.92 (br s, 6H). MS (ESI) m/z: 366.1 [M−17].

Preparative HPLC Separation Method of WX-333:

Column: Xtimate C18 150×25 mm, 5 μm;

Mobile phase: water (0.225% FA)-MeOH

Retention time: 9.5 min

Preparative SFC Separation Method of WX-333:

Column: C2 250 mm×30 mm, 10 μm

Mobile phase: A: carbon dioxide; B: methanol, elution gradient B %: 30%-30%

Flow rate: 60 mL/min

The peak position of compound WX-333 was the second peak in high performance chiral liquid column chromatography.

Compound WX-391 was synthesized by using the same method, and its separation conditions were as follows:

| Compound No. | Compound Structure | MS-17 | $^1$HNMR | Separation Conditions |
|---|---|---|---|---|
| WX-391 | 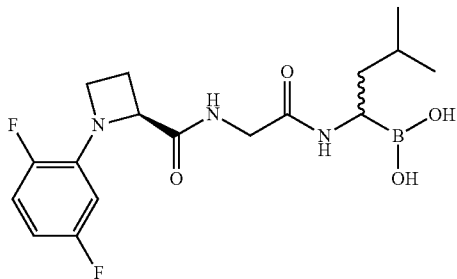 [SMILES: CC(C)CC(NC(=O)CNC(=O)[C@@H]1CCN1c1cc(F)ccc1F)B(O)O] | 384.1 | $^1$H NMR (400 MHz, METHANOL-d$_4$) δ 7.06 (dt, J = 7.28, 11.17 Hz, 1H), 6.53 (td, J = 7.94, 11.73 Hz, 1H), 4.60 (br s, 2H), 4.54 (br t, J = 8.16 Hz, 1H), 4.03-4.17 (m, 3H), 3.87 (q, J = 7.53 Hz, 1H), 2.67-2.81 (m, 1H), 2.36-2.67 (m, 2H), 1.55-1.75 (m, 1H), 1.26-1.43 (m, 3H), 0.93 (dd, J = 1.63, 6.65 Hz, 6H) | Preparative HPLC separation, Column: Xtimate C18 150 * 25 mm, 5 μm; mobile phase: A: water (0.225% FA), B: methanol, elution gradient: B%: 52%-82%, the retention time thereof was 7.0 min in high performance liquid column chromatography. |

Example 4

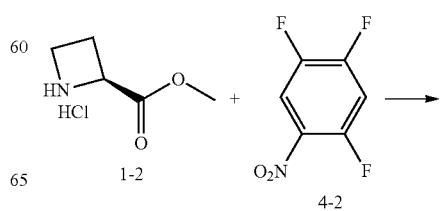

Synthetic Route:

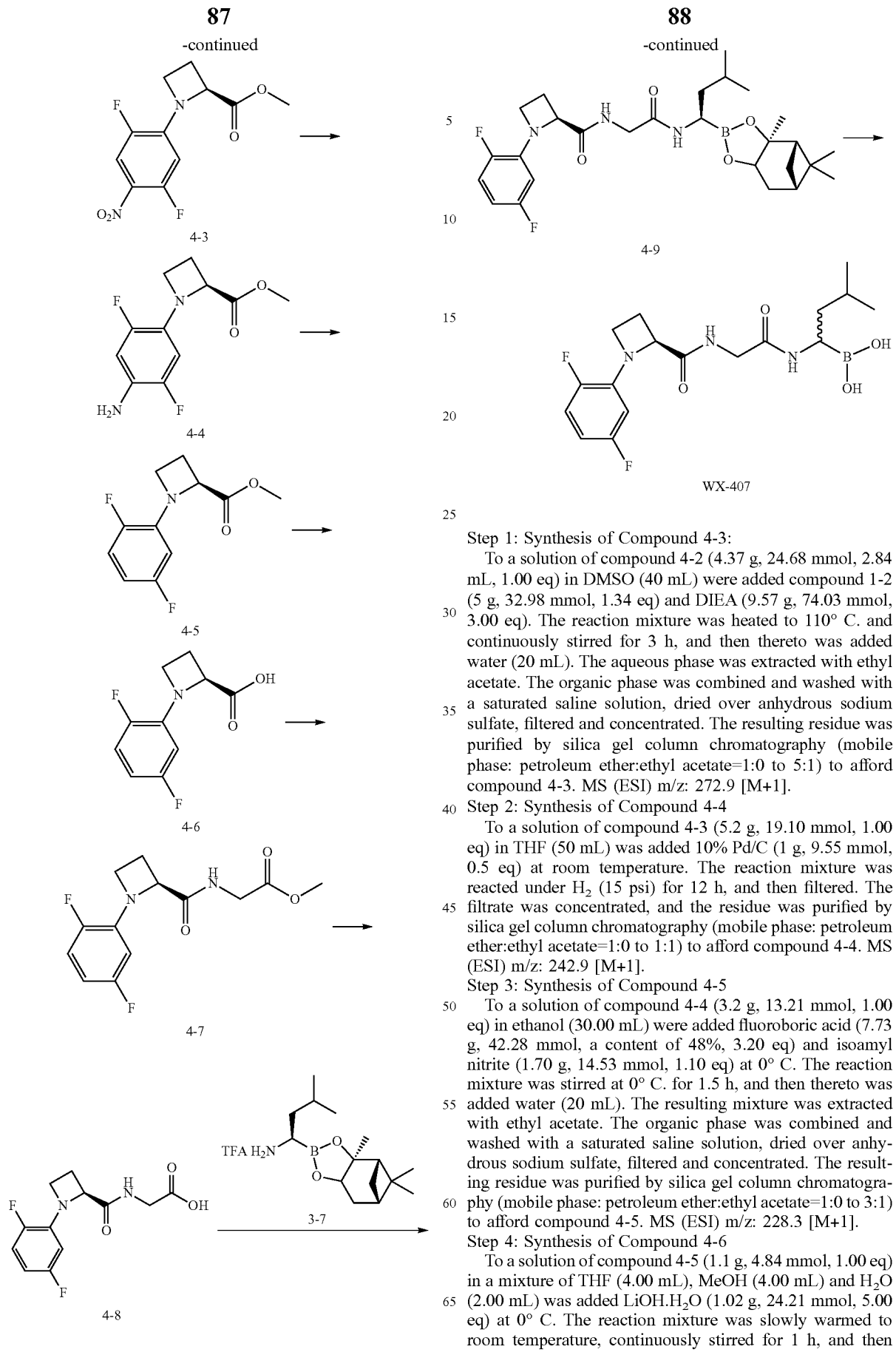

Step 1: Synthesis of Compound 4-3:
To a solution of compound 4-2 (4.37 g, 24.68 mmol, 2.84 mL, 1.00 eq) in DMSO (40 mL) were added compound 1-2 (5 g, 32.98 mmol, 1.34 eq) and DIEA (9.57 g, 74.03 mmol, 3.00 eq). The reaction mixture was heated to 110° C. and continuously stirred for 3 h, and then thereto was added water (20 mL). The aqueous phase was extracted with ethyl acetate. The organic phase was combined and washed with a saturated saline solution, dried over anhydrous sodium sulfate, filtered and concentrated. The resulting residue was purified by silica gel column chromatography (mobile phase: petroleum ether:ethyl acetate=1:0 to 5:1) to afford compound 4-3. MS (ESI) m/z: 272.9 [M+1].

Step 2: Synthesis of Compound 4-4
To a solution of compound 4-3 (5.2 g, 19.10 mmol, 1.00 eq) in THF (50 mL) was added 10% Pd/C (1 g, 9.55 mmol, 0.5 eq) at room temperature. The reaction mixture was reacted under $H_2$ (15 psi) for 12 h, and then filtered. The filtrate was concentrated, and the residue was purified by silica gel column chromatography (mobile phase: petroleum ether:ethyl acetate=1:0 to 1:1) to afford compound 4-4. MS (ESI) m/z: 242.9 [M+1].

Step 3: Synthesis of Compound 4-5
To a solution of compound 4-4 (3.2 g, 13.21 mmol, 1.00 eq) in ethanol (30.00 mL) were added fluoroboric acid (7.73 g, 42.28 mmol, a content of 48%, 3.20 eq) and isoamyl nitrite (1.70 g, 14.53 mmol, 1.10 eq) at 0° C. The reaction mixture was stirred at 0° C. for 1.5 h, and then thereto was added water (20 mL). The resulting mixture was extracted with ethyl acetate. The organic phase was combined and washed with a saturated saline solution, dried over anhydrous sodium sulfate, filtered and concentrated. The resulting residue was purified by silica gel column chromatography (mobile phase: petroleum ether:ethyl acetate=1:0 to 3:1) to afford compound 4-5. MS (ESI) m/z: 228.3 [M+1].

Step 4: Synthesis of Compound 4-6
To a solution of compound 4-5 (1.1 g, 4.84 mmol, 1.00 eq) in a mixture of THF (4.00 mL), MeOH (4.00 mL) and $H_2O$ (2.00 mL) was added LiOH.$H_2O$ (1.02 g, 24.21 mmol, 5.00 eq) at 0° C. The reaction mixture was slowly warmed to room temperature, continuously stirred for 1 h, and then adjusted to about pH=5 with 1N diluted hydrochloric acid. The resulting mixture solution was concentrated, and extracted with ethyl acetate. The organic phase was combined and concentrated to afford a crude product of compound 4-6, which was directly used in a next step. MS (ESI) m/z: 214.0 [M+1].

Step 5: Synthesis of Compound 4-7

To a solution of compound 4-6 (0.68 g, 3.19 mmol, 1.00 eq) in DCM (10.00 mL) were added glycine methyl ester hydrochloride (480.59 mg, 3.83 mmol, 1.20 eq), TBTU (1.23 g, 3.83 mmol, 1.20 eq) and DIEA (1.65 g, 12.76 mmol, 4.00 eq) at −10° C. The reaction mixture was stirred at −10° C. to 0° C. for 0.5 h, and then thereto was added 15 mL water. The resulting mixture was extracted with dichloromethane. The organic phase was combined and washed with a saturated saline solution, dried over anhydrous sodium sulfate, filtered and concentrated. The resulting crude product was purified by silica gel column chromatography (mobile phase: petroleum ether:ethyl acetate=1:0 to 3:1) to afford compound 4-7. MS (ESI) m/z: 284.9 [M+1].

Step 6: Synthesis of Compound 4-8

To a solution of compound 4-7 (0.5 g, 1.76 mmol, 1.00 eq) in a mixture of THF (2.00 mL), MeOH (2.00 mL) and $H_2O$ (1.00 mL) was added $LiOH \cdot H_2O$ (369.03 mg, 8.79 mmol, 5.00 eq) at 0° C. The reaction mixture was slowly warmed to room temperature, continuously stirred for 1 h, and then adjusted to about pH=5 with 1N diluted hydrochloric acid. The resulting mixture solution was concentrated, and extracted with ethyl acetate. The organic phase was combined and concentrated to afford a crude product of compound 4-8, which was directly used in a next step. MS (ESI) m/z: 270.9 [M+1].

Step 7: Synthesis of Compound 4-9

To a solution of compound 4-8 (0.5 g, 1.85 mmol, 1.00 eq) in DMF (8.00 mL) were added compound 3-7 (841.99 mg, 2.22 mmol, 1.20 eq), TBTU (712.90 mg, 2.22 mmol, 1.20 eq) and DIEA (526.08 mg, 4.07 mmol, 2.20 eq) at −10° C. The reaction mixture was stirred at −10° C. to 0° C. for 0.5 h, and then thereto was added 10 mL water. The resulting mixture was extracted with ethyl acetate. The organic phase was combined and washed with a saturated saline solution, dried over anhydrous sodium sulfate, filtered and concentrated. The resulting crude product was purified by silica gel column chromatography to afford compound 4-9. MS (ESI) m/z: 518.2 [M+1].

Step 8: Synthesis of Compound WX-407

To a solution of compound 4-9 (0.42 g, 811.73 μmol, 1.00 eq) in a mixture of MeOH (3.00 mL) and n-hexane (3.00 mL) were added isobutylboronic acid (579.23 mg, 5.68 mmol, 7.00 eq) and HCl (1 M, 1.62 mL, 2.00 eq) at 0° C. The reaction mixture was slowly warmed to room temperature and continuously stirred for 12 h, and then thereto was added 5.00 mL of n-hexane. The resulting mixture solution was extracted with MeOH (10 mL). The methanol layer was adjusted to pH 5-6 with a saturated aqueous solution of sodium bicarbonate and then extracted with ethyl acetate. The organic phase was combined and dried over anhydrous sodium sulfate, filtered and concentrated. The resulting crude product was purified by preparative HPLC to afford compound WX-407. MS (ESI) m/z: 366.1 [M−17].

$^1H$ NMR (400 MHz, METHANOL-$d_4$) δ 6.96 (ddd, J=5.02, 8.91, 12.17 Hz, 1H), 6.40-6.58 (m, 1H), 6.34 (ddd, J=3.14, 7.15, 10.04 Hz, 1H), 4.49-4.70 (m, 2H), 4.12 (s, 3H), 3.78-4.00 (m, 1H), 2.57-2.79 (m, 2H), 2.40-2.53 (m, 1H), 1.57-1.76 (m, 1H), 1.25-1.46 (m, 2H), 0.81-1.01 (m, 6H).

Preparative HPLC Separation Method of WX-407:

Column: Xtimate C18 150*25 mm*5 μm

Mobile phase: A: water (0.225% FA); B: MeOH, elution gradient B %: 59%-89%

The retention time of compound WX-407 was 9.5 min in high performance liquid column chromatography.

Experimental Example 1

In Vitro Anti-Proliferation Test on MM1.S Cells

This test was aimed to investigate the inhibitory effect of a compound on cell proliferation by determining the effect of the compound on cell viability in tumor cell line MM1.S in vitro.

MM1.S cells were seeded into a black 96-well cell culture plate at a density of 7,000 cells per well, and then the plate was incubated overnight in an incubator with 5% $CO_2$ and 100% relative humidity at 37° C. A solution of a test compound in DMSO was added to the cell culture wells at a certain concentration (0.3 to 2000 nM), and then the culture plate was placed back to the incubator, and a vehicle control (containing DMSO with no compound) and a blank control were provided.

The culture plate was incubated in the incubator with 5% $CO_2$ and 100% relative humidity at 37° C. for 2 days. The sample was treated using the Promega CellTiter-Glo Luminescent Cell Viability Assay Kit (Promega-G7571) standard method, and a luminescent signal was detected on the SpectraMax i3x of Molecular Devices plate reader. The inhibition rate of the test compound was calculated through the following equation using original data:

$$\text{inhbition rate \%} = \frac{RLU \text{ of vehicle control} - RLU \text{ of compound}}{RLU \text{ of vehicle control} - RLU \text{ of blank control}} \times 100\%$$

RLU represents a relative luminescence intensity.

The in vitro anti-proliferation test result of the test compound against MM1.S cells was shown in Table 1.

TABLE 1

| Compound | $IC_{50}$ (μM) |
| --- | --- |
| WX-174 | 0.0058 |
| WX-193 | 0.0082 |
| WX-333 | 0.0010 |
| WX-260 | 0.0110 |
| WX-301 | 0.0058 |
| WX-306 | 0.0082 |
| WX-308 | 0.0089 |
| WX-313 | 0.0245 |
| WX-317 | 0.0320 |
| WX-327 | 0.0242 |
| WX-329 | 0.0115 |
| WX-351 | 0.0459 |
| WX-355 | 0.0288 |
| WX-365 | 0.0906 |
| WX-367 | 0.1831 |
| WX-373 | 0.0267 |
| WX-379 | 0.0240 |
| WX-381 | 0.1194 |
| WX-385 | 0.1045 |
| WX-391 | 0.0054 |

Experimental Example 2

Liver Microsome Stability Test of Compounds

A test compound was incubated with CD-1 mouse liver microsome, SD rat liver microsome, and human liver microsome, respectively, to evaluate the stability of the test compound.

Preparation of a solution sample of the test compound: 10 mM solution (5 µL) of a compound prepared in the Example in DMSO was added to a mixed solvent (450 µL) of DMSO (45 µL), methanol and water (a volume ratio of methanol to water was 1:1) to prepare a 100 µM solution of the test compound; and 50 µL of the 100 µM solution of the test compound was added to 450 µL of 100 mM potassium phosphate buffer to obtain a 10 µM solution of the test compound.

The 10 µM solution of the test compound was pre-incubated with the microsome from the above three species for 10 minutes, respectively, and then a working solution of a reduced nicotinamide adenine dinucleotide phosphate (NADPH) regeneration system was added to the incubation plate at each time point to initiate the reaction, and finally a stop solution (100% ACN) was added to the reaction plate to terminate the reaction at 0, 5, 10, 20, 30 and 60-minute. The test compound was determined by LC-MS/MS method. The liver microsome stability test result of the test compound was shown in Table 2.

TABLE 2

| Compound | Liver microsome stability ($T_{1/2}$, min) |
| --- | --- |
| WX-174 | 3.5(H), 1.6(R), 0.8(M) |
| WX-193 | 4.8(H), 4.6(R), 2.7(M) |
| WX-333 | 67.4(H), 43.1(R), 67.4(M) |
| WX-260 | 107.9(H), >145(R), 84.8(M) |
| WX-301 | 74.3(H), 42.1(R), 43.5(M) |
| WX-306 | 17.8(H), 37.4(R), 14.0(M) |
| WX-308 | 27.4(H), 26.8(R), 20.1(M) |
| WX-313 | >145(H), 57.2(R), 52.5(M) |
| WX-317 | 77.0(H), 35.5(R), 27.1(M) |
| WX-327 | 75.0(H), 26.5(R), 37.7(M) |
| WX-329 | 51.5(H), 43.3(R), 40.3(M) |

Note:
H represents human, R represents rat, and M represents mouse.

Experimental Example 3

Cell Membrane Permeability Test of Compounds

Cell membrane permeability of a test compound was evaluated on MDR1-MDCK II cells.

A test compound (10 mM solution of the compound in DMSO) was diluted with a transfer buffer (HBSS with 10 mM Hepes, pH=7.4) to prepare a sample having a final concentration of 2 µM, followed by bidirectional (A-B and B-A) administration. After administration, the cell plate was incubated in an incubator with 5% $CO_2$ and a saturated humidity at 37° C. for 150 minutes. After the 150-minute incubation, the sample was collected, and the concentration of the test compound in the transfer sample was semi-quantitatively determined by LC/MS/MS method. The cell membrane permeability test result of the test compound was shown in Table 3.

TABLE 3

| Compound | Papp A to B (10e−6 cm/s) | Papp B to A (10e−6 cm/s) | Efflux Ratio |
| --- | --- | --- | --- |
| WX-174 | 0.44 | 18.39 | 41.79 |
| WX-193 | 0.10 | 13.06 | 130.60 |
| WX-333 | 0.38 | 7.32 | 19.26 |
| WX-260 | 0.30 | 5.10 | 17.00 |
| WX-306 | 0.30 | 17.80 | 59.33 |
| WX-308 | 0.20 | 15.30 | 76.50 |
| WX-313 | 0.20 | 1.29 | 7.16 |
| WX-317 | 0.01 | 0.05 | 5.00 |
| WX-327 | 0.24 | 2.24 | 9.33 |
| WX-329 | 0.27 | 3.74 | 13.85 |

Note:
"Papp A to B" represented the rate at which the compound entered the cell;
"Papp B to A" represented the rate at which the cell excluded the compound;
Efflux Ratio = Papp B to A/Papp A to B

What is claimed is:

1. A compound of Formula (I), a pharmaceutically acceptable salt, a tautomer, a stereoisomer or a geometric isomer thereof,

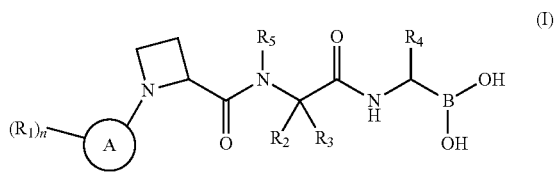

wherein,
ring A is selected from the group consisting of $C_{3-6}$ cycloalkyl, phenyl and 5 to 10-membered heteroaryl;
n is selected from 0, 1, 2 or 3;
$R_1$ is each independently selected from the group consisting of halo, OH, $NH_2$, CN, $C_{1-3}$ alkyl, $C_{1-3}$ heteroalkyl and phenyl, wherein the $C_{1-3}$ alkyl, $C_{1-3}$ heteroalkyl or phenyl is each optionally substituted with 1, 2 or 3 Rs;
$R_2$ and $R_3$ are each independently selected from the group consisting of H, halo, OH, $NH_2$, CN, $C_{1-6}$ alkyl, $C_{1-6}$ heteroalkyl, $C_{3-6}$ cycloalkyl, $C_{3-6}$ cycloalkyl-$(CH_2)_{1-3}$— and phenyl-$(CH_2)_{1-3}$—, wherein the $C_{1-6}$ alkyl, $C_{1-6}$ heteroalkyl, $C_{3-6}$ cycloalkyl, $C_{3-6}$ cycloalkyl-$(CH_2)_{1-3}$— or phenyl-$(CH_2)_{1-3}$— is each optionally substituted with 1, 2 or 3 Rs; or
$R_2$ and $R_3$ together with the carbon atom to which they are attached form a 3 to 6-membered ring;
$R_4$ is selected from the group consisting of $C_{1-6}$ alkyl and $C_{3-6}$ cycloalkyl-$(CH_2)_{1-3}$—, wherein the $C_{1-6}$ alkyl or $C_{3-6}$ cycloalkyl-$(CH_2)_{1-3}$— is each optionally substituted with 1, 2 or 3 Rs;
$R_5$ is selected from the group consisting of H and $C_{1-3}$ alkyl optionally substituted with 1, 2 or 3 Rs;
each R is independently selected from the group consisting of F, Cl, Br, I, OH, Me, $NH_2$, $NH(CH_3)$ and $N(CH_3)_2$;
wherein the prefix "hetero" in the $C_{1-3}$ heteroalkyl, $C_{1-6}$ heteroalkyl and 5 to 10-membered heteroaryl is each independently selected from the group consisting of —O—, —S—, —NH— and N; and in any one of the above cases, the number of heteroatom or group containing the heteroatom is independently selected from 1, 2 or 3.

2. The compound according to claim 1, wherein n is selected from 0, 1 or 2.

3. The compound according to claim 1, wherein $R_1$ is each independently selected from the group consisting of halo, OH, $NH_2$, CN, $C_{1-3}$ alkyl, $C_{1-3}$ alkoxy and phenyl, wherein the $C_{1-3}$ alkyl, $C_{1-3}$ alkoxyl or phenyl is each optionally substituted with 1, 2 or 3 Rs.

4. The compound according to claim 1, wherein $R_1$ is each independently selected from the group consisting of F, Cl, Br, I, OH, $NH_2$, CN, Me, $CF_3$,

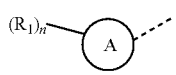

5. The compound according to claim 1, wherein ring A is selected from the group consisting of cyclopropyl, phenyl, pyridyl, pyrimidinyl, pyrazinyl, pyridazinyl, 1,3,4-oxadiazolyl, thiazolyl, isothiazolyl, thienyl, pyrazolyl, imidazolyl and 1H-indazolyl.

6. The compound according to claim 1, wherein a structural unit

in the compound of Formula (I) is selected from the group consisting of

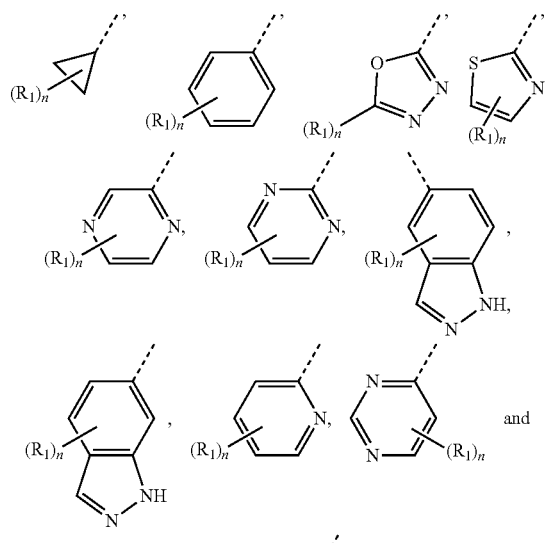

7. The compound according to claim 1, wherein a structural unit

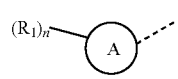

in the compound of Formula (I) is selected from the group consisting of

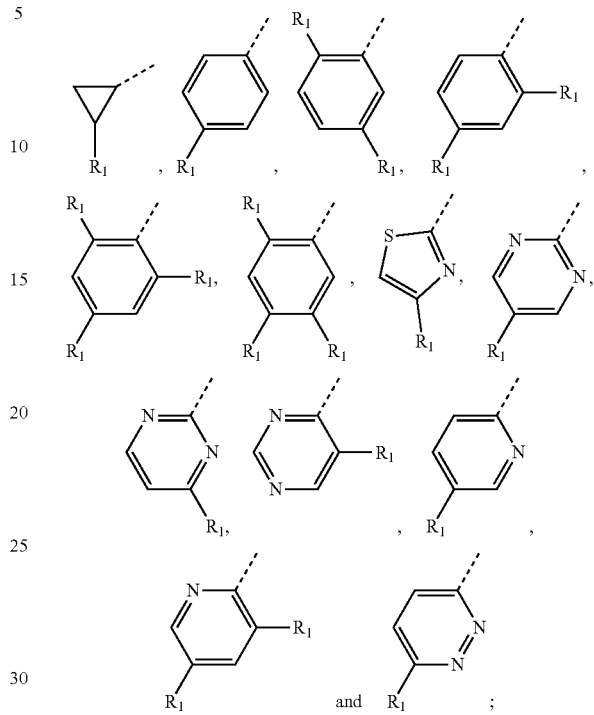

8. The compound according to claim 1, wherein a structural unit

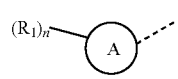

in the compound of Formula (I) is selected from the group consisting of

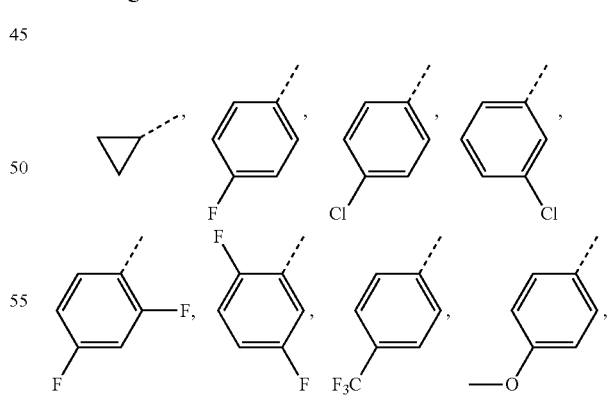

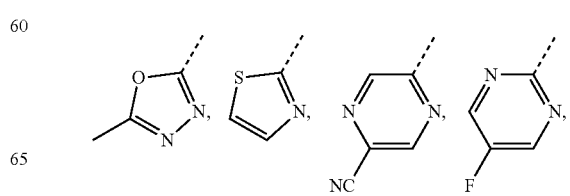

-continued

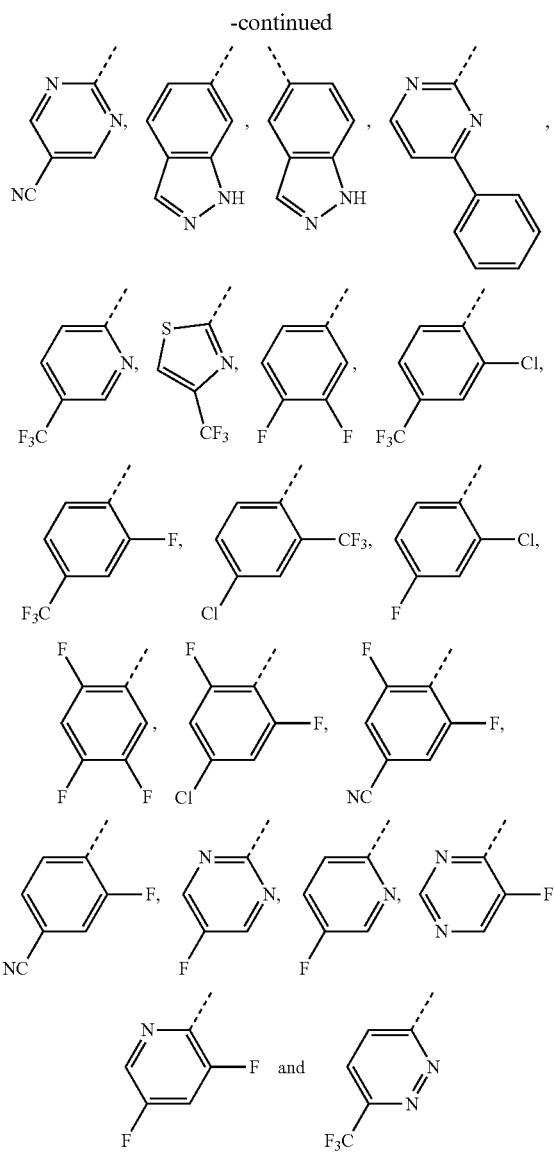

9. The compound according to claim 1, wherein $R_2$ and $R_3$ are each independently selected from the group consisting of H, halo, OH, $NH_2$, CN, $C_{1-6}$ alkyl, $C_{1-3}$ alkoxy, $C_{1-3}$ alkyl-O—$C_{1-3}$ alkyl, $C_{3-6}$ cycloalkyl-$CH_2$— and phenyl-$CH_2$—, wherein the $C_{1-6}$ alkyl, $C_{1-3}$ alkoxy, $C_{1-3}$ alkyl-O—$C_{1-3}$ alkyl, $C_{3-6}$ cycloalkyl-$CH_2$— or phenyl-$CH_2$— is each optionally substituted with 1, 2 or 3 Rs; or $R_2$ and $R_3$ together with the carbon atom to which they are attached form a 3 to 6-membered cycloalkyl.

10. The compound according to claim 1, wherein $R_3$ is H, and $R_2$ is selected from the group consisting of H, Me,

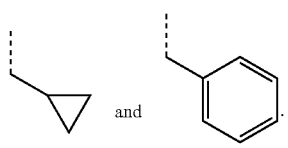

11. The compound according to claim 1, wherein $R_4$ is selected from the group consisting of

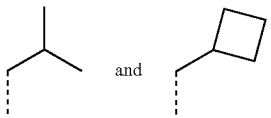

12. The compound according to claim 1, wherein $R_5$ is selected from the group consisting of H, Me and Et.

13. The compound according to claim 1, wherein each R is independently selected from the group consisting of F, Cl, Br, I, OH, Me and $NH_2$.

14. The compound according to claim 1, wherein the compound of Formula (I) is selected from the group consisting of a compound of Formula (II), a compound of Formula (III), a compound of Formula (IV), a compound of Formula (V), a compound of Formula (VI), a compound of Formula (I-a), a compound of Formula (I-b), a compound of Formula (II-a), a compound of Formula (II-b), a compound of Formula (III-a), a compound of Formula (III-b), a compound of Formula (IV-a), a compound of Formula (IV-b), a compound of Formula (V-a), a compound of Formula (V-b), a compound of Formula (VI-a) and a compound of Formula (VI-b),

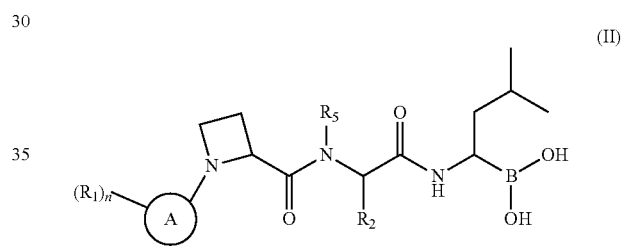
(II)

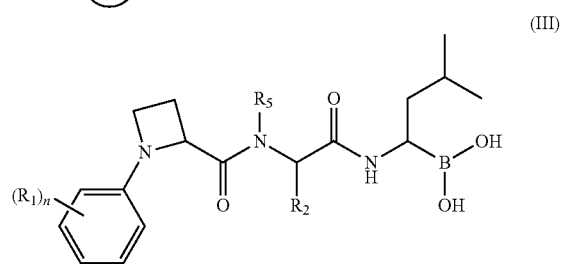
(III)

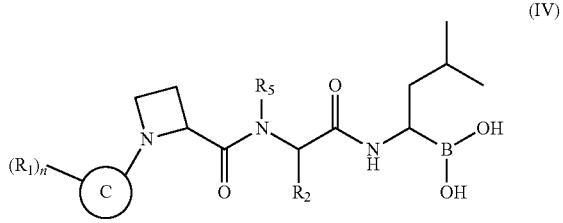
(IV)

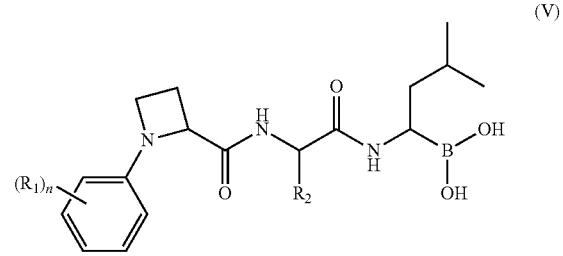
(V)

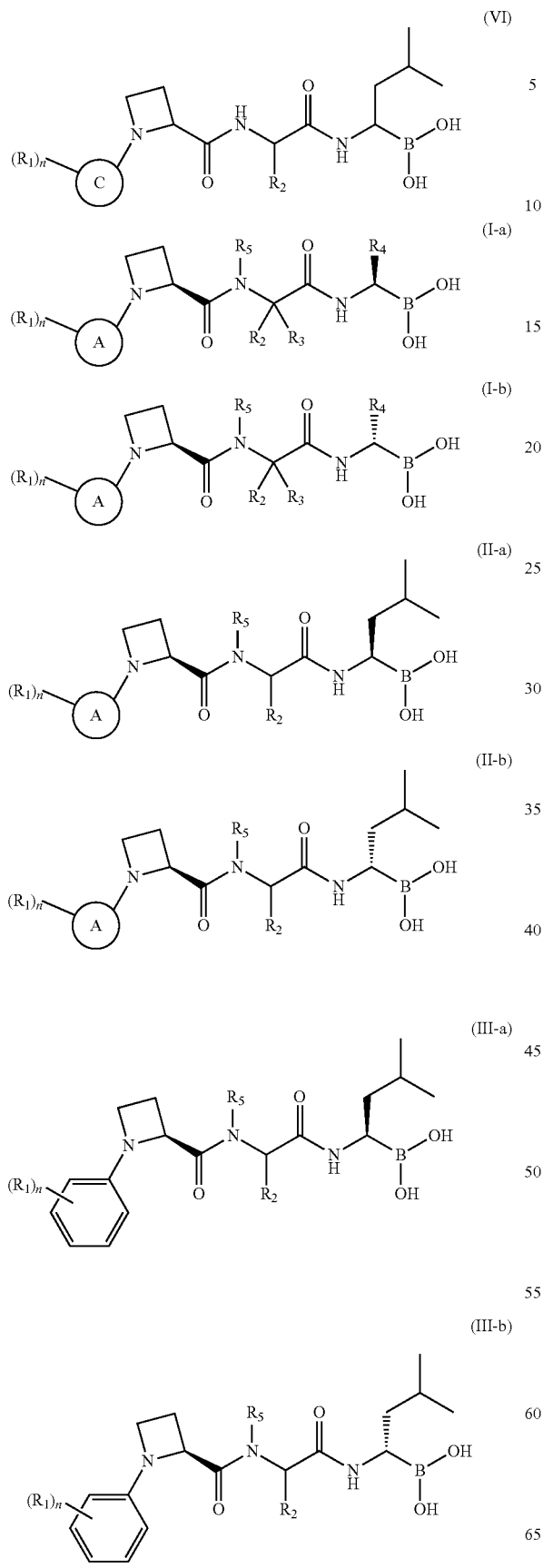
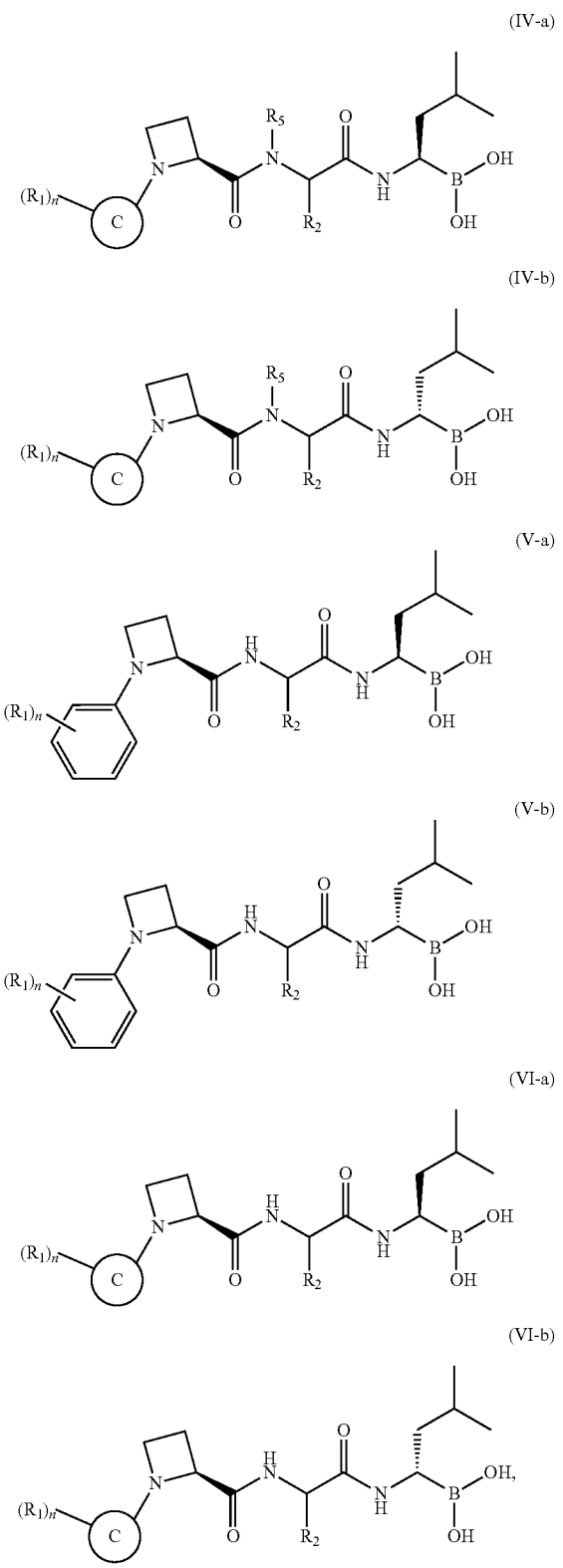
wherein, ring C is selected from the group consisting or cyclopropyl, 5-membered heteroaryl and 6-membered heteroaryl.

15. The compound according to claim 14, wherein the structural unit
in the Formula (IV-a), Formula (IV-b), Formula (VI-a) or Formula (VI-b) is selected from the group consisting of
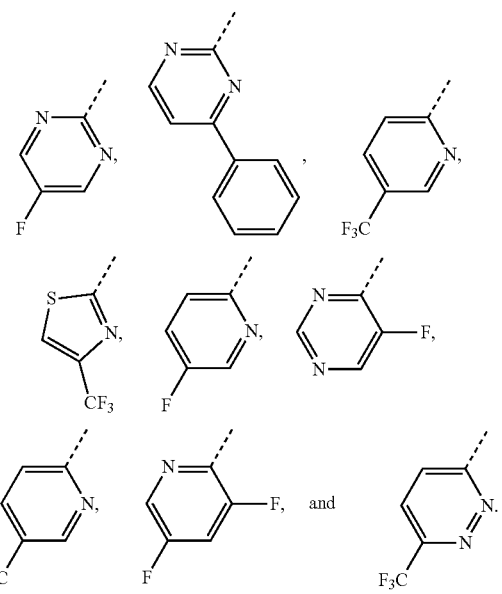
16. The compound according to claim 1, wherein the compound of Formula (I) is selected from the group consisting of
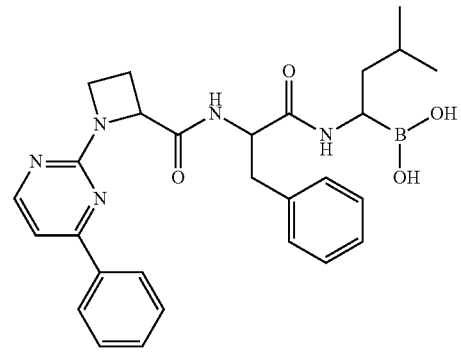
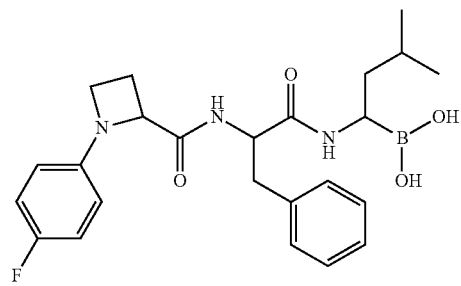
-continued
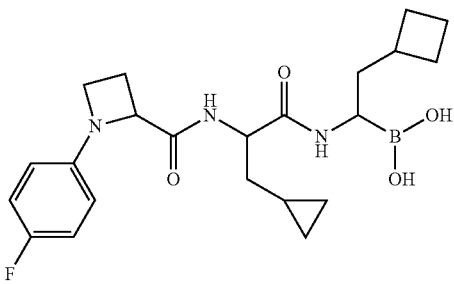
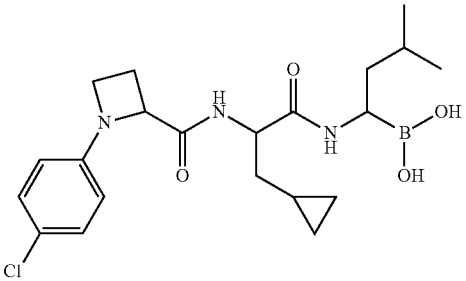
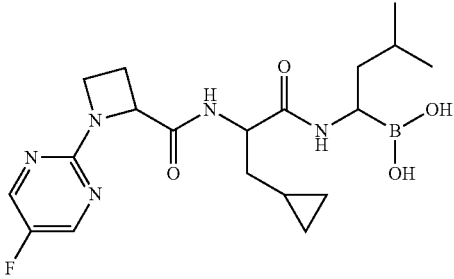
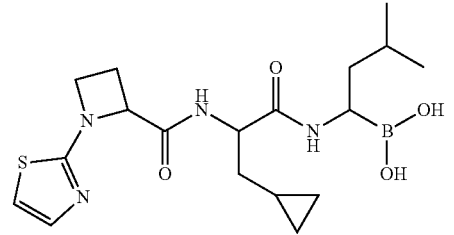
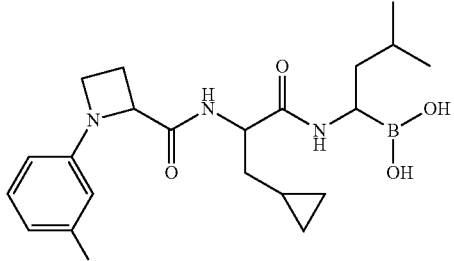
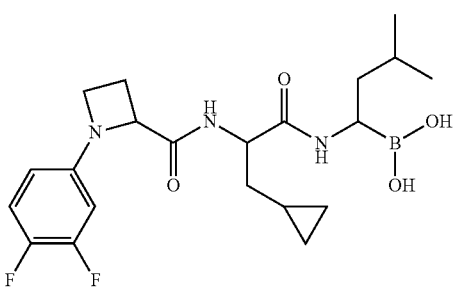

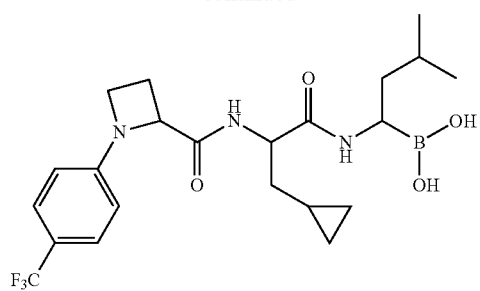
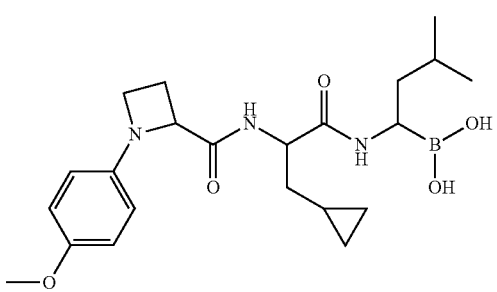
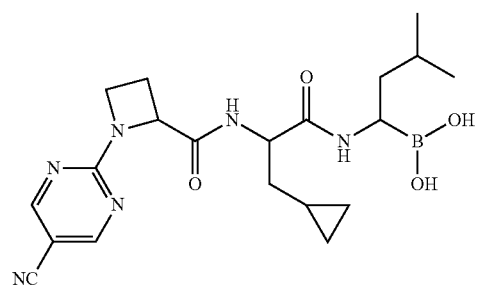
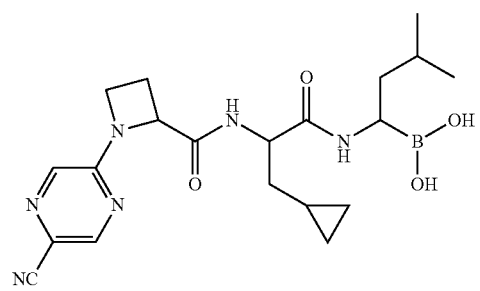
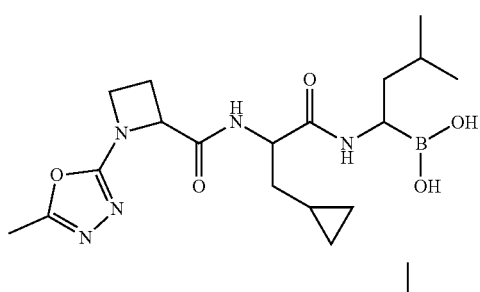
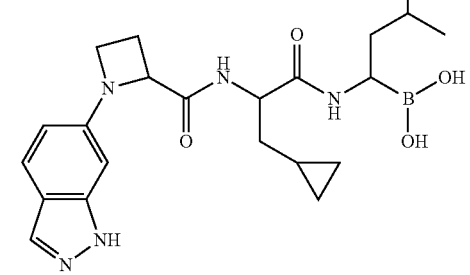
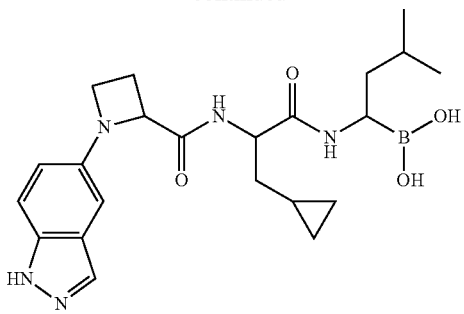
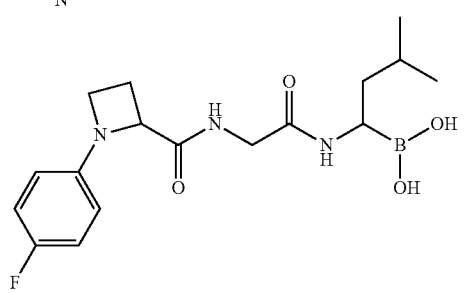
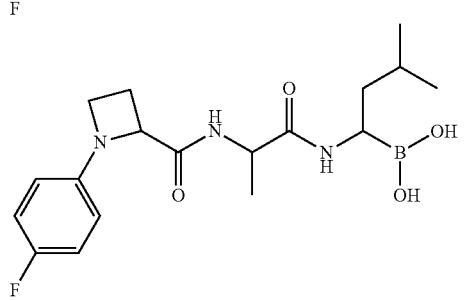
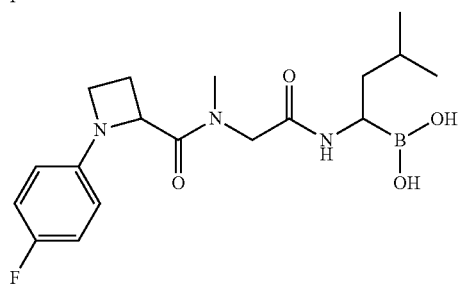
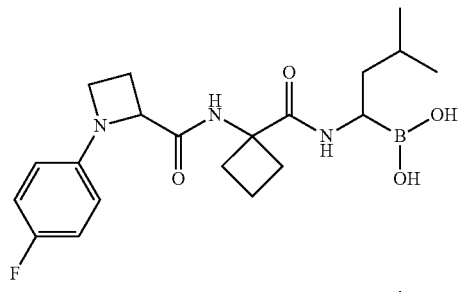
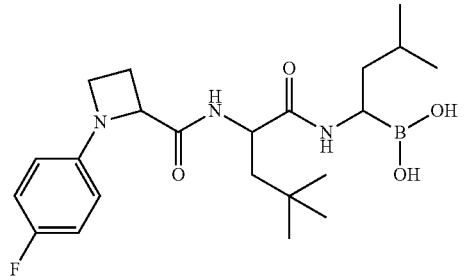

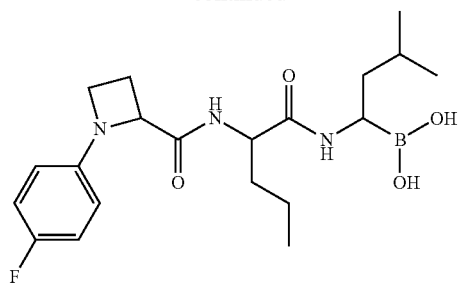
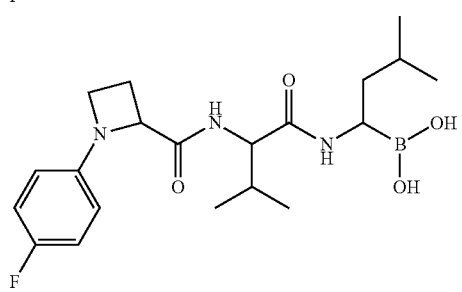
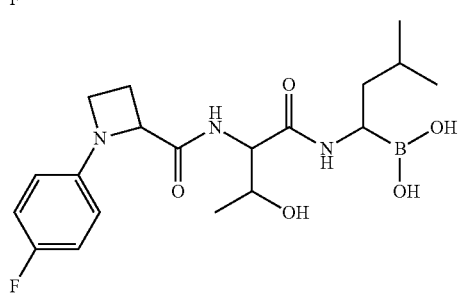
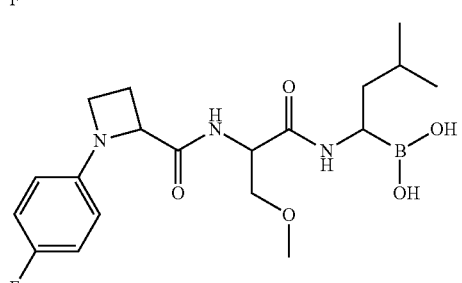
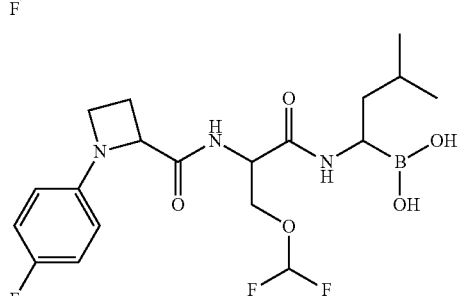
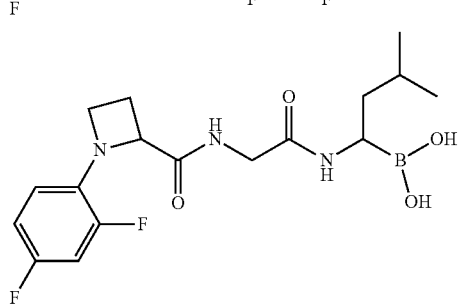
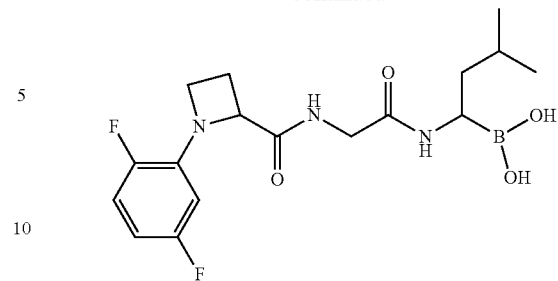
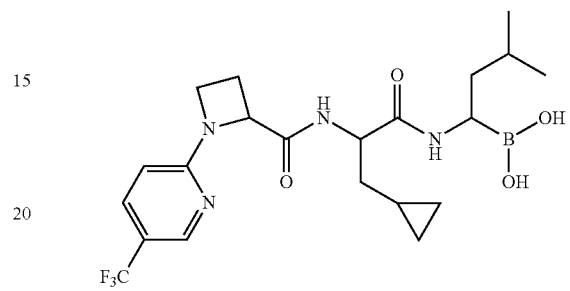
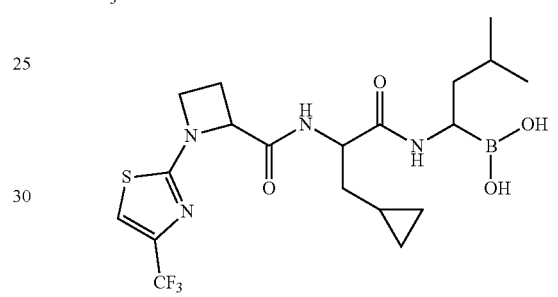
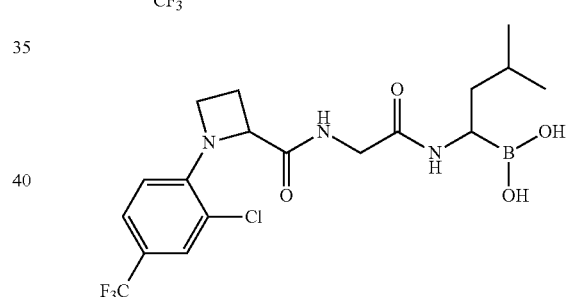
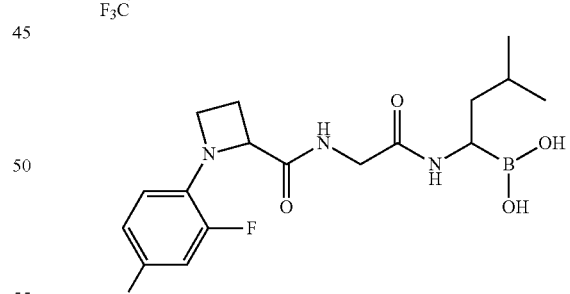
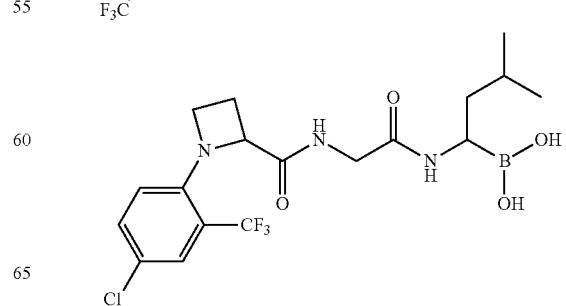

105
-continued
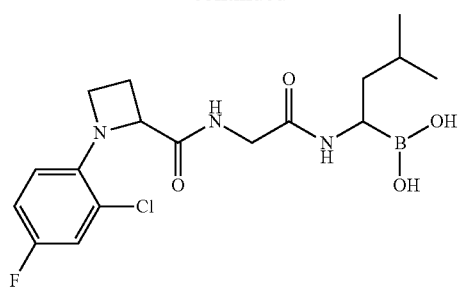
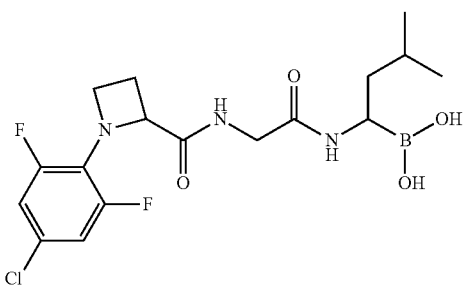
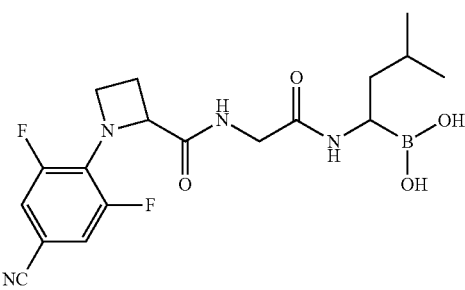
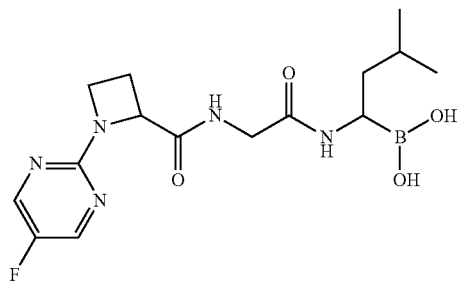
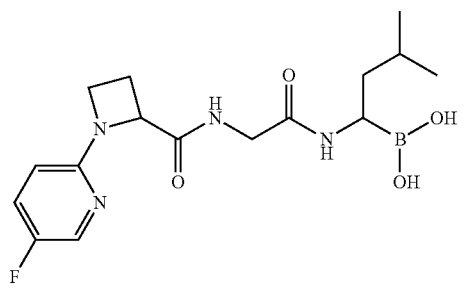
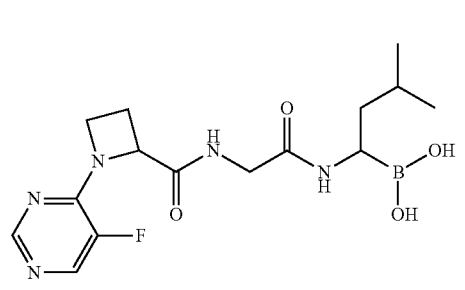
106
-continued
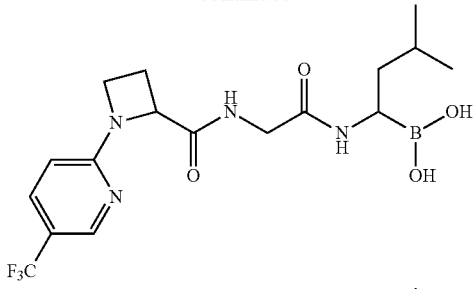
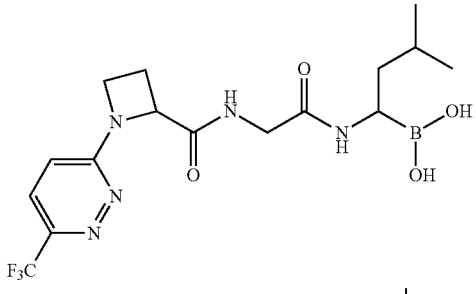
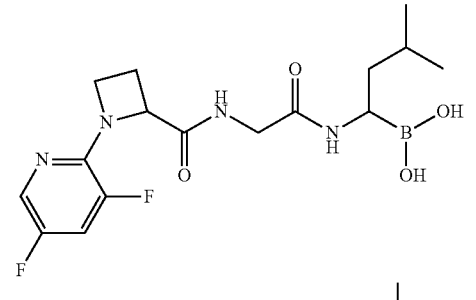
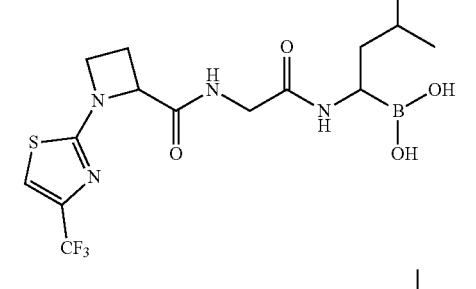
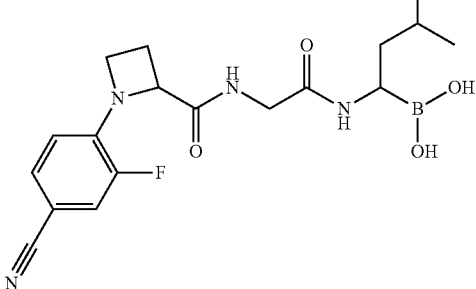
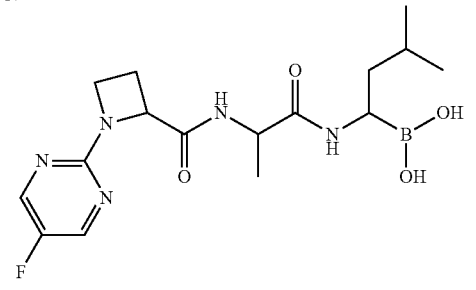

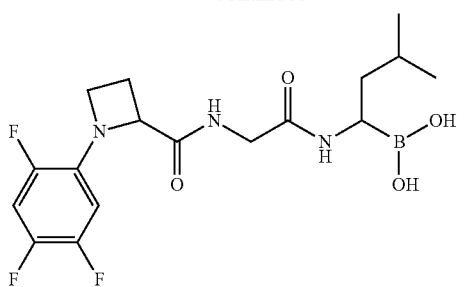
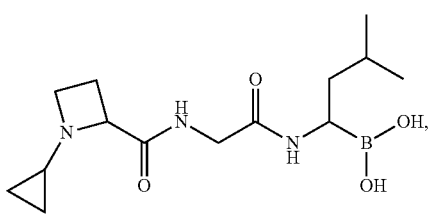
or a pharmaceutically acceptable salt, a tautomer, stereoisomer or a geometric isomer thereof.
17. The compound according to claim 1, wherein the compound of Formula (I) is selected from the group consisting of
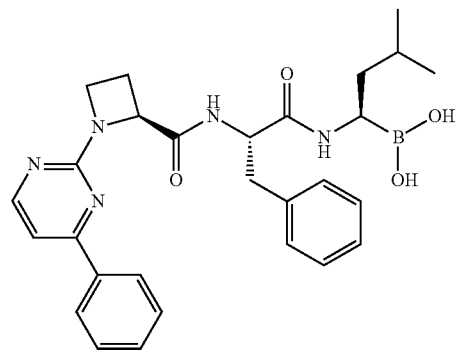
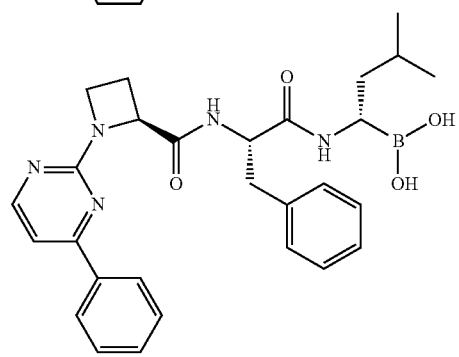
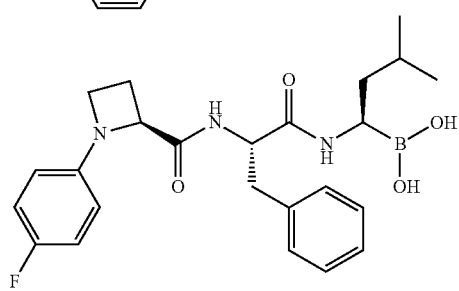
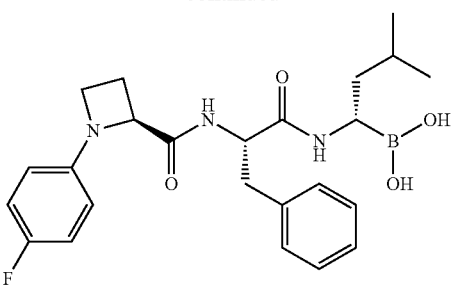
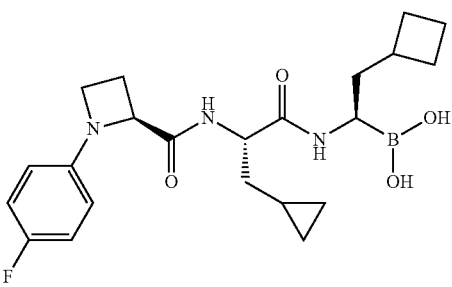
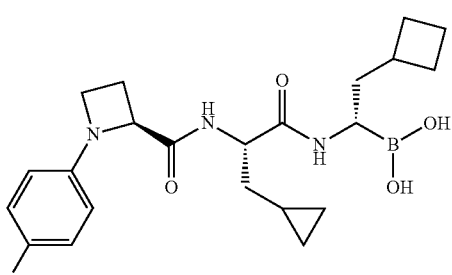
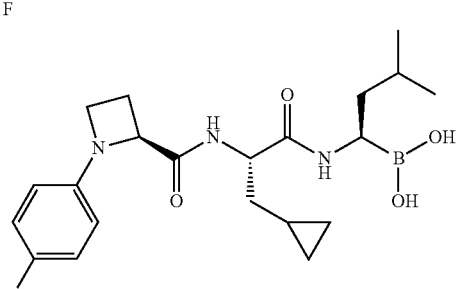
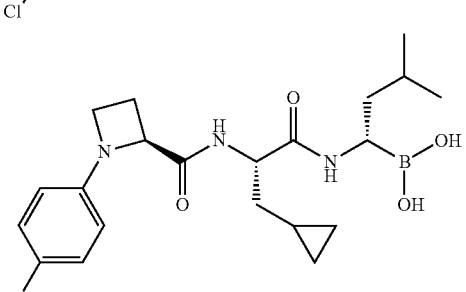
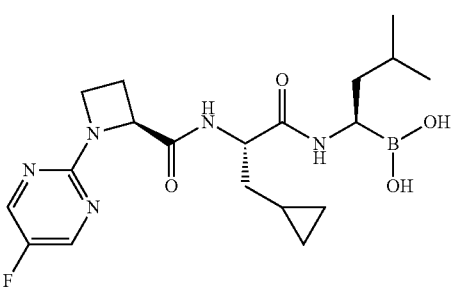

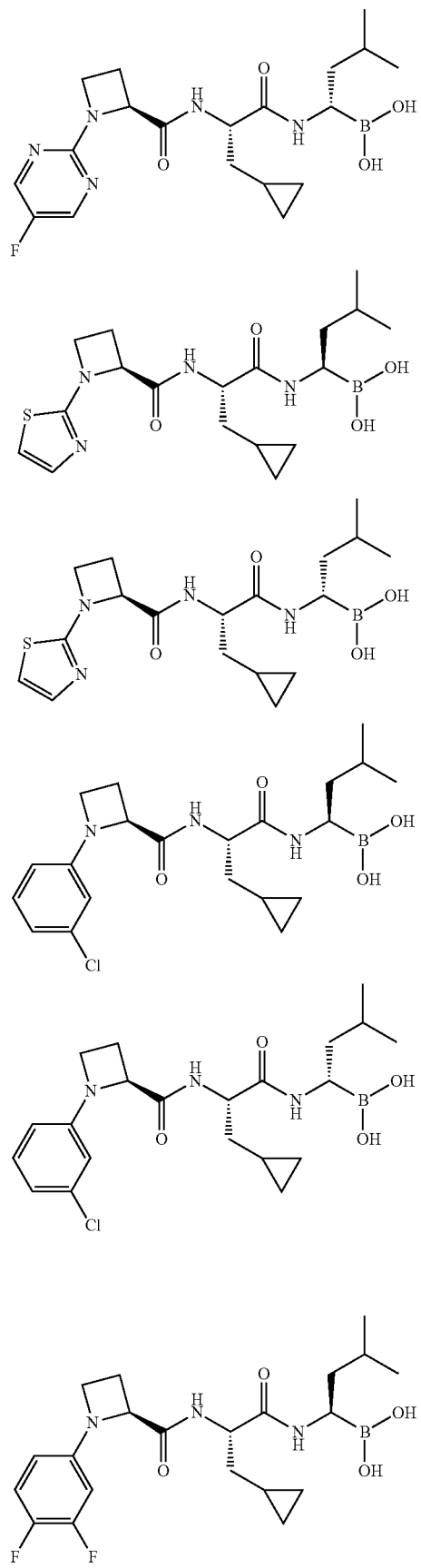
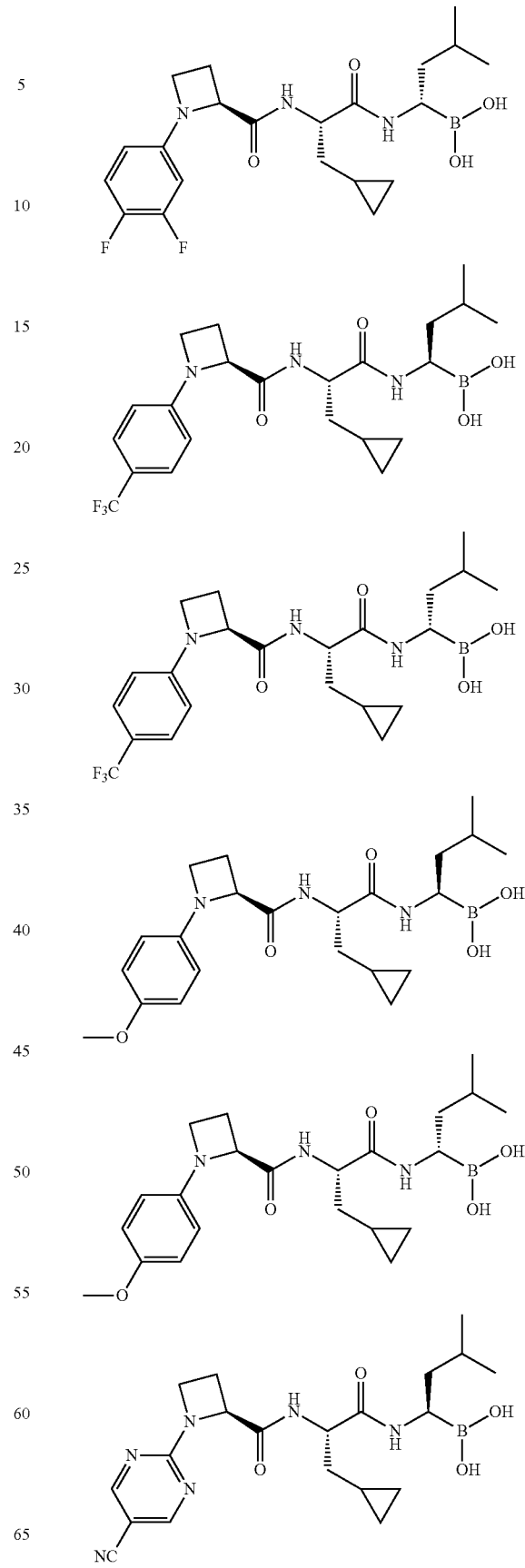

111
-continued
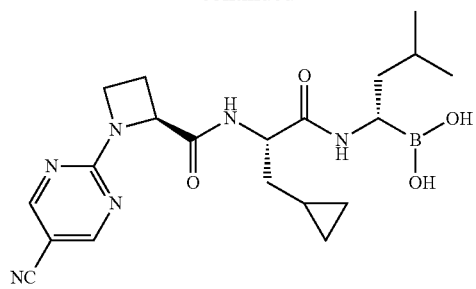
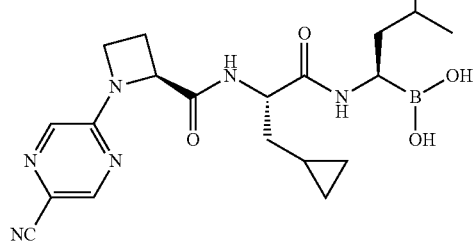
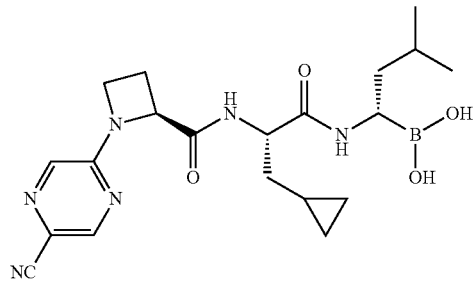
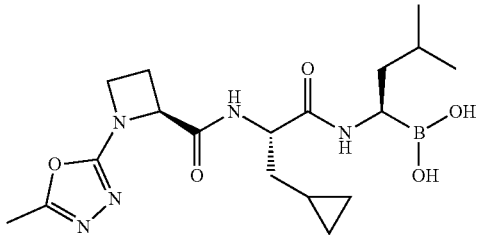
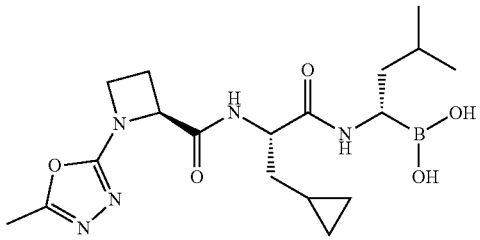
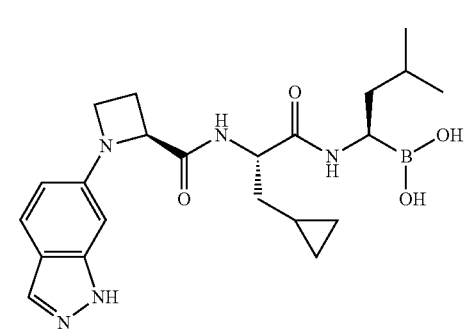
112
-continued
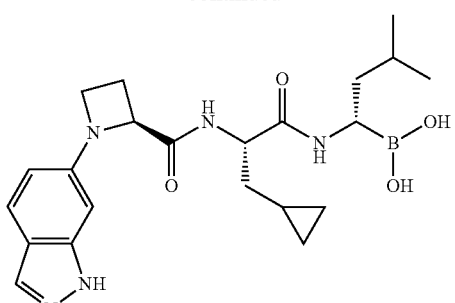
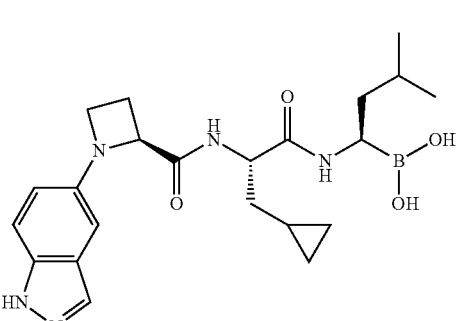
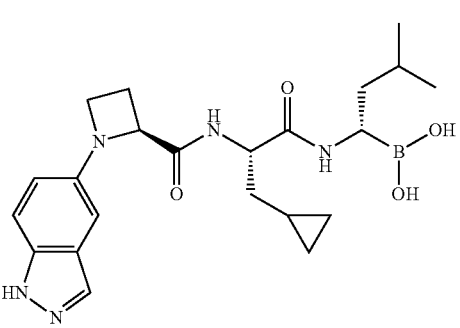
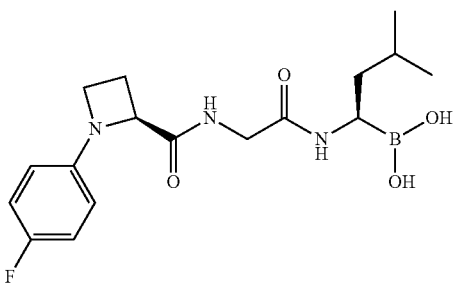
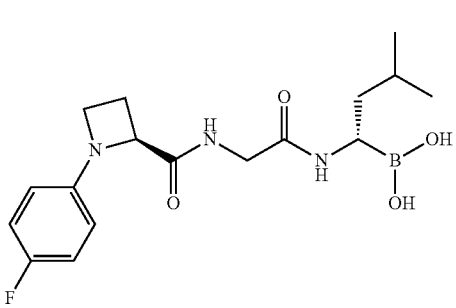

113
-continued
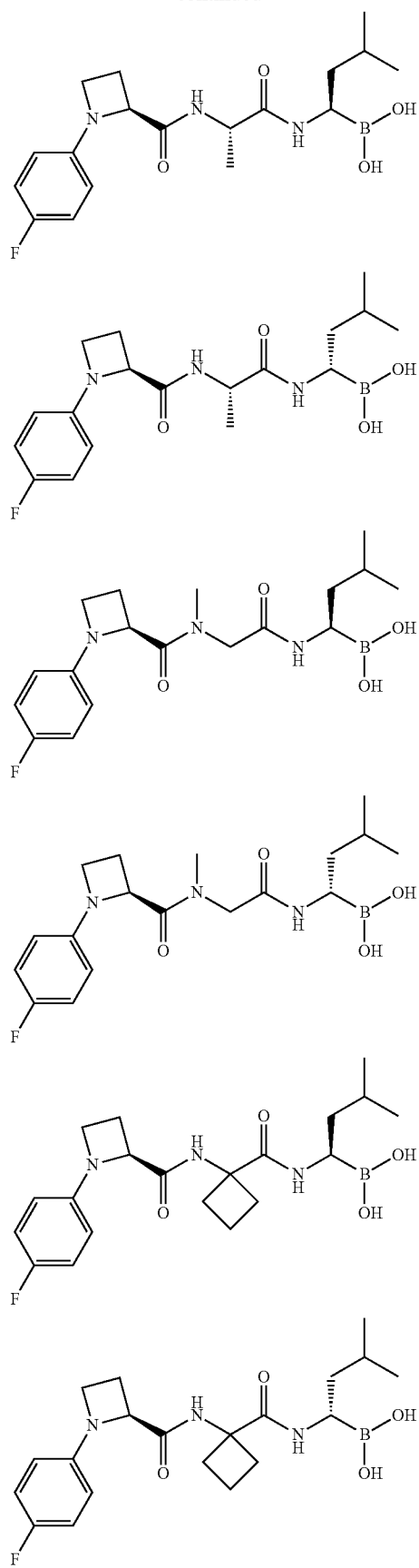
114
-continued
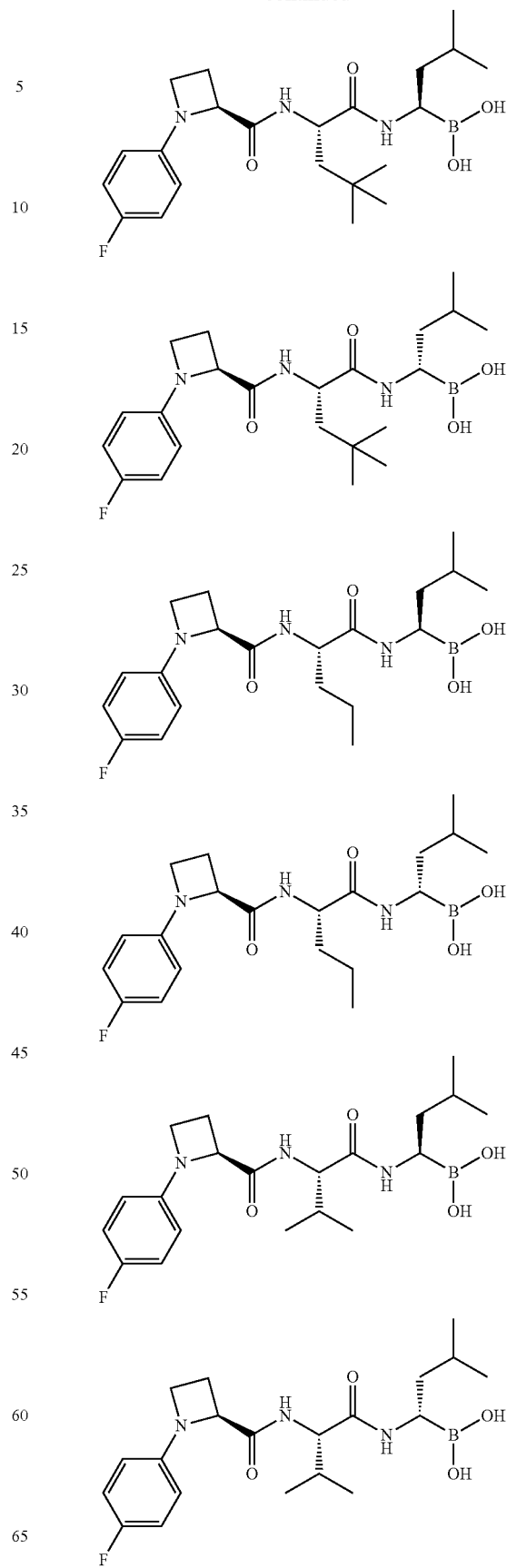

115
-continued
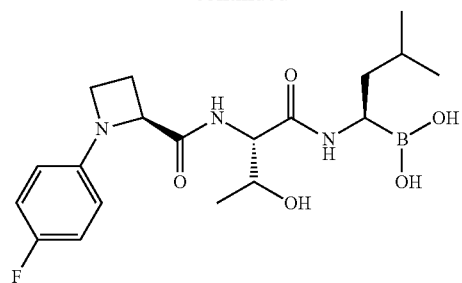
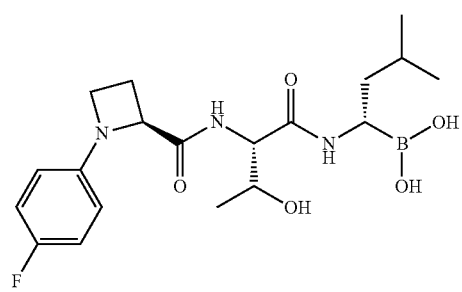
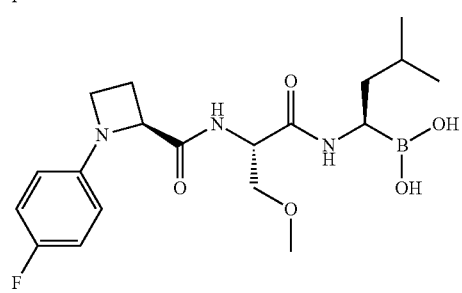
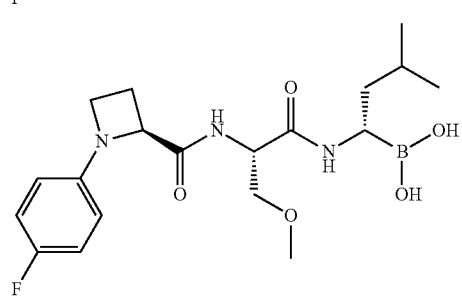
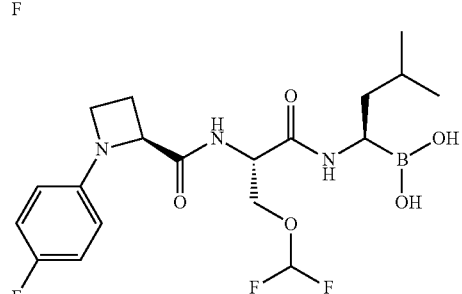
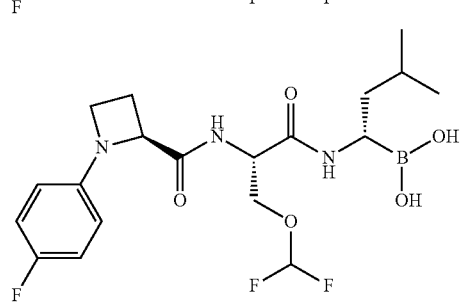
116
-continued
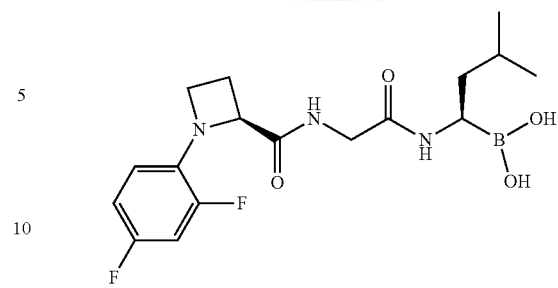
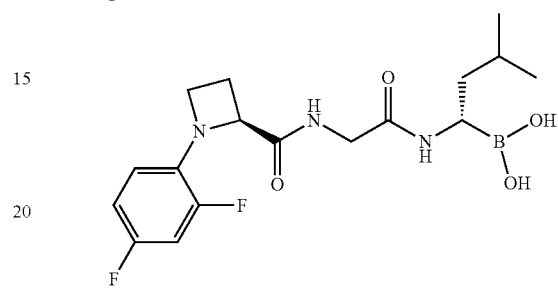
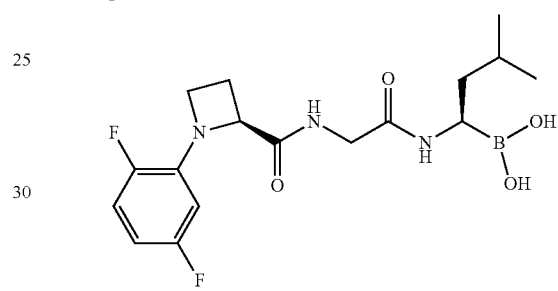
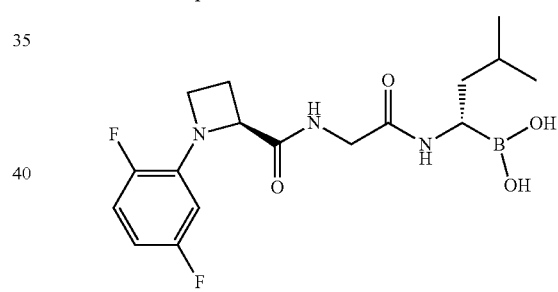
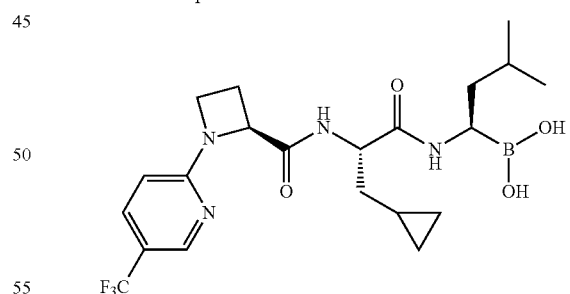
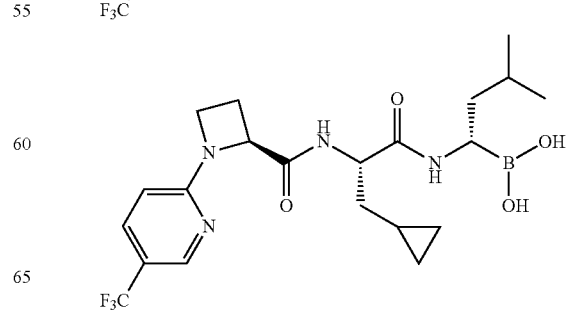

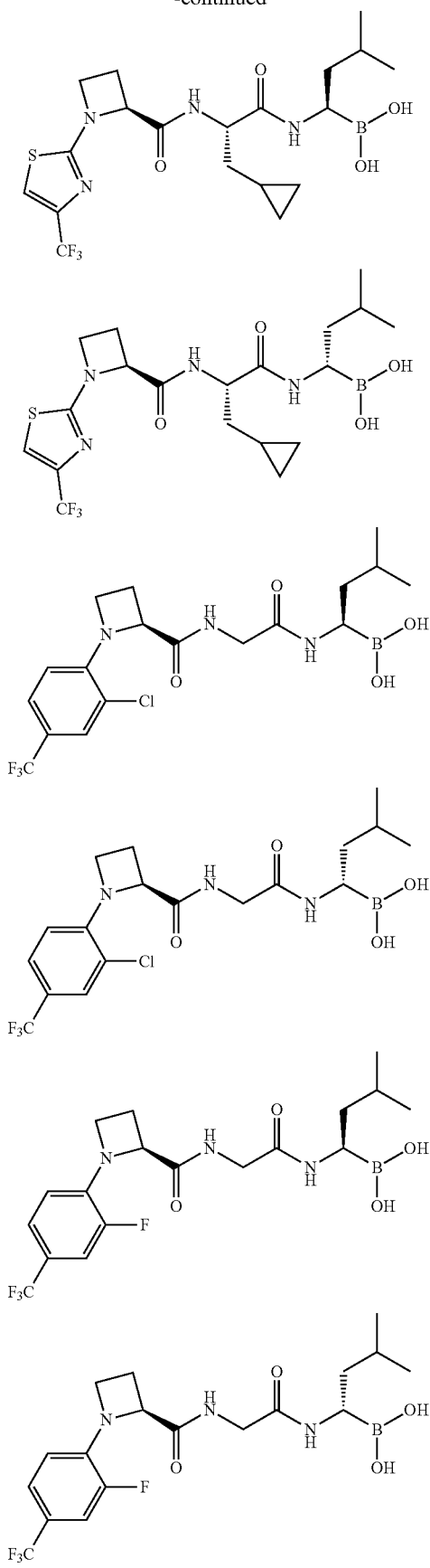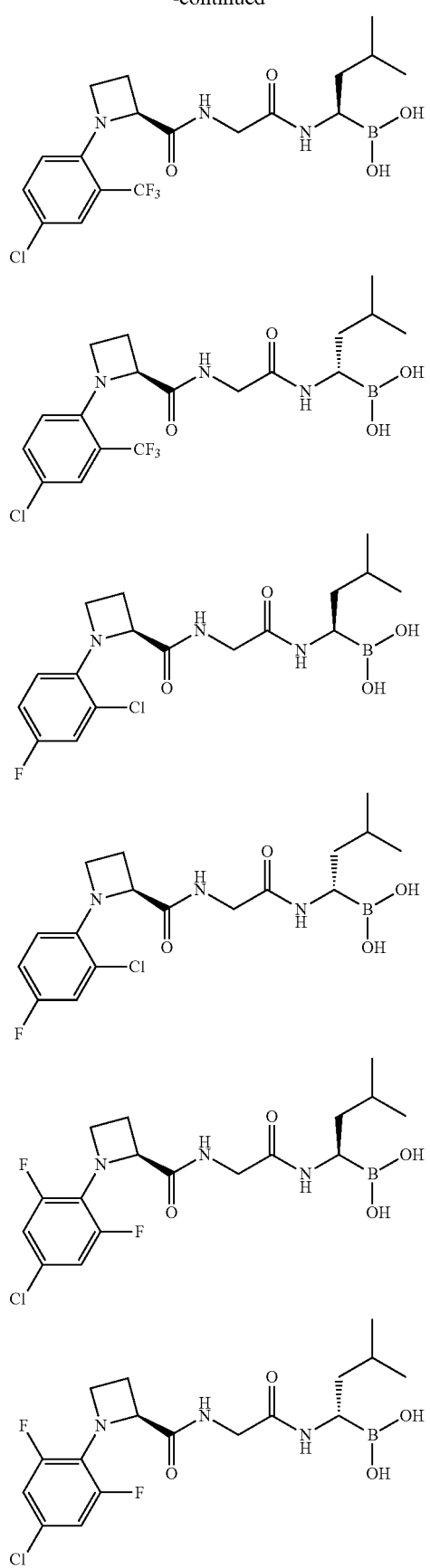

119
-continued
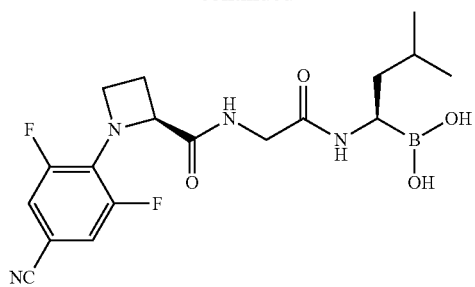
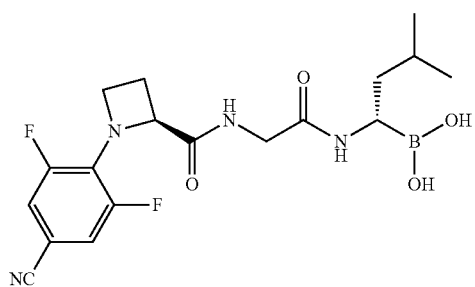
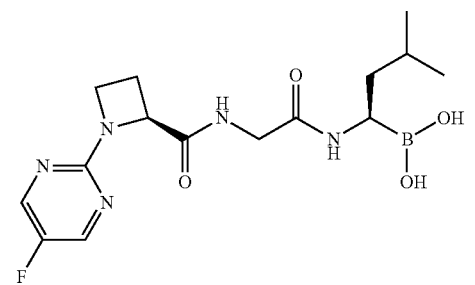
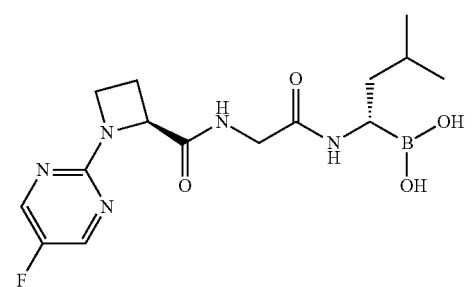
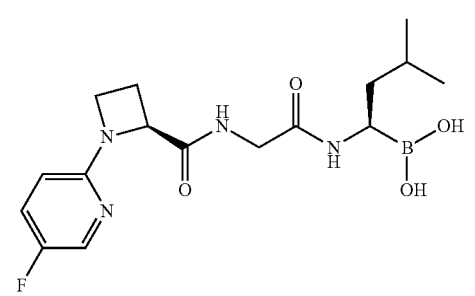
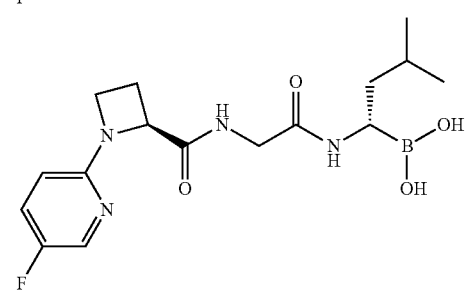
120
-continued
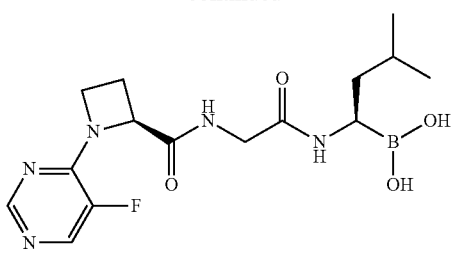
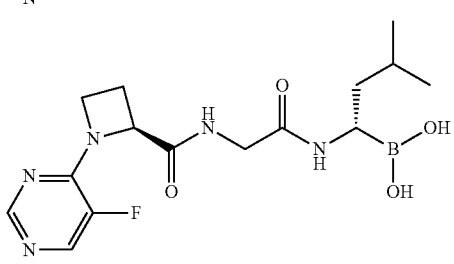
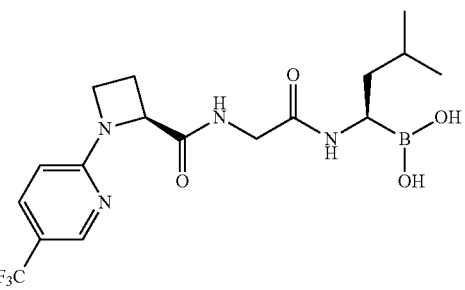
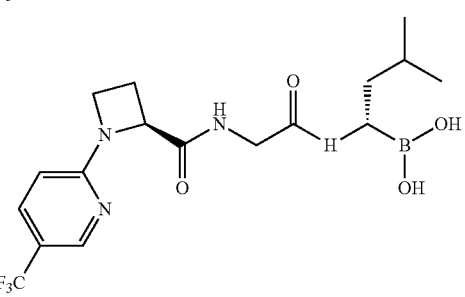
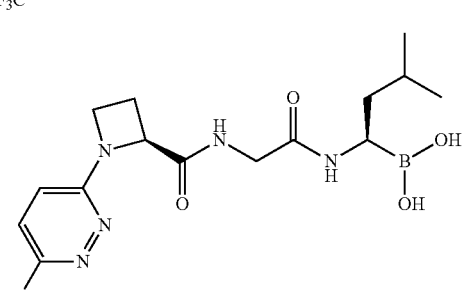
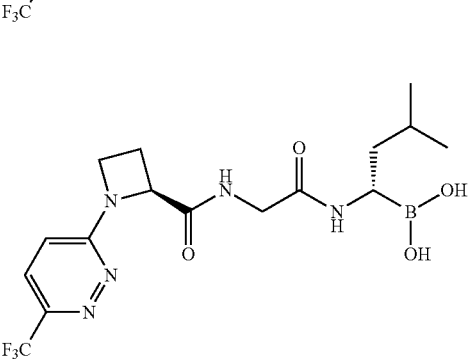

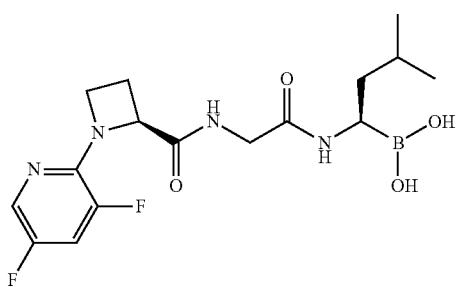
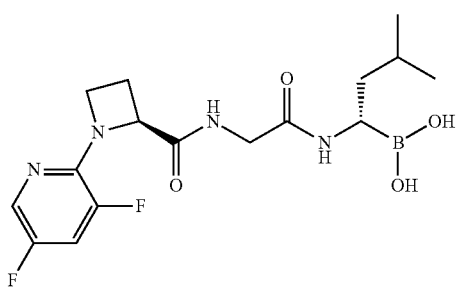
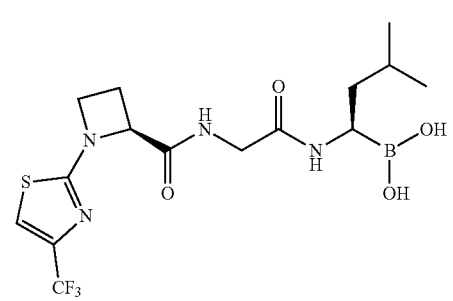
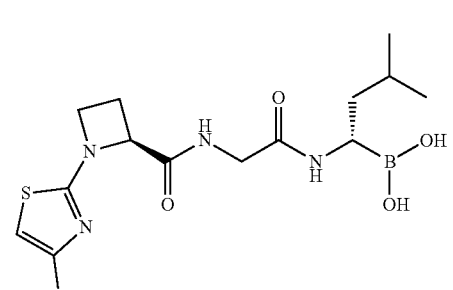
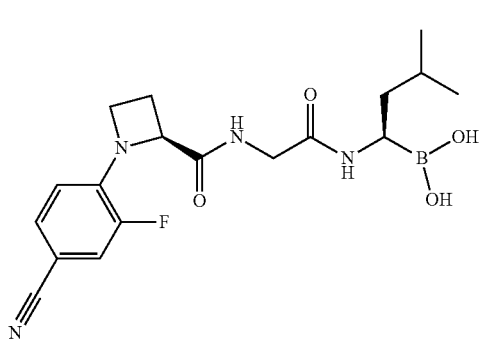
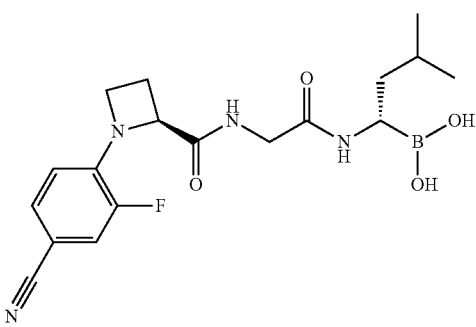
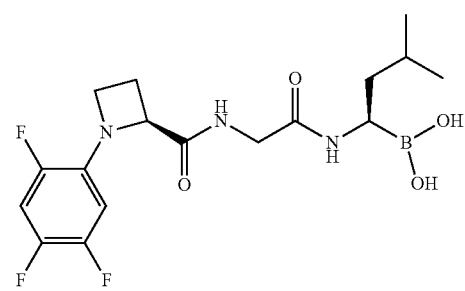
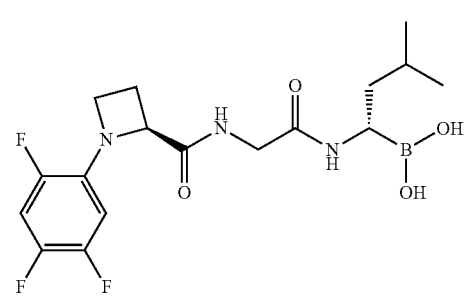
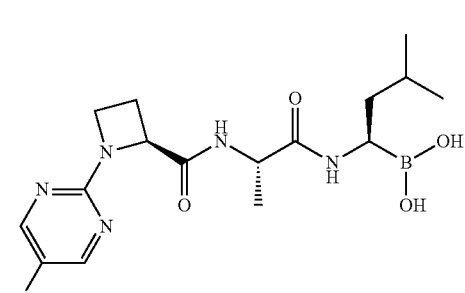
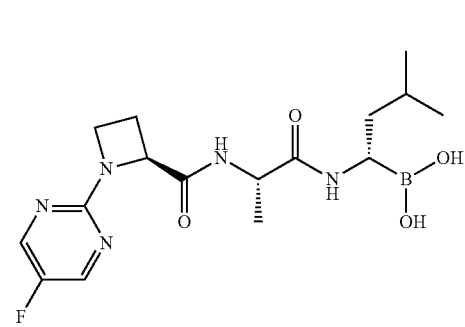

-continued

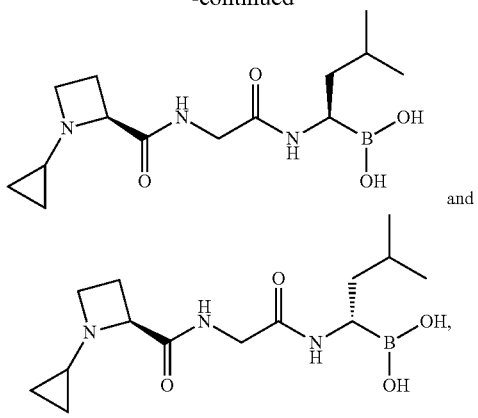

and or a pharmaceutically acceptable salt thereof.

18. A pharmaceutical composition, comprising the compound according to claim 1, or a pharmaceutically acceptable salt, a tautomer, a stereoisomer or a geometric isomer thereof, and a pharmaceutically acceptable carrier, excipient or adjuvant.

19. A method for alleviating or causing the regression of multiple myeloma, comprising administering to a subject in need thereof the compound according to claim 1, or a pharmaceutically acceptable salt, a tautomer, a stereoisomer or a geometric isomer thereof.

20. The compound according to claim 1, wherein $R_2$ and $R_3$ are each independently selected from the group consisting of H, Me,

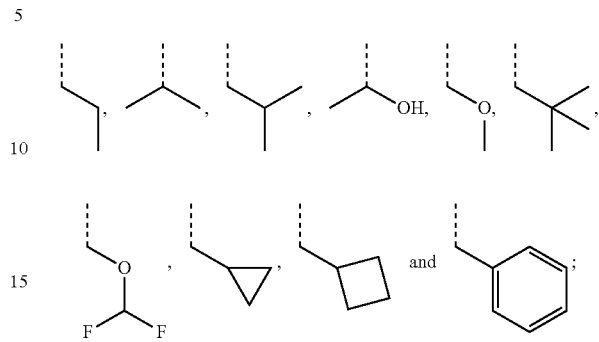

or the structural unit

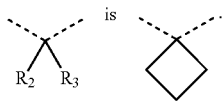

* * * * *